US012558043B2

(12) United States Patent (10) Patent No.: US 12,558,043 B2

Ruff et al. (45) Date of Patent: *Feb. 24, 2026

(54) IMAGING SYSTEMS AND METHODS

(71) Applicant: OXOS Medical, Inc., Atlanta, GA (US)

(72) Inventors: Evan Ruff, Atlanta, GA (US); Gregory Kolovich, Savannah, GA (US); Dev Mandavia, Atlanta, GA (US); Dhruv Vishwakarma, Suwanee, GA (US); Igor Zamlinsky, Roswell, GA (US); Sean Dolan, Atlanta, GA (US)

(73) Assignee: OXOS Medical, Inc., Atlanta, GA (US)

( * ) Notice: Subject to any disclaimer, the term of this patent is extended or adjusted under 35 U.S.C. 154(b) by 48 days.

This patent is subject to a terminal disclaimer.

(21) Appl. No.: 18/462,193

(22) Filed: Sep. 6, 2023

(65) Prior Publication Data

US 2023/0414185 A1     Dec. 28, 2023

Related U.S. Application Data

(63) Continuation of application No. 18/190,393, filed on Mar. 27, 2023, now Pat. No. 11,832,976, which is a (Continued)

(51) Int. Cl.
| | |
|---|---|
| *A61B 6/08* | (2006.01) |
| *A61B 6/00* | (2006.01) |
| *A61B 6/46* | (2024.01) |

(52) U.S. Cl.
CPC ................ *A61B 6/08* (2013.01); *A61B 6/463* (2013.01); *A61B 6/485* (2013.01)

(58) Field of Classification Search
CPC ..... A61B 1/247; A61B 5/0077; A61B 5/1079; A61B 6/032; A61B 6/0407; A61B 6/4417;

(Continued)

(56) References Cited

U.S. PATENT DOCUMENTS

| | | | |
|---|---|---|---|
| 4,054,881 | A | 10/1977 | Raab |
| 6,022,143 | A | 2/2000 | Helmreich |

(Continued)

FOREIGN PATENT DOCUMENTS

| | | |
|---|---|---|
| DE | 102010008552 | 11/2014 |
| DE | 102020209323 | 1/2022 |

(Continued)

OTHER PUBLICATIONS

U.S. Appl. No. 17/201,981, filed Mar. 15, 2021, Franklin et al.

(Continued)

*Primary Examiner* — Don K Wong
(74) *Attorney, Agent, or Firm* — Levine Bagade Han LLP

(57) ABSTRACT

X-ray and fluoroscopic image capture and, in particular, to a versatile X-ray emitter operative to capture images of a target configured to track and position the X-ray emission relative to an image sensor that generates the X-ray image using the X-ray emission. The system is configured to prompt the user or operator of the X-ray system with various informational data to improve the outcome of the X-ray and decrease the frequency of X-ray emissions required to obtain a desirable X-ray image.

20 Claims, 40 Drawing Sheets

Related U.S. Application Data continuation of application No. PCT/US2023/064829, filed on Mar. 22, 2023.

(60) Provisional application No. 63/269,774, filed on Mar. 22, 2022.

(58) Field of Classification Search
CPC .......... A61B 90/30; A61B 2018/00982; A61B 5/743; A61B 6/469
See application file for complete search history.

(56) References Cited

U.S. PATENT DOCUMENTS

| | | | |
|---|---|---|---|
| 6,078,036 | A | 6/2000 | Cook et al. |
| 6,173,033 | B1 | 1/2001 | Klingenbeck-Regn et al. |
| 6,266,142 | B1 | 7/2001 | Junkins et al. |
| 6,369,564 | B1 | 4/2002 | Khalfin et al. |
| 6,377,041 | B1 | 4/2002 | Jones, Jr. et al. |
| 6,400,139 | B1 | 6/2002 | Khalfin et al. |
| 6,624,626 | B2 | 9/2003 | Khalfin |
| 6,762,600 | B2 | 7/2004 | Khalfin |
| 8,821,017 | B2 | 9/2014 | Lalena et al. |
| 8,867,705 | B2 | 10/2014 | Lalena |
| 8,873,712 | B2 | 10/2014 | Wang et al. |
| 9,155,509 | B2 | 10/2015 | Lalena et al. |
| 9,474,502 | B2 | 10/2016 | Kurze |
| 9,833,209 | B2 | 12/2017 | Belei |
| 10,076,302 | B2 | 9/2018 | Franklin et al. |
| 10,098,609 | B2 | 10/2018 | Kim et al. |
| 10,143,428 | B2 | 12/2018 | Eun et al. |
| 10,188,365 | B2 | 1/2019 | Lee |
| 10,463,325 | B2 | 11/2019 | Foos et al. |
| 10,531,850 | B2 | 1/2020 | Tkaczyk et al. |
| 10,542,949 | B2 | 1/2020 | Lee et al. |
| 10,568,601 | B2 | 2/2020 | Tkaczyk et al. |
| 10,568,602 | B2 | 2/2020 | Tkaczyk et al. |
| 10,702,224 | B1 | 7/2020 | Vanhooser |
| 10,729,399 | B2 | 8/2020 | Butani et al. |
| 11,006,921 | B2 | 5/2021 | Franklin et al. |
| 11,207,047 | B2 | 12/2021 | Ruff et al. |
| 11,382,582 | B1 | 7/2022 | Ruff et al. |
| 11,540,800 | B2 | 1/2023 | Koken et al. |
| 11,684,330 | B2 | 6/2023 | Ruff et al. |
| 11,832,976 | B2 | 12/2023 | Ruff et al. |
| 11,864,937 | B2 | 1/2024 | Ruff et al. |
| 11,931,193 | B2 | 3/2024 | Ruff et al. |
| 12,115,010 | B2 | 10/2024 | Ruff et al. |
| 12,295,763 | B2 | 5/2025 | Ruff et al. |
| 2004/0105526 | A1 | 6/2004 | Zhang et al. |
| 2005/0063512 | A1 | 3/2005 | Maschke |
| 2005/0129175 | A1 | 6/2005 | Shen et al. |
| 2014/0005555 | A1 | 1/2014 | Tesar |
| 2016/0331334 | A1 | 11/2016 | Imamura et al. |
| 2017/0119339 | A1 | 5/2017 | Johnson et al. |
| 2017/0277831 | A1 | 9/2017 | Ruff et al. |
| 2017/0319143 | A1 | 11/2017 | Yu et al. |
| 2018/0235566 | A1 | 8/2018 | Tamersory et al. |
| 2019/0076106 | A1 | 3/2019 | Tkaczyk et al. |
| 2020/0289079 | A1 | 9/2020 | Tanno et al. |
| 2020/0289207 | A1 | 9/2020 | Ruff et al. |
| 2020/0289208 | A1 | 9/2020 | Ruff et al. |
| 2020/0337777 | A1 | 10/2020 | Liu et al. |
| 2021/0169438 | A1 | 6/2021 | Ruff et al. |
| 2023/0039343 | A1 | 2/2023 | Ruff et al. |
| 2023/0040643 | A1 | 2/2023 | Ruff et al. |
| 2023/0270395 | A1 | 8/2023 | Ruff et al. |
| 2023/0301609 | A1* | 9/2023 | Ruff ........................ A61B 6/08 |
| 2024/0065656 | A1 | 2/2024 | Ruff et al. |
| 2024/0206831 | A1 | 6/2024 | Ruff et al. |
| 2025/0072851 | A1 | 3/2025 | Ruff et al. |
| 2025/0255562 | A1 | 8/2025 | Ruff et al. |

FOREIGN PATENT DOCUMENTS

| | | |
|---|---|---|
| WO | WO 2020/186075 | 9/2020 |
| WO | WO 2023/015110 | 2/2023 |
| WO | WO 2023/183854 | 9/2023 |

OTHER PUBLICATIONS

US Code of Federal Regulations applying to the Food and Drug Administration Department of Health and Human Services (e.g., 21 CFR part 1020 incorporated by reference herein.) https://www.accessdata.fda.gov/scripts/cdrh/cfdocs/cfcfr/cfrsearch.cfm.

White Paper/CARESTREAM DRX-Revolution Mobile X-ray System, 4 pages, Carestream Health, Inc. 2012. CAT 200 0016 8.5x11 9/12, www.carestream.com.

* cited by examiner

1802

1804

1806

1602

1610

X-Ray
Orgin $d_a$

Aperture $d_s$

Stage

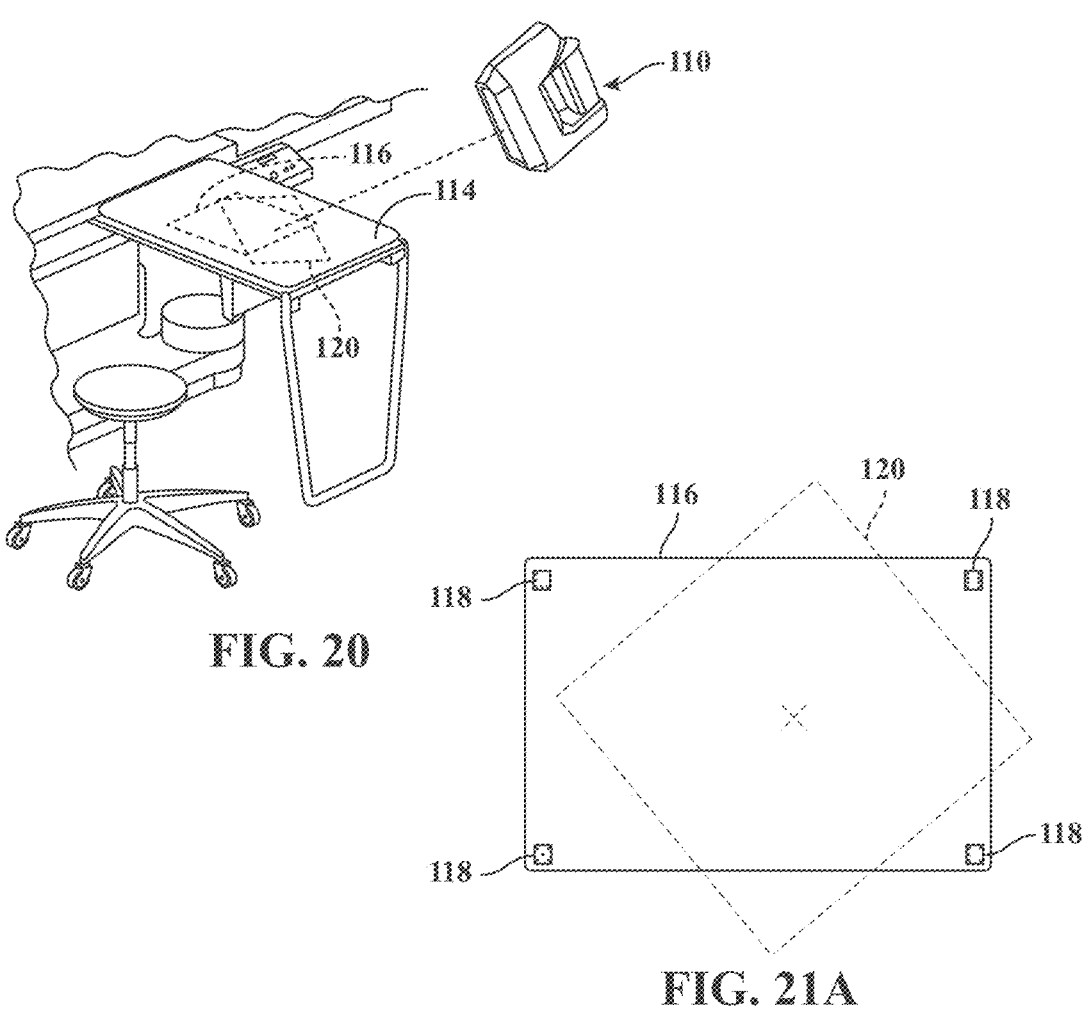
FIG. 20
FIG. 21A
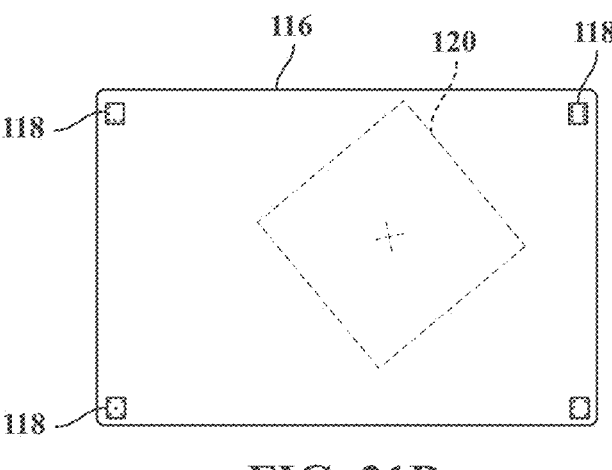
FIG. 21B

312

| Name | Note |
|------|------|
| View Name | The name of the view, such as AP, Axial, Grashey, etc. |
| Anatomy | The area of the body that is studied. |
| Reference X-Ray | Radiographic image as shown in academic reference material, such as radiopaedia. |
| Micro C Settings | M01's technique for the captured image. (KV @ time) |
| OXOS X-Ray (JPG) | Radiographic image captured by the Micro C in JPG format. |
| OXOS X-Ray (RAW) | Radiographic image captured by the Micro C in TIFF format. |
| Orthogonal Photo | A picture of the anatomy in view as if it was being captured from the perspective of the Micro C. This is what the user should expect to see in the M02 viewfinder. These photos will be submitted to an illustrator to be converted into vectors and then shown in the M02 viewfinder. |
| Setup Photo | A ¾ view of the setup of the photo, showing the patient and operator positioning and the use of any accessories, if necessary. |
| Accessories | A description of any accessories required for this view. |

| View Name | Anatomy | Imaging Instructions |
|---|---|---|
| AP | Ankle | Body Part Placement:<br>1. Extend affected leg and rest posterior surface of ankle inside active area of the cassette.<br>2. Center ankle joint in the active area of the cassette.<br>3. Flex foot with toes pointing to the ceiling to create a 90 degree angle with the ankle joint.<br>4. Make sure foot is not rotated laterally or medially. |
| Oblique - 45 degrees | Ankle | Body Part Placement:<br>1. Extend affected leg and rest posterior surface of ankle inside active area of the cassette.<br>2. Center ankle joint in the active area of the cassette.<br>3. Flex foot with toes pointing to the ceiling and plantar surface is perpendicular to the cassette to create a 90 degree angle with the ankle joint.<br>4. Medially rotate entire leg and foot so the plantar surface forms a 45 degree angle with the cassette. |
| Oblique - Mortise | Ankle | Body Part Placement:<br>1. Extend affected leg and rest posterior surface of ankle inside active area of the cassette.<br>2. Center ankle joint in the active area of the cassette.<br>3. Flex foot with toes pointing to the ceiling and plantar surface is perpendicular to the cassette to create a 90 degree angle with the ankle joint.<br>4. Medially rotate entire leg and foot so the plantar surface forms a 15-20 degree angle with the cassette. Rotate the leg from the hip. |

IMAGING SYSTEMS AND METHODS

REFERENCE TO RELATED APPLICATIONS

This application is a continuation of U.S. patent application Ser. No. 18/190,393 filed Mar. 27, 2023, now U.S. Pat. No. 11,832,976, which is a continuation of International Patent Application PCT/US2023/064829 filed Mar. 22, 2023, which claims priority to U.S. Provisional Application 63/269,774 filed Mar. 22, 2022, the entireties of which are incorporated by reference herein.

FIELD OF THE INVENTION

Improved methods and systems for X-ray and fluoroscopic image capture, and, in particular, to a versatile X-ray emitter operative to capture images of a target configured to track and position the X-ray emission relative to an image sensor that generates the X-ray image using the X-ray emission. The system also prompts the user or operator of the X-ray system with various informational data to improve the outcome of the X-ray and decrease the frequency of X-ray emissions required to obtain a desirable X-ray image.

BACKGROUND OF THE INVENTION

The availability of a small, lightweight X-ray system that allows the X-ray operator or surgeon to manipulate an X-ray emitter while the system tracks the emitter position relative to the image sensor or work space offers increased safety to the individual as well as the operator given that the resulting positioning data prevents inadvertent X-ray emission as well as reducing the need for obtaining multiple X-ray images due to inadequate positioning of the X-ray emitter relative to the detector. Such systems also will use the positioning system to show a dynamic view of the X-ray detector or working space that contains the X-ray detector. This real-time, dynamic view can give the operator a picture of the anatomy imaged before generating the X-ray and also provides a system that is capable of guiding an operator to specific X-ray views by overlaying a diagram of the subject anatomy directly on the camera view, corrected for the active area of the detector.

SUMMARY OF THE INVENTION

The invention relates to an improved versatile, multimode radiographic systems and methods, allowing the surgeon to operate on a patient without interference, and capture static and dynamic X-rays and other still and video imagery without repositioning equipment, the subject, or the surgeon.

X-ray systems are described herein that allow for safely obtaining X-ray images as well as aiding the operator of the system to obtain one or more standard X-ray images of an individual or a body part that is later examined by a medical caregiver. It is noted that, in addition to improving care of human patients, the systems and methods described herein can also be used for X-ray imaging of objects and other animals as well.

In some clinical scenarios, such as where the operator is inexperienced or is not a physician, the X-ray system can draw from a reference library or database to provide information that helps users capture the best views. In some variations, the system will display a reference X-ray (e.g., an ideal X-ray image), an orthogonal reference photo, and a patient alignment photo. For example, in a shoulder x-ray exam, the standard views of a shoulder exam are an AP view, Normal Y-view, and a Normal axial view. These views can sometimes be hard to capture for untrained operators. By providing informational images and data from a reference library, the improved X-Ray system can guide the user through these series of views and positioning of the patient, body part, and/or emitter. In addition, as the views are recorded, artificial intelligence can determine if the captured X-rays match the requested X-rays for each of the views. If a view does not meet the similarity score of the reference or if a captured X-ray image does not meet the similarity score of the reference X-rays, the device system can alert the operator for a reshoot to reduce physician intervention.

In some variations, the present disclosure includes a method of obtaining a radiological image of an individual or a body part by an operator, the method including: positioning an emitting apparatus at a distance from a working surface, where the working surface includes an imaging sensor, the emitting apparatus including a camera system and an aperture opening configured to pass an emission energy therethrough; orienting the emitting apparatus such that the aperture opening and the camera system face towards the working surface; transmitting a signal from the camera system to a display to produce an image of the working surface on the display; providing at least one informational image on the display for viewing by the operator, where the at least one informational image includes a suggested positioning of the individual or the body part; and emitting the emission energy to the imaging sensor to produce the radiological image of the individual or the body part and displaying the radiological image on the display. Variations of the method and systems include a display that is located on the emitting apparatus and/or a display located on a separate monitor.

An additional method described for obtaining a radiological image of an individual by an operator, includes: providing an emitting apparatus having a display, a camera system, and an aperture opening configured to pass an emission energy therethrough; displaying an anatomic representation on the display, where the anatomic representation includes one or more anatomic areas, where the display is configure to permit the operator to identify a selected anatomic area from the one or more anatomic areas; providing at least one informational image on the display for viewing by the operator, where the at least one informational image corresponds to the selected anatomic area, where the at least one informational image includes a suggested positioning of a body part corresponding to the selected anatomic area; positioning the emitting apparatus at a distance from a working surface, where the working surface includes an imaging sensor; orienting the emitting apparatus such that the aperture opening and the camera system face towards the working surface; transmitting a signal from the camera system to a display to produce an image of the working surface on the display; and emitting the emission energy to the imaging sensor to produce a radiological image of the body part and displaying the radiological image on the display.

The methods can include providing a virtual anatomical representation of the body part on the image, where the virtual anatomical representation is overlaid on the working surface of the image. The methods can also include positioning the body part on the working surface using the virtual anatomical representation.

In variations of the system, the imaging sensor includes a detecting perimeter, and variations of the system and methods include displaying a virtual detecting perimeter on the display, where the virtual detecting perimeter is overlaid on the working surface and corresponds to the detecting perimeter. The system and methods can also display a virtual emission perimeter on the display, where the virtual emission perimeter is overlaid on the working surface and corresponds to an emission perimeter of the emission energy from the aperture opening.

The informational image can further include providing an instructional message on the display. For example, the instructional message can include a text instruction or a video instruction.

Moreover, the systems and methods can comprise showing a video image of the workspace and/or the anatomy of the subject being examined. Alternatively, or in combination the systems and methods can include at least one non-video image of the subject/objects.

The system and methods disclosed herein can further include providing an informational data on the display, where the informational data includes a data associated with the individual.

The systems and methods can show a plurality of subset displays, wherein the image of the working surface is displayed on a first subset display and wherein the radiological image is displayed on a second subset display. In some variations, at least one informational image is displayed on a third subset display.

The methods and systems of the present disclosure can include providing at least one informational image includes selecting one or more images from a first database containing a plurality of radiographic imaging information.

In some variations, the methods described herein can further include, prior to positioning the emitting apparatus, displaying an anatomic representation on the display, the anatomic representation having one or more anatomic areas, where the display is configure to permit the operator to select one or more of anatomic areas to pre-select the at least one informational image provided on the display for viewing by the operator.

The methods and system described herein can further include performing a comparison of the radiological image to a reference radiological image and providing feedback to the operator based on the comparison.

The present disclosure includes systems for obtaining a radiological image of a body part on a working surface having an X-ray image sensor. For example, one such system includes: an emitting apparatus including a camera system and an aperture opening configured to pass an emission energy therethrough, where the emitting apparatus includes a display configured to show an image of the working surface generated by the camera system; the emitting apparatus configured to communicate with a database containing a plurality of radiographic imaging information data to display at least one informational image for viewing by the operator, where the at least one informational image includes a suggested positioning of the body part; and where the display configured to show a virtual anatomical representation of the body part on the image of the working surface, and where the display is configured to provide the radiological image after the emission energy is emitted on the body part and the X-ray image sensor.

In some variations, the present disclosure includes a system, wherein the emitting apparatus is in communication with a first database containing a plurality of radiographic imaging information, and where the at least one informational image includes one or more images from the first database containing a plurality of radiographic imaging information.

This application is related to the following: U.S. Pat. Nos. U.S. Ser. No. 10/076,302 issued on Sep. 18, 2018, U.S. Ser. No. 11/207,047 issued on Dec. 28, 2021, and U.S. Ser. No. 11/382,582 issued on Jul. 12, 2022, and U.S. Patent Application no: US20200289207, published Sep. 17, 2020. The entirety of each of which is incorporated by reference.

BRIEF DESCRIPTION OF THE DRAWINGS

FIG. 20 illustrates a situation where an emitting apparatus casts an energy profile that exceeds a profile of an imaging sensor.

FIG. 21A represents a situation in which an emission profile extends beyond a sensor such that the emitter is not in operative alignment with the sensor.

FIG. 21B represents a situation in which an emission profile is scaled to remain within a perimeter of an imaging sensor and is in operative alignment with the sensor.

FIGS. 37A TO 37C illustrate examples of database information that can be provided to various X-ray systems to improve the ability of an individual to obtain one or more X-ray images.

DETAILED DESCRIPTION OF THE PREFERRED EMBODIMENTS

Figure 1A:
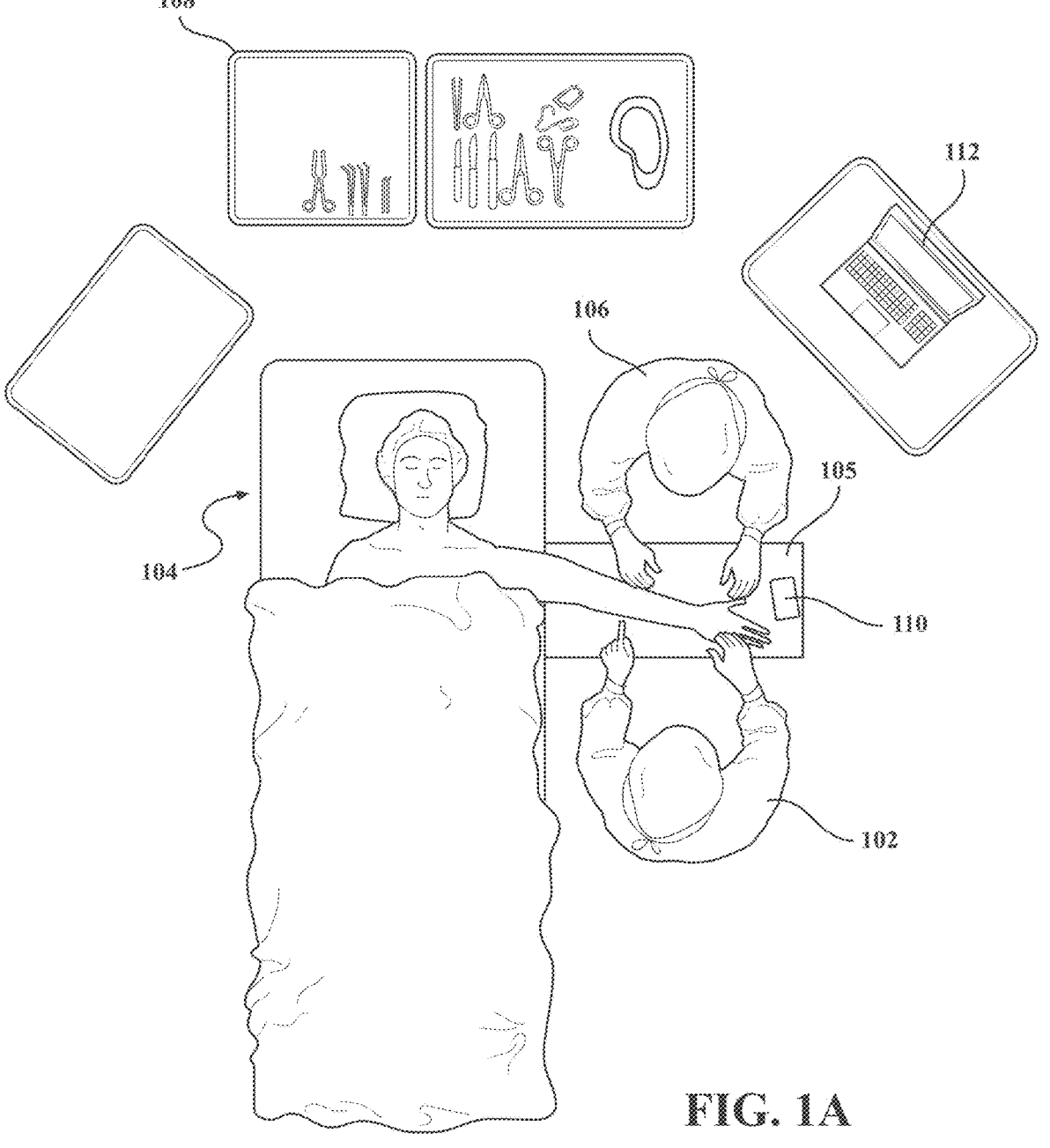
FIG. 1A depicts an example of an operating room layout for the use of the X-ray imaging system in a standard surgery of an extremity case.

FIG. 1A depicts an example of an operating room layout for the use of an imaging system in a standard surgery of an extremity case. In this example, the surgeon 102 is operating on the patient's left hand. The patient 104 is lying in the supine position with the left upper extremity prepped and draped on a hand table 105 in the abducted position. The surgeon sits adjacent to the patient's side while a surgical assistant 106 sits across the hand table adjacent to the patient's head. Surgical instruments and equipment are laid out on the back table 108 immediately behind the surgical assistant.

In one variation, the imaging system uses X-ray imaging. As such, a sterilized X-ray emitter 110, according to the invention, is placed on the surgical hand table 105 for use. A monitor 112 is positioned on a stand immediately adjacent to the hand table whereby X-ray, fluoroscopic, thermal, and digital images can be wirelessly transferred from the X-ray imaging system to the screen for surgeon view. The emitter 110 allows the surgeon to hold it with one hand while operating another instrument, such as a drill in the other hand. A detector stage, according to the invention, may be placed on or in the table 105 to gather radiographic imagery for storage and/or viewing on an external monitor such as device 112. As discussed herein, the emitter can be handheld or can be affixed to a mounting structure that is either automated/controllable or simply bears the weight of the emitter to prevent the user from constantly holding the emitter.

Figure 1B:
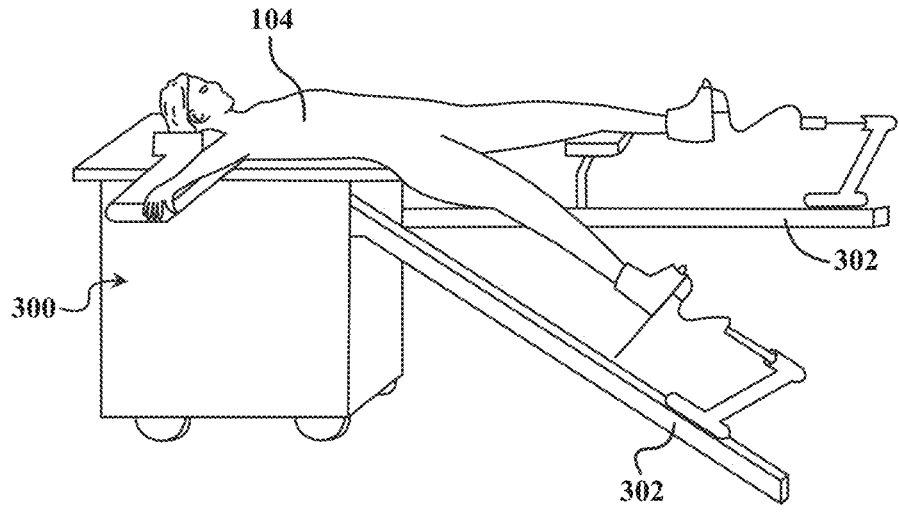
FIGS. 1B and 1C depict an alternate example of an operating room layout for the use of the imaging system with a specialized operating table that improves access to an area of a patient.
Figure 1B:
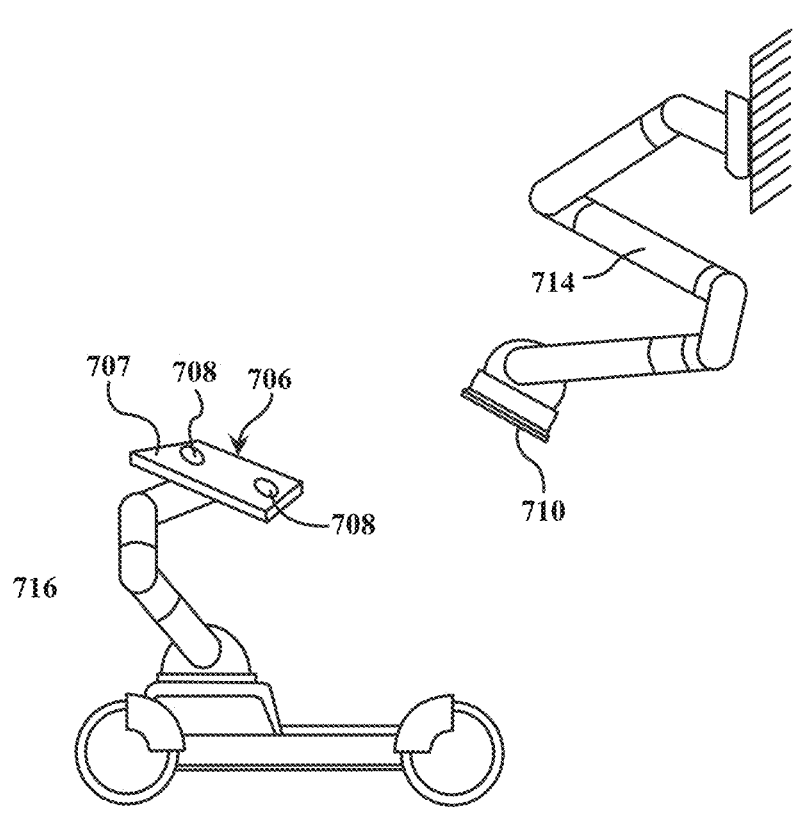
Figure 1C:
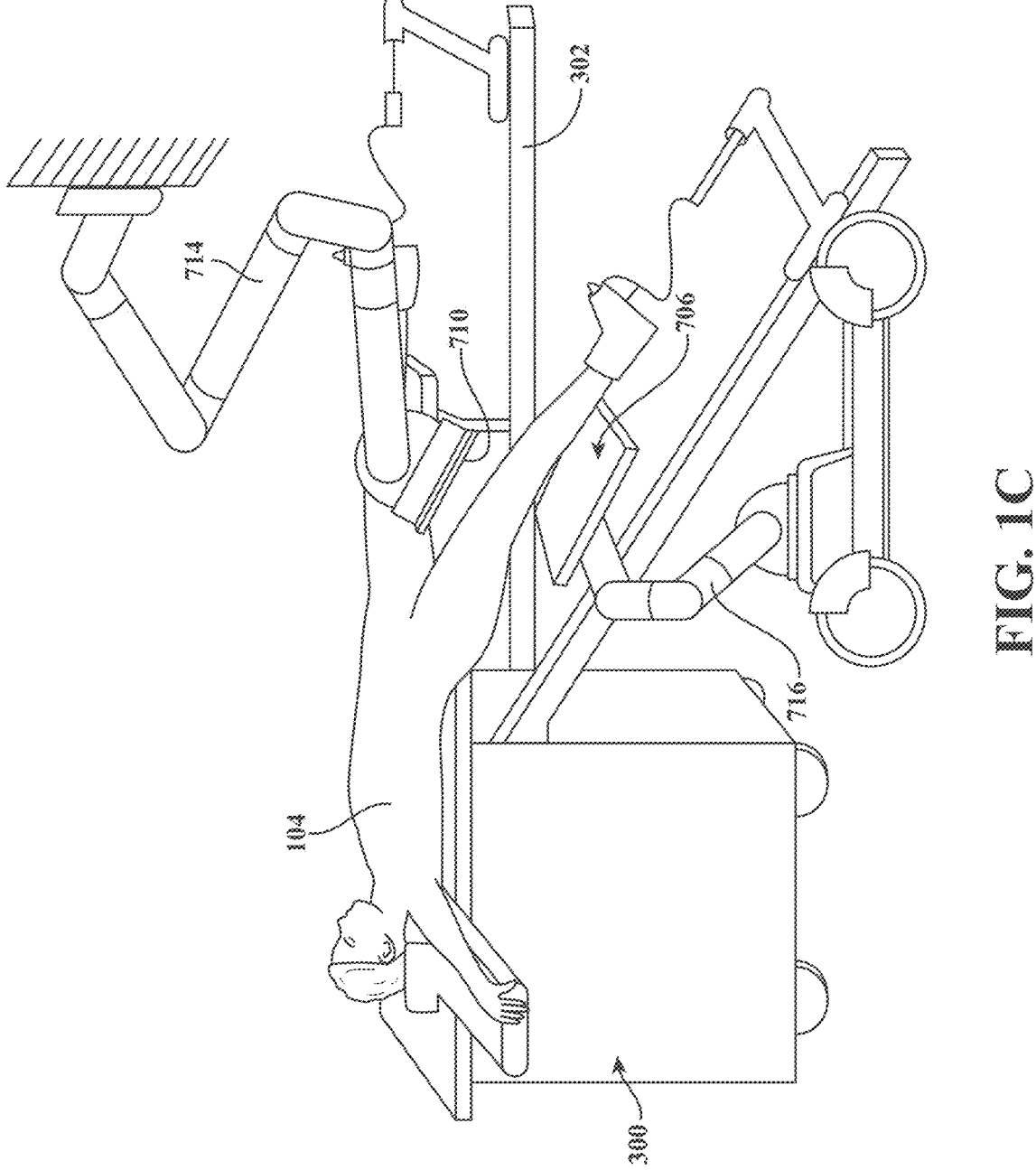

FIG. 1B illustrates an additional variation of a system including a sensor 706 and an emitter 710 for use with a specialized operating table 300. As shown, the operating table 300 includes structures 302 that stabilize the patient while allowing increased access around the patient's organs since a portion of the organ is suspended in free space. In this variation, a shell 707 containing the sensor 706 (as discussed below) is coupled to a first boom or arm 716. The arm/boom 716 allows for movement of the sensor 706. In an alternate variation, the boom 716 can be automated such that the sensor 706 is coupled directly to a controllable boom 716. Likewise, the emitter 710 is coupled to a second arm or boom 714 that can be affixed to a wall, ceiling, or portable frame structure. FIG. 1C illustrates positioning of the sensor 706 and boom 716 adjacent to a body part of the patient 104 such that the emitter 710 can be positioned as desired by the operator or medical practitioner. In variations of the system, the boom or arm can also house components of the device, such as a heat sink, power supply, etc., allowing for a more compact and easy to maneuver emitter. In addition, either boom can be designed with features to aid the physician in performing the procedure. For example, the boom can incorporate a locking system so that the physician can position either the sensor 706 and/or emitter 710 and then lock the associated boom into position. Additionally, or in combination, booms can incorporate memory positioning such that the boom can automatically retract away from the surgical space to a pre-determined location such that it automatically moves out of the way of the physician when performing a procedure. In addition, memory locations can include the "last location" of the emitter or sensor, such that the system can automatically reposition the components in their last position prior to being moved away from the surgical space.

As discussed herein, the systems described herein can include one or more distance sensors 708 located on the image sensor and/or the operating table or other region of the working area. The distance sensor(s) 708 allows measurement of any space between the body part or anatomy placed on the image sensor, operating table, and/or working area. As noted below, such an additional measurement will allow correct measurement of the thickness of the body structure if there is a gap or space between the image sensor, operating table, and/or working area and the body structure.

Figure 2:
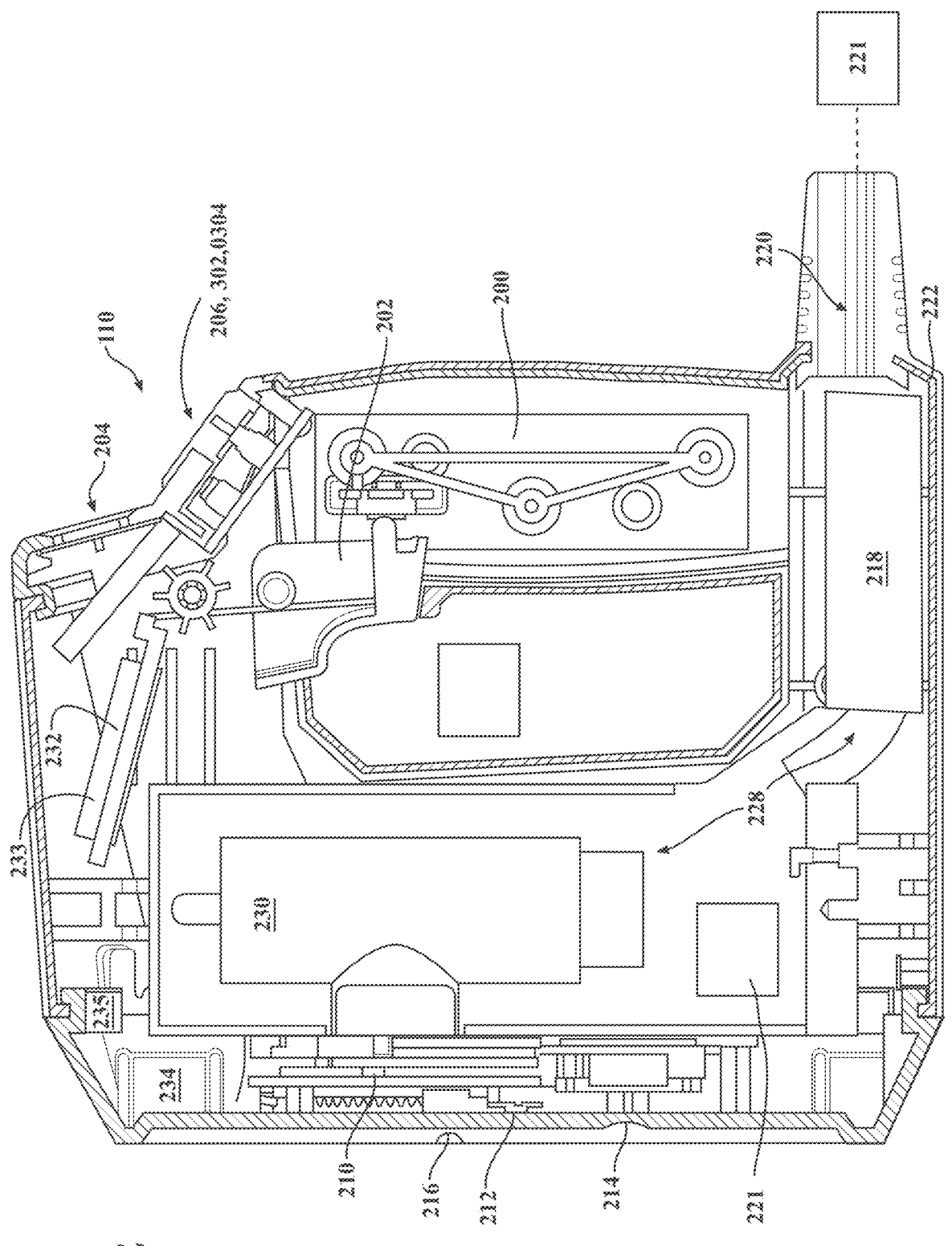
FIG. 2 is a simplified schematic representation of an X-ray emitter according to the invention.

FIG. 2 is a simplified schematic representation of an X-ray emitter according to the invention. The general configuration of the device is to be handheld, lightweight, and extremely portable. The device preferably has a rounded, contoured handle to ergonomically fit the surgeon's hand and better direct fluoroscopy, digital and thermal imagery to the extremity and surgical field.

In one variation, the back of the emitter 110 can include a control panel where at least three different modes of operation can be activated: fluoroscopic mode, digital picture mode, or infrared thermal imaging mode. Once activated, each mode is controlled in the front of the device by a trigger 202. Pressing the trigger once activates the device to take a single image (i.e., single X-ray or digital picture). Different modes of operation may be activated in different variations. As one example, holding the trigger 12 down may activate live fluoroscopy, digital video, or infrared thermal imaging. FIG. 2 also illustrates the emitter 110 as being coupled to a power supply 221. The power supply can be a battery 221 located remotely from or within the emitter 110. Alternatively, or in combination, the power supply 221 can be coupled via wiring between the emitter 110 and power supply 221. In an additional variation, the battery 221 can be positioned within the emitter 110 and used in addition to a remote power supply 221 such that the emitter 110 can be disconnected from the external power supply temporarily, with the internal battery 221 used to provide power.

Figure 3:
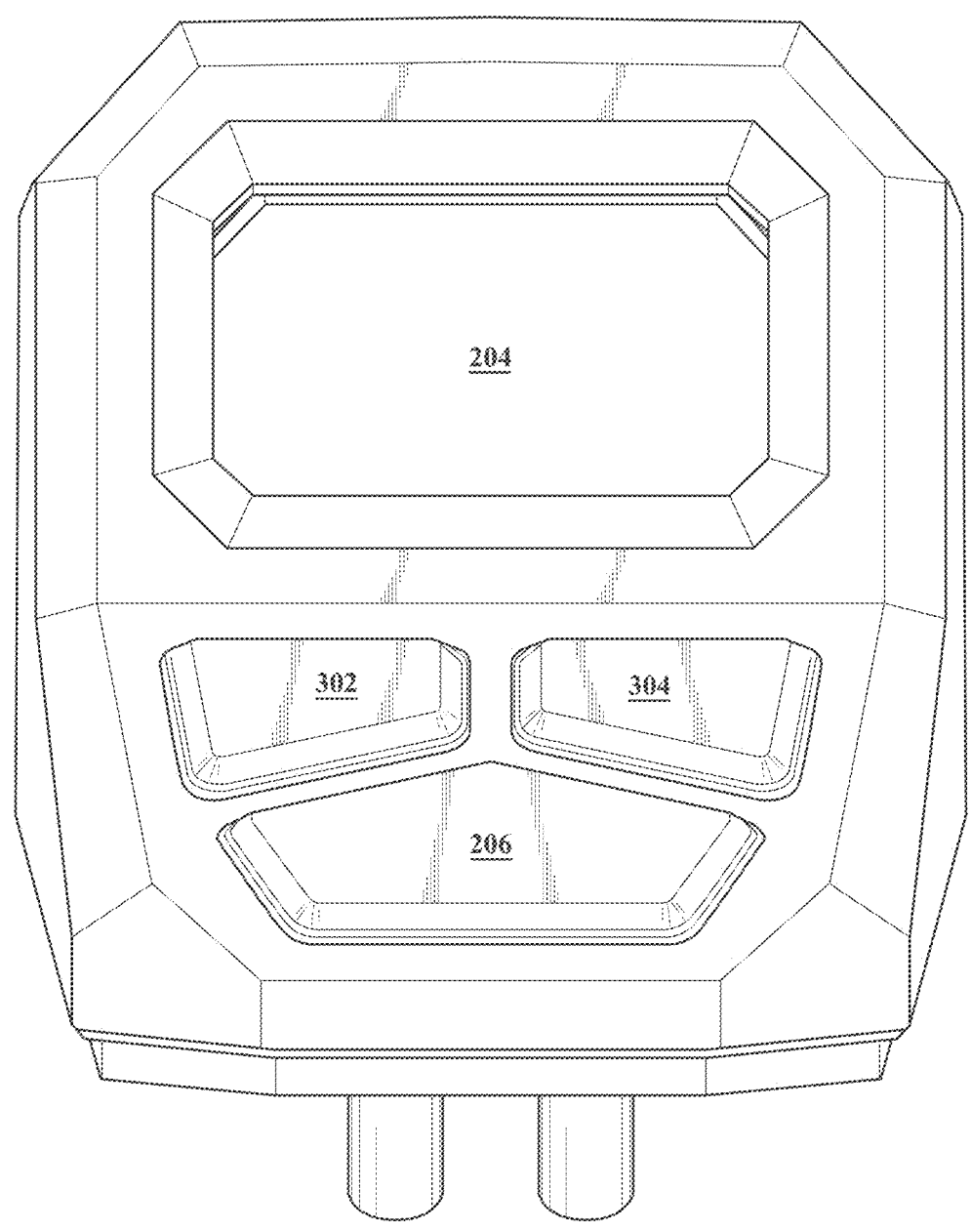
FIG. 3 illustrates one embodiment of a control panel for use with an emitter.

FIG. 3 illustrates one embodiment of the control panel for use with the emitter. The control panel is located on the rear of the emission handle and controls the various inputs and outputs of the system. The control panel is easily accessible for the user and is ergonomically designed to ease the manipulation of the emitter. The control panel comprises a large, clear screen 204 (i.e., LCD or OLED), a control button 302 located on the left of the unit, a control button 304 located on the right of the unit, and a center, clickable toggle button 206 located in the center.

Display screen 204 displays images and a digital control panel to control fluoroscopic, digital camera, and infrared settings. The control panel may include a touch screen. Toggle button 206 controls power input in fluoroscopic and infrared modes and digital zoom in the picture mode. One variation of an emitter configuration houses a dynamic X-ray collimating cone 210, digital camera lens 212, infrared camera 214, and distance sensor 216. The digital and infrared cameras preferably use charge-coupled device (CCD) technology. The distance sensor may be infrared, acoustic, or other operative technology known to those of skill in the art of proximity and distance measurement. The sensor 216 continuously senses its distance from the patient and will block the activation and discharge of radiation if the X-ray tube is too close, for example, if less than 19 centimeters directly from a patient. In addition, the system can include any number of auditory, visual, or tactile indicators to allow a physician or user of the system to determine that the sensor is within an acceptable distance or ready to fire. In additional variations, the auditory, visual, and/or tactile indicators are positioned such that the operative state of the system is identifiable without the need for the user to remove his/her focus from the object being examined. In one example, a visible indicator (e.g., one or more LEDs) is positioned on the emitter, which provides clearly distinguishable feedback regarding the distance, alignment, or any other operational conditions of the system.

The handle 200 tapers to the bottom of the device, which may house high-voltage power supply 218, external charging port 220, and battery docking station 222. Upon activation of the trigger 202 in X-ray or fluoroscopic modes, high voltage from power supply 218 is fed to X-ray generation unit 230 via the high voltage connector assembly 228. Power produced by power supply 218 is converted to a suitable input voltage that can be used by the X-ray generation unit 230. This power ranges from 1 kV to 120 kV but typically ranges between 30 kV to 90 kV in conjunction with clinical application.

The X-ray generation unit 230 is based upon existing high-voltage emitters, though custom-designed for small size required of the instant application. A suitable thickness of electrically insulating material surrounds the high voltage power supply 218, connector assembly 228 and the X-ray generation unit 230 to prevent radiation loss and preserve good beam quality. All three components 218, 228, 230 are placed immediately adjacent to each other to minimize high voltage leakage and possible interference with low voltage components in the system. In an alternative embodiment, components 218, 228, 230 may be disposed in an external control unit (not shown).

A suitable layered combination of silicone rubber and epoxy encapsulates the X-ray generation unit 230 (except where X-rays are emitted into collimator) in order to shield radiation losses and dissipate high temperatures generated by X-ray tube operation. Radiation is produced by the X-ray tube and transmitted via the collimating cone 210 at the head of the device. Fluoroscopic settings include peak kilovoltage (kV), amperage (mA), and digital brightness, are controlled by the digital control panel on the back of the neck.

The digital camera lens 212 and infrared thermal camera 214 are immediately adjacent to the collimating cone 210, and these components are also shielded by insulation. The digital camera 214 is controlled by placing the device in digital mode using the control panel. Pictures are generated via the trigger 202 located on the device handle.

Similarly, the infrared thermal camera 214 is controlled by placing the device in infrared mode using the control panel. Live infrared thermal imaging is generated by holding the trigger down. Digital X-rays, traditional digital visible and thermal images may be transferred and displayed on the external screen 112 shown in FIG. 1. Depending upon the level of cooperation between the emitter and the detector described herein, X-ray images may be transferred directly to the external monitor for viewing. A memory 233 may be used to store any type of gathered image, and such images may be encrypted upon capture in accordance with co-pending U.S. patent application Ser. No. 15/466,216, the entire content of which is incorporated herein by reference. An audio pickup 235 may be provided for procedure memorialization or other purposes, and the recordings may also be stored in memory 233, optionally in encrypted form as well.

The device is powered by an external plugin power supply with external charging port 220. The digital display, control interfaces, and trigger are controlled via the control system microprocessor electronic control unit 232, powered by a low-voltage power amplifier system 234. The low-voltage amplifying system 234 and the microprocessor control system 232 are also conveniently located away from the high voltage power supply to further minimize interference.

The following Table lists the various control modes associated with the emitter using the buttons and toggle switch on the control panel of FIG. 3:

| Control | Mode | | |
| --- | --- | --- | --- |
| | X-Ray | Digital | Thermal |
| Center (206) | Switch to Digital | Switch to Thermal | Switch to X-Ray |
| Left Button (302) | Increate Output Power | Toggle Macro | Decrease Exposure |
| Right Button (304) | Decrease Output Power | Zoom In | Increase Exposure |

Figure 4:
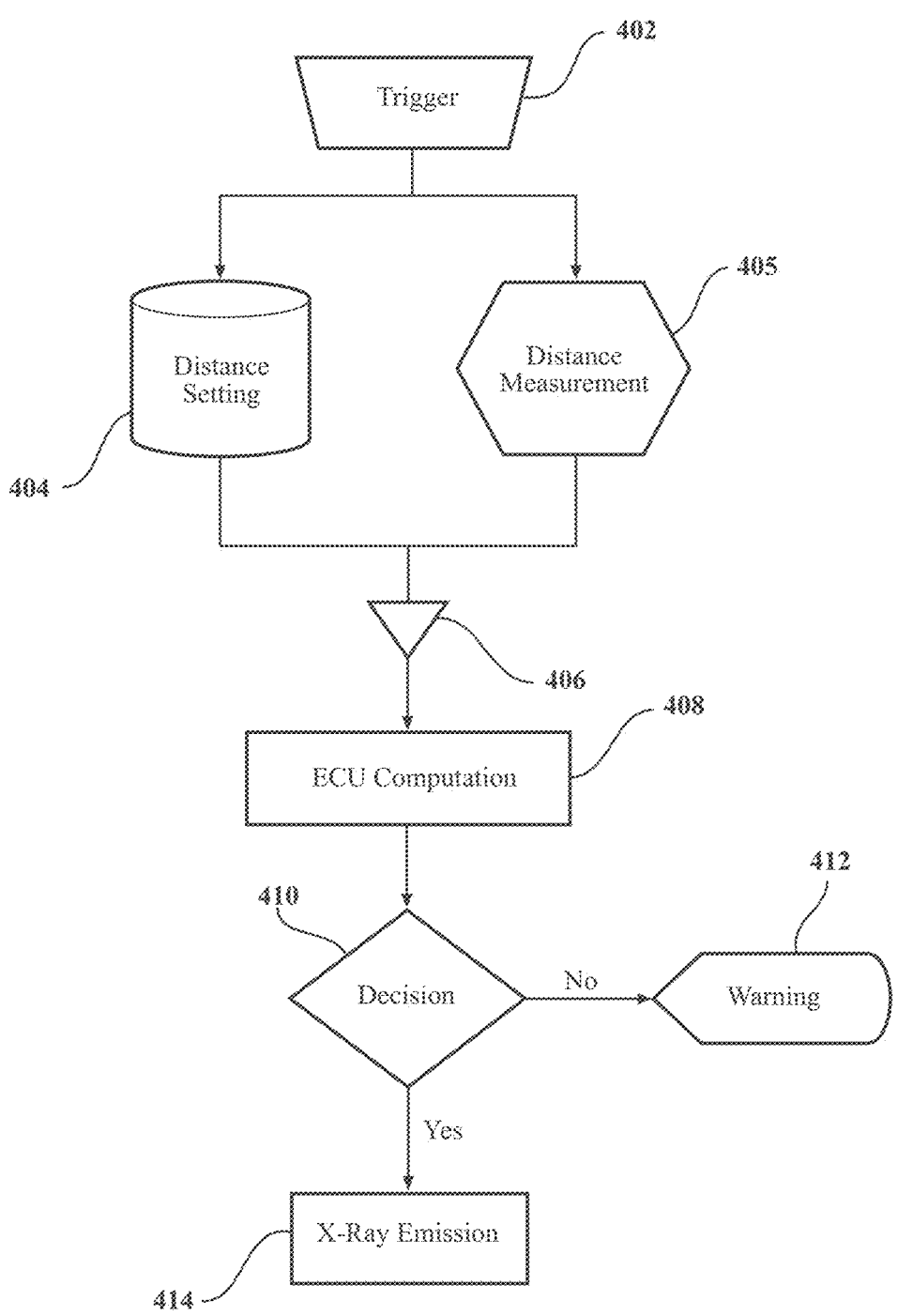
FIG. 4 shows a safety lockout procedure for an X-ray emitter.

For a variety of reasons, both practical and certification, it is important to maintain a minimum distance between the subject and the X-ray generator. This distance can change depending on a number of factors and can be configured in the emitter's software. FIG. 4 shows a process by which the device manages a safety lockout procedure of the X-ray emitter. The process to determine the safety lockout is as follows:

402. The user initiates the X-ray emission process by depressing the trigger while in X-ray mode. This could be for either a fluoroscopic or still X-ray image.

404. A distance setting is retrieved from the emitter's distance setting database.

405. The distance measurement unit is activated and captures the distance between the end of the emitter and the subject directly in front of the emitter.

406. The distance setting and distance measurements are relayed to the emitter's ECU Computation unit.

408. At 408, the ECU Computation unit uses the distance measurement, distance setting and an internal generator offset to determine if the emitter should fire.

410. The fire/warn decision at 410 is determined by the ECU and relayed to the hardware units.

412. At 412, if the ECU determines that the subject is too close to the emitter, the unit will activate a warning procedure, displaying a message on the LCD panel and activating any lockout warning lights.

414. If at 414 the ECU determines that the subject is at a safe distance, the emitter will begin the X-ray generation and emission process, signaling all internal and external components.

Due to the fact that the device can move freely in 3-dimensional space, the projected cone from the X-ray emitter varies in size based on the distance to the target. As such, the invention allows managed control over the cone size based on the distance of the X-ray emission device from a sensor positioned on the stage.

Figure 16:
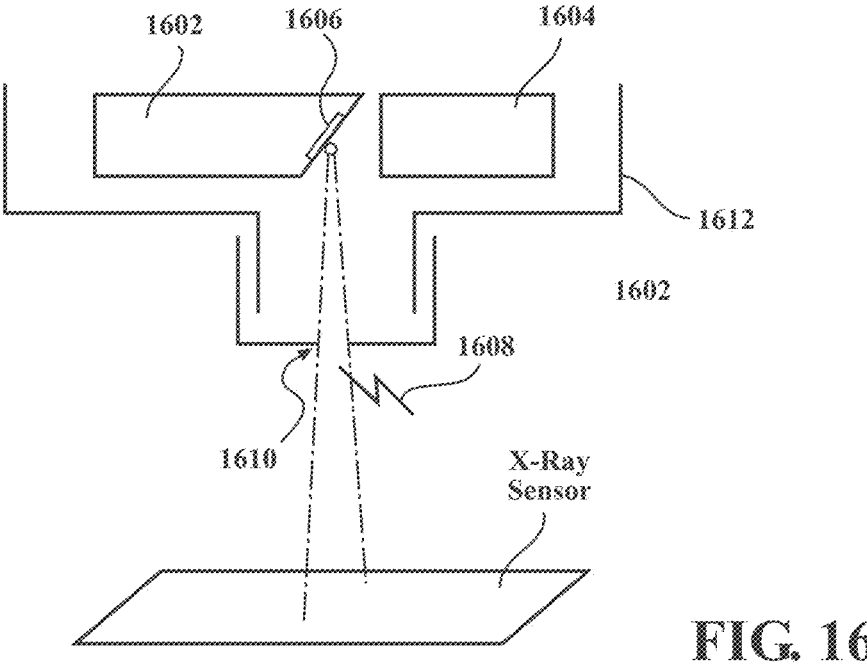
FIG. 16 is a view showing the X-ray emission device with an aperture creating the widest cone.

FIG. 16 illustrates a simplified rendition of an applicable X-ray source, which includes an anode 1602 and cathode 1604. The anode typically includes a tungsten or molybdenum target 1606. High voltage across the anode and cathode causes X-rays to be produced at the target, which forms a cone 1608 that exits through an aperture 1610 in casing 1612.

Figure 17:
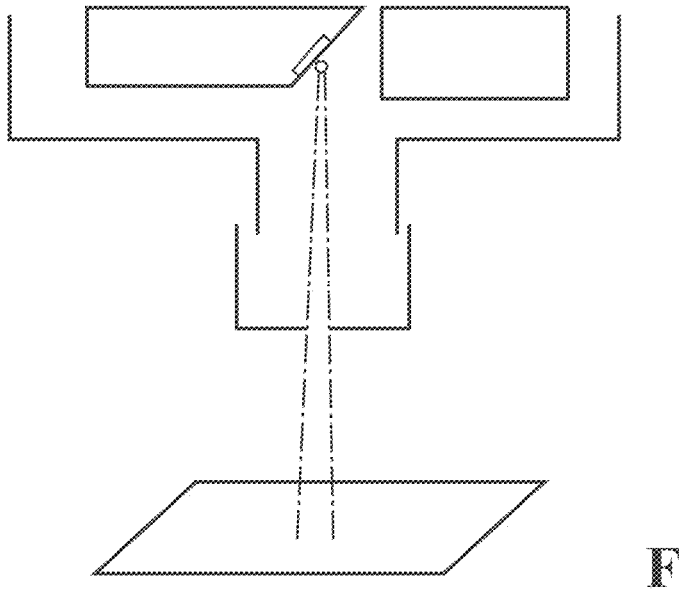
FIG. 17 shows a view showing the X-ray emission device with an aperture creating a narrow cone.

One aspect of the invention includes a telescoping chamber positioned in the direction of the aperture and sensor. The distance from the X-ray source to the output aperture can be increased or decreased by rotating the exterior chamber along a threaded interior mount. Moving the aperture closer to the source creates a wider angle, while moving it farther from the source reduces the angle, as shown in FIG. 17.

Figure 18:
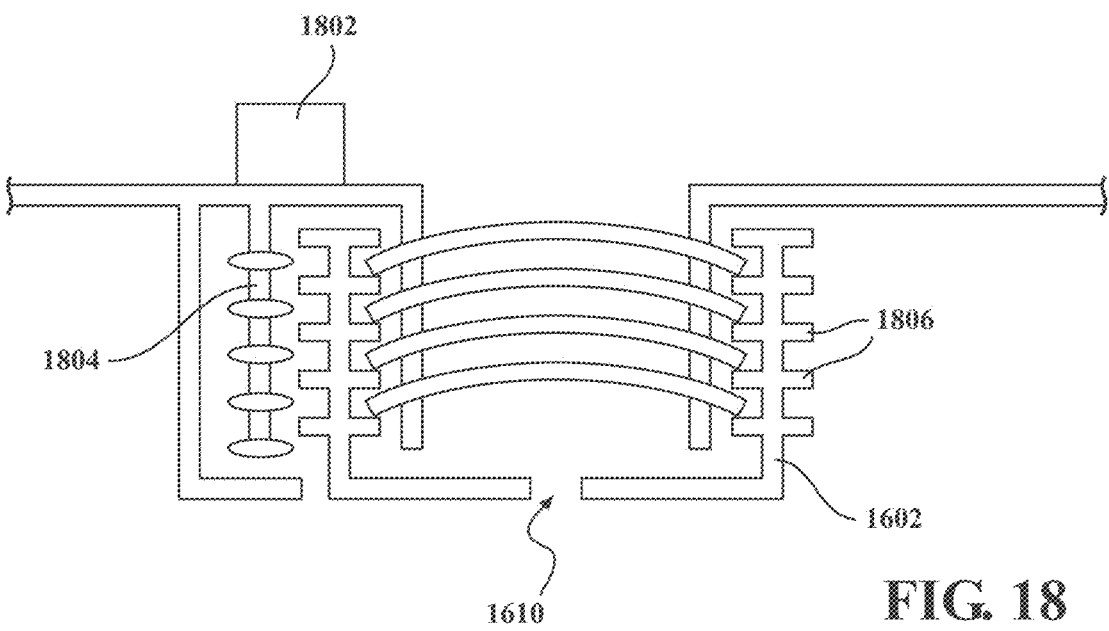
FIG. 18 shows a control unit operative to adjust the aperture and cone.

Making reference to FIG. 18, a control unit 1802 in the handheld emitter controls the telescoping aperture. Based upon the process below, the control unit 1802 rotates a threaded shaft 1804, whereupon the threads engage with grooves 1806 in telescoping chamber 1614, causing aperture 1610 to move toward and away from the X-ray source.

Figure 19:
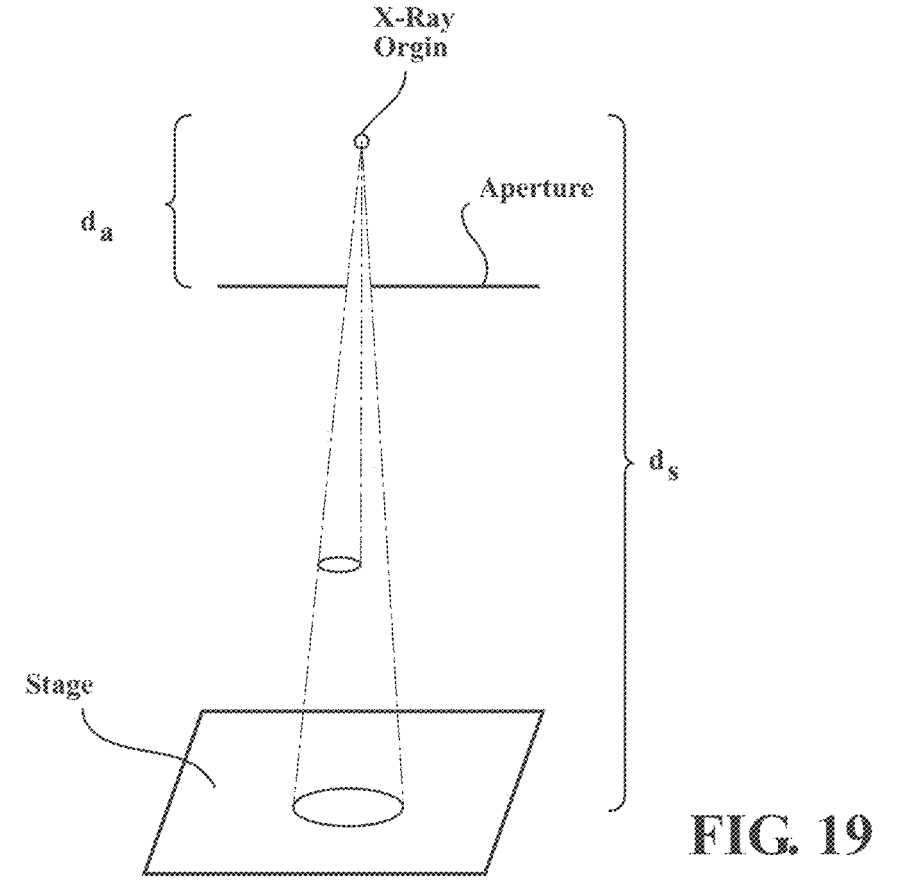
FIG. 19 is a labeled view illustrating relative distances.

FIG. 19 illustrates a control methodology. First, the distance between the device's X-ray origin and the X-ray sensor is calculated. If the distance is outside an acceptable range of X-ray emission, then no X-rays will be emitted. However, if the distance between the X-ray origin and the sensor ($d_s$) is within the acceptable range, the aperture will be automatically moved into place. The distance between the X-ray origin and the aperture ($d_a$) is then calculated, and the control unit rotates the aperture chamber to the correct distance.

If $R_s$ represents the radius of the X-ray emission as it contacts the sensor, then the angle between the normalized vector of the sensor plate and the dispersion cone can be represented as $\theta = \tan^{-1}(R_s/d_s)$. The distance that the aperture will need to be located from the emission origin to emit the correct dispersion of X-rays can be calculated as $d_a = R_a/\tan(\theta)$ where $R_a$ represents the radius of the aperture. The control unit then allows the X-ray emission device to emit an X-ray, which projects a cone at an angle $\theta$ onto the sensor.

While the telescoping cone adjustment mechanism described with reference to FIGS. 16-19 is an improved aperture, those of skill in the art will appreciate that a more conventional adjustable aperture (i.e., with translatable X-ray absorbing or blocking blades) can instead be used. The same math used above is applicable to this embodiment; that is, if the distance is outside an acceptable range of X-ray emission, then no X-rays will be emitted. Conversely, if the distance between the X-ray origin and the sensor ($d_s$) is within the acceptable range, the aperture will be automatically opened or closed to facilitate firing of the source.

Different markets have different safety requirements. Additionally, depending on the subject (elderly, pediatric, otherwise healthy) the lockout may be adjusted to ensure that there are no safety issues associated with the emission. The device also preferably includes the capability to intelligently conserve power by utilizing the inertial measurement unit (IMU), distance sensor unit, as well as operator-initiated command inputs. The various durations for the power stages of the unit are user-configurable so that the device can match the user's specific style and cadence.

The systems and methods described herein can also use multiple sensors for error correction and/or to improve positioning. For example, if an emitter and detector/sensor are in a given position, and the system loses tracking of one or more sensors on the platform. Ordinarily, the loss in tracking might cause a reduction in the frames per second (FPS) of the output image. To address this situation, the emitter can include one or more inertial measurement units that can track movement of the emitter to adjust the intervening frame, especially when needed. The IMU will then be used to adjust the intervening frames to increase the FPS of the output. In some variations, with IMU's of sufficient accuracy, the IMU can be used in place of or in addition to sensors on the platform.

Figure 5:
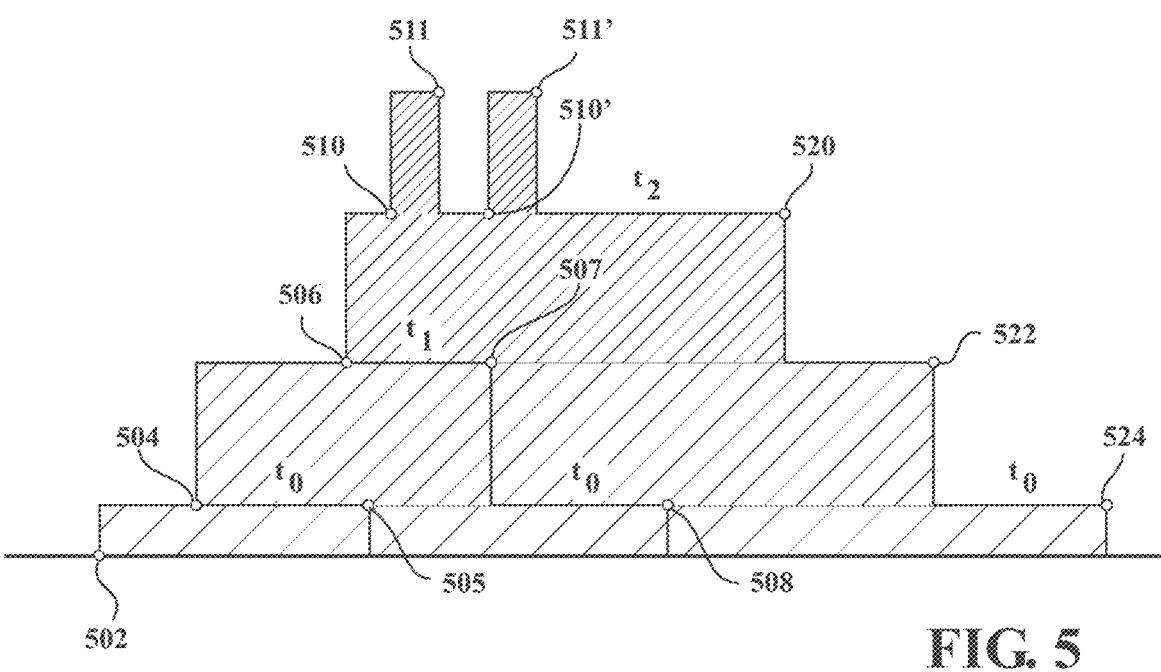
FIG. 5 depicts a representative sequence for emitter power management.

A representative sequence for power management is shown in FIG. 5.

502. The user initiates the power sequence on the device by pushing a physical button (i.e., 208 in FIG. 2) on the emitter. This engages the device's electronics and moves the device into ON mode.

504. Picking up the device is detected by the IMU in the emitter and immediately raises the power level to STANDBY. This STANDBY state initializes all power systems and raises the charge of the power supply to a medium level.

505. If the user sets the device down or is otherwise not interacted with, either through movement of the emitter or through the initiation in the control panel or control computer, the device will automatically power down to the OFF stage after a duration of t0.

506. The user has picked up the unit and has engaged the unit, either through altering of settings on the control panel itself or by bringing the device within range of a subject as detected by the onboard distance sensor. This further elevates the power level of the device by fully charging the power system to a state where the device is ready to fire, bringing the device into READY mode.

507. If, after a duration of t1 without actively engaging the unit, the emitter will power itself down to the STANDBY level.

510. The user initiates an X-ray capture by depressing the trigger 202 on the emitter. Assuming that all other safety checks are cleared, this further engages the power supply and emits the stream of X-ray photons at the subject until a state of 511, at which time the emission is complete. The user can continue to emit X-ray photons indefinitely at 510', 511', however, as the device returns to READY mode.

511. After a duration of t2 during which time the emitter has not been fired, the device will automatically power itself down to the STANDBY level at 520.

As shown with points 508, 522, 524, the device will follow the above timings to transition the device from the ON stages and finally to the OFF stage as the various durations elapse without positive engagement to maintain or change the power state. By utilizing these steps, the device can conserve power while maintaining in a ready state without any interaction from the user.

Figure 6:
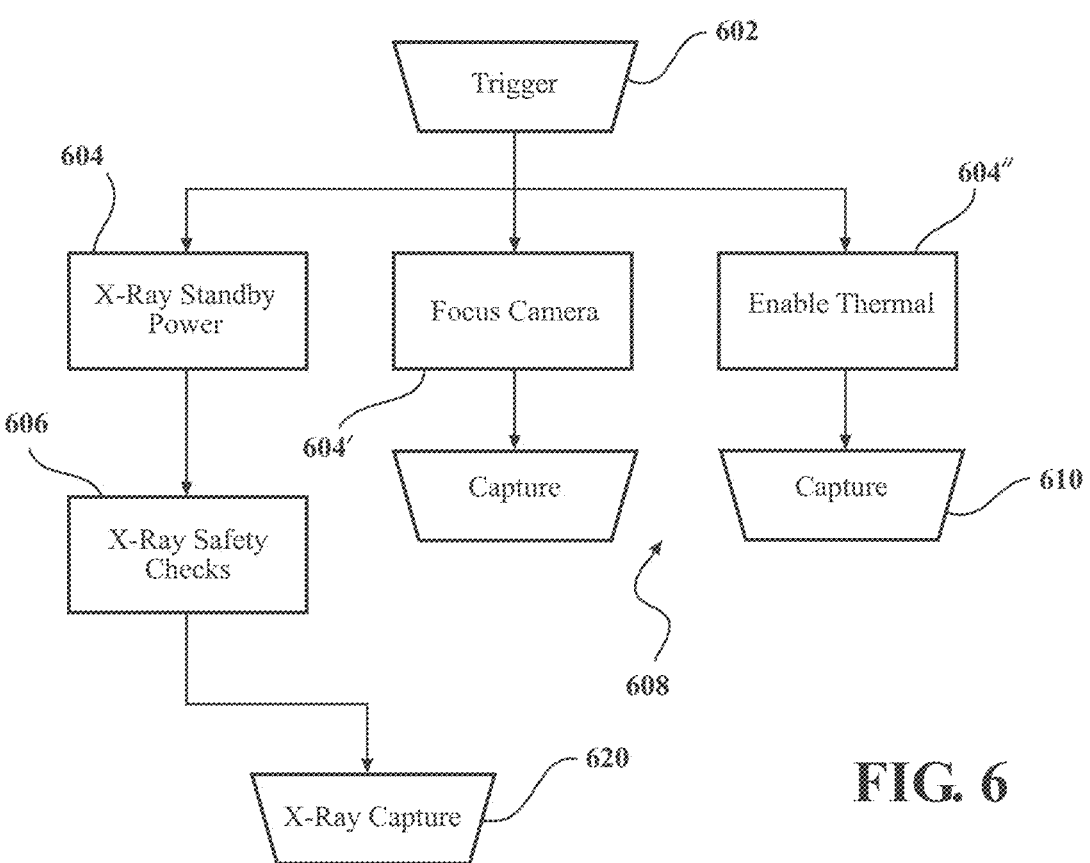
FIG. 6 illustrates a process by which a device captures concurrent images at the request of a user.

FIG. 6 illustrates a process by which the device captures concurrent images at the request of the user. Using the settings on the emitter's control screen, or by specifying a concurrent capture in the control unit, the emitter will initiate a process to capture any combination of X-ray, traditional digital, and/or thermal images. The process to capture the images is as follows:

602. The user initiates the capture sequence on the device by pulling the trigger of the emitter. This begins the capture process and concurrent imaging process for whatever grouping of sensors is enabled.

604. The emitter immediately engages the X-Ray standby mode, preparing to fire the X-ray generator.

604'. Concurrently, if enabled, the traditional camera component focuses on the desired subject. This preferably occurs as soon as the trigger is depressed.

604". Concurrently, if enabled, the thermal camera is powered on and begins its start sequence. This also preferably occurs as soon as the trigger is depressed.

606. The X-ray system begins its safety checks, as illustrated in FIG. 4.

608. The digital imaging camera captures a traditional image of the subject.

The image is preferably automatically transferred to the control unit for display on an external monitor.

610. The thermal camera captures a thermal image of the subject. The image is preferably automatically transferred to the control unit for display on an external monitor.

620. In one variation, after both 608 and 610 have completed, and all safety checks from 606 have been verified, the X-ray unit will fire an emission, generating an X-ray image in the sensor. The image is preferably automatically transferred to the control unit for display on an external monitor. Thus, the X-ray system will charge, verify safety, and discharge the X-ray only after all other systems have been executed to minimize operational interference.

X-Ray Detector Implementations

The emitter described herein must be used in conjunction with an X-ray detector to gather radiographic imagery. The emitter is not limited in terms of detector technology, and may be used with any available flat-panel detector, even film. However, given the fully portable nature of the emitter, steps should be taken to ensure that the emitter is properly oriented with respect to the detector to gather clear imagery while avoiding spurious or unwanted X-ray emissions. One option is to mount the emitter in a fixture including a properly aligned detector plate, much like a traditional C-arm though much smaller and more capable. Another option, however, is to use the emitter with the X-ray capture stages described below, one of which includes an embedded sensor that automatically pivots, orients, and aligns itself with the emitter to maximize exposure quality and safety.

One variation of an X-ray capture stage includes a statically fixed platform, positioned during the outset of surgery, with an interior cavity containing an X-ray sensor, an X-ray sensor positioning system, an emitter tracking system, a shielding system, and a control unit. The X-ray capture stage is adapted to receive an X-ray emission from a separate emitter device, including the portable, handheld unit described herein. The X-ray capture stage preferably also incorporates wireless (or wired) communications capabilities, enabling review of a captured X-ray or fluoroscopic image on an external display monitor or any other arrangement for the captured image, including external storage.

There are broadly two capture stage embodiments. In a clinical embodiment, the stage tracks the emission and simply locks out the X-ray firing if it is not in line. A tracking stage embodiment also permits or locks out emission in accordance with alignment, but also precisely tracks the position and angle of the X-ray emission, positioning and tilting the embedded sensor to capture a precise, high-quality X-ray image. This arrangement uses less power, corrects for any skew or perspective in the emission, and allows the subject to remain in place, thereby enabling the surgeon's workflow to continue uninterrupted and capture X-rays without repositioning equipment, the subject, or the surgeon.

Figure 7:
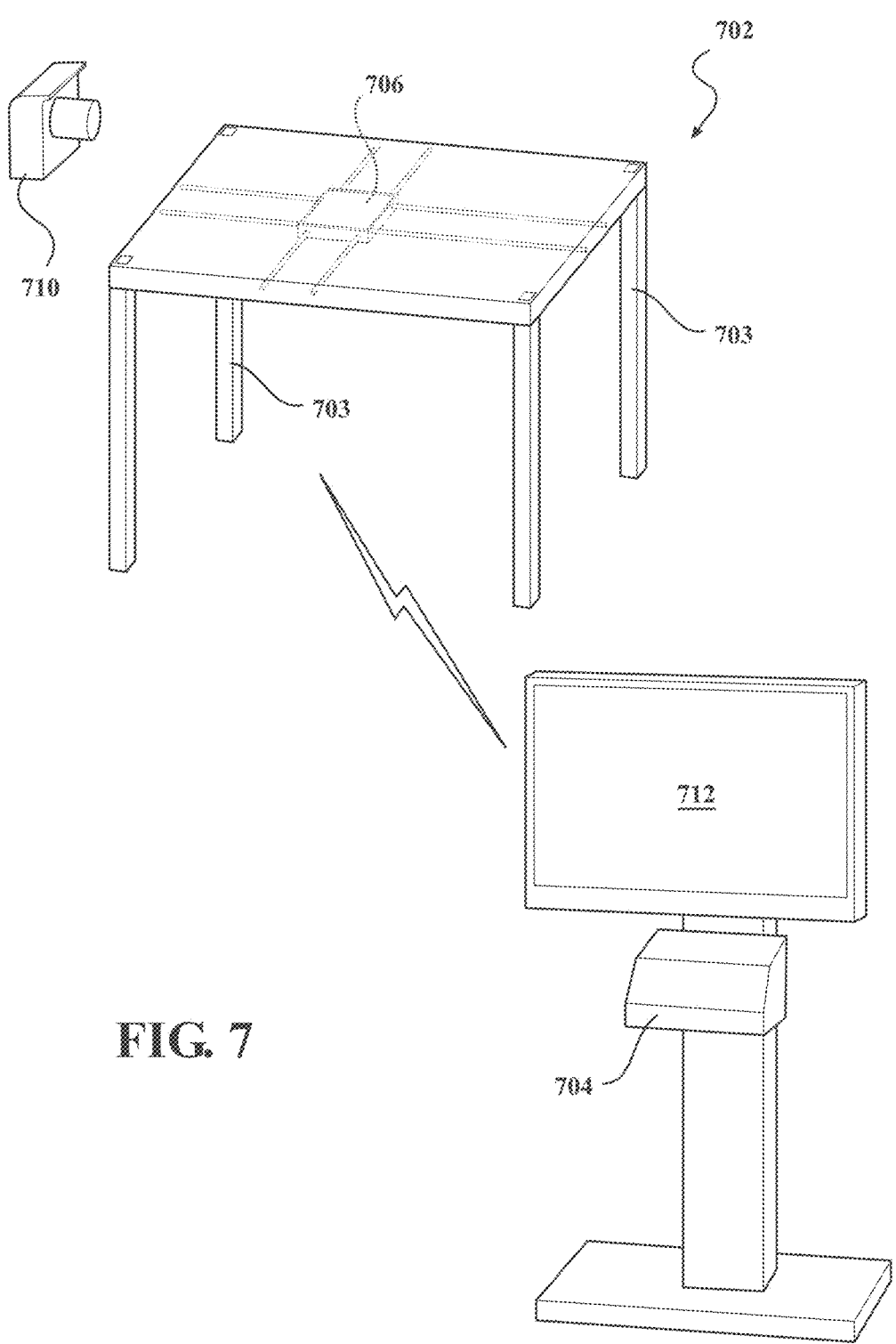
FIG. 7 is a drawing that illustrates the overall components of a variation of a capture stage.

FIG. 7 is a simplified view of a variation of the X-ray capture stage, which includes a platform 702 with a hollow cavity including the embedded sensor 706. In one configuration, the stage might have legs 703 and be used as a table. In another configuration, the stage might be wrapped in a bag and positioned underneath a patient. Thus, the platform 702 can be wrapped in a sterile drape and surgical procedures can be performed upon a platform, such as table 105 in FIG. 1.

The capture stage cooperates with a separate X-ray emission device 710. There are a number of different configurations and implementations of the X-ray emission device besides the handheld unit described in detail above, including wall-mounted, armature-mounted, and floor-mounted. Any implementation is compatible with the operative X-ray stage as long as the electronic systems of the emitter can communicate with the interface of the operative X-ray stage central control unit to provide for pivoting, orientation, or alignment.

The platform 702 is in electrical communication with a central control unit 704. A display monitor 712, electronically connected to the control unit 704, which may be used to both display images and provide overall system control. Generally, a user will interact with the emitter 710; however, in some cases, a user may interact with the central control unit 704 directly to manipulate images, set up specific capture scenarios, control parameters, or adjust other settings. The system may also use a tablet, mobile phone, or any other display device electronically connected to the central control unit for display purposes. The central control unit 704 and display may be combined in a single device, such as a laptop computer or other mobile computing device. Optionally, the central control unit can be electronically connected to multiple display units for educational or other purposes.

Figure 8A:
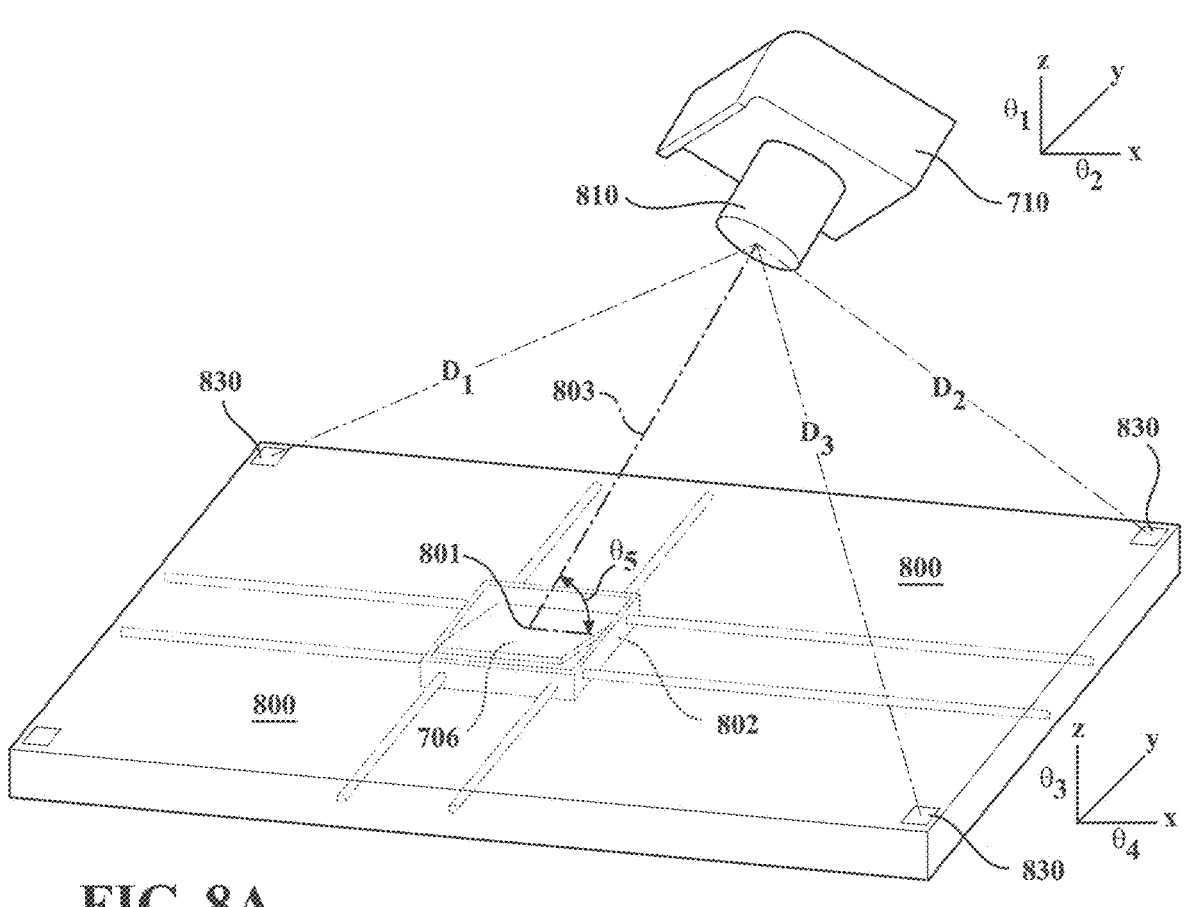
FIG. 8A is an oblique view of a sensor positioning system.

FIG. 8A is an oblique view of an X-ray capture stage according to the invention. In one specific arrangement, the stage comprises a hollow, sealed shell that is roughly 20"× 30", although the overall size of the invention can be changed to conform to other surgical applications. The shell creates a cavity 800 housing an X-ray detection sensor 706 operative to capture an X-ray emission from an X-ray emitter. Suitable X-ray sensors are available from a variety of commercial manufacturers. The sensor 706 is attached to a motorized movement system used to pan and tilt the sensor within the cavity. This motorized system ensures that the sensor is precisely positioned for maximum image quality and capture view.

Figure 9:
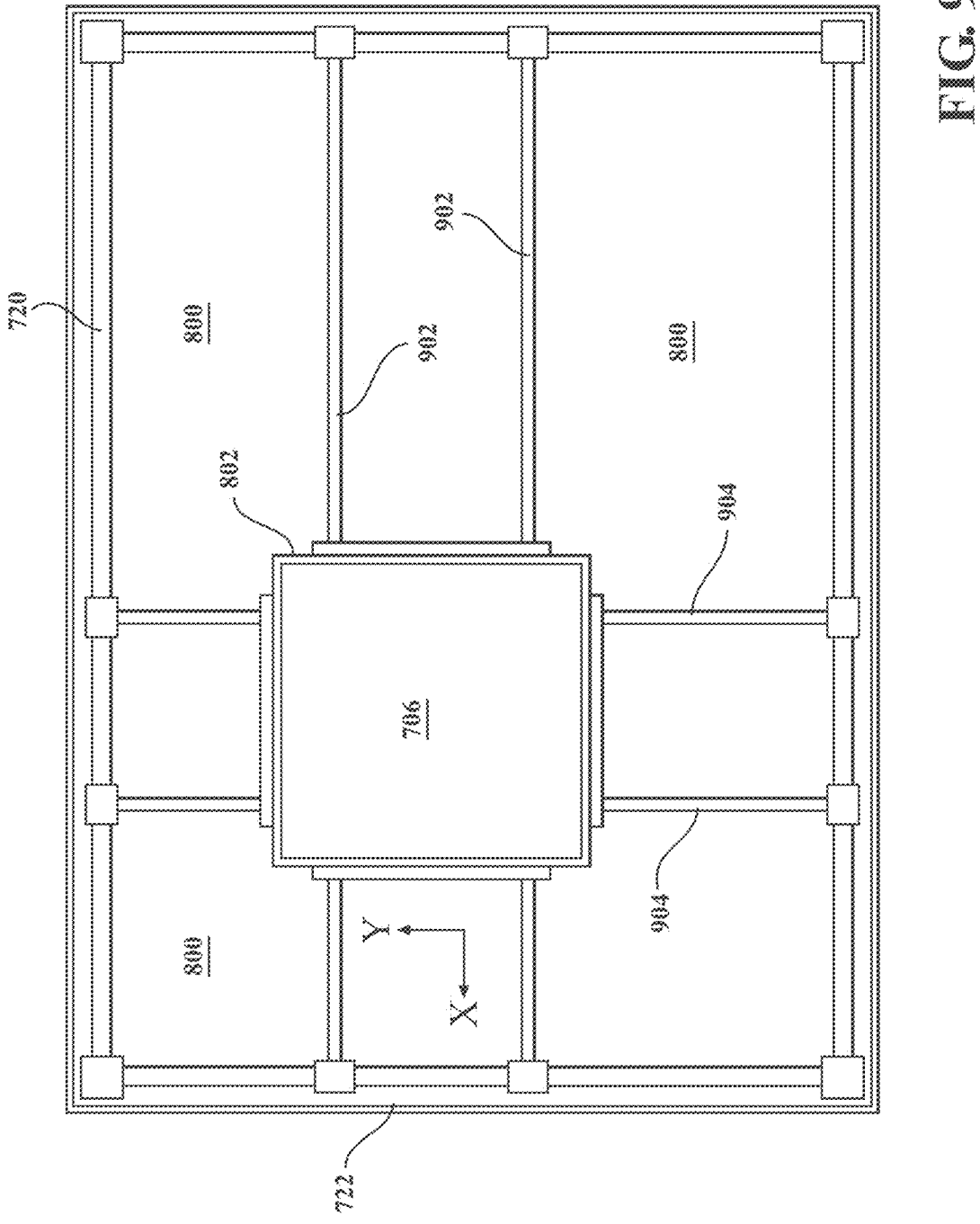
FIG. 9 is a diagram that shows x, y movement of a sensor tray viewed from above.
Figure 10A:
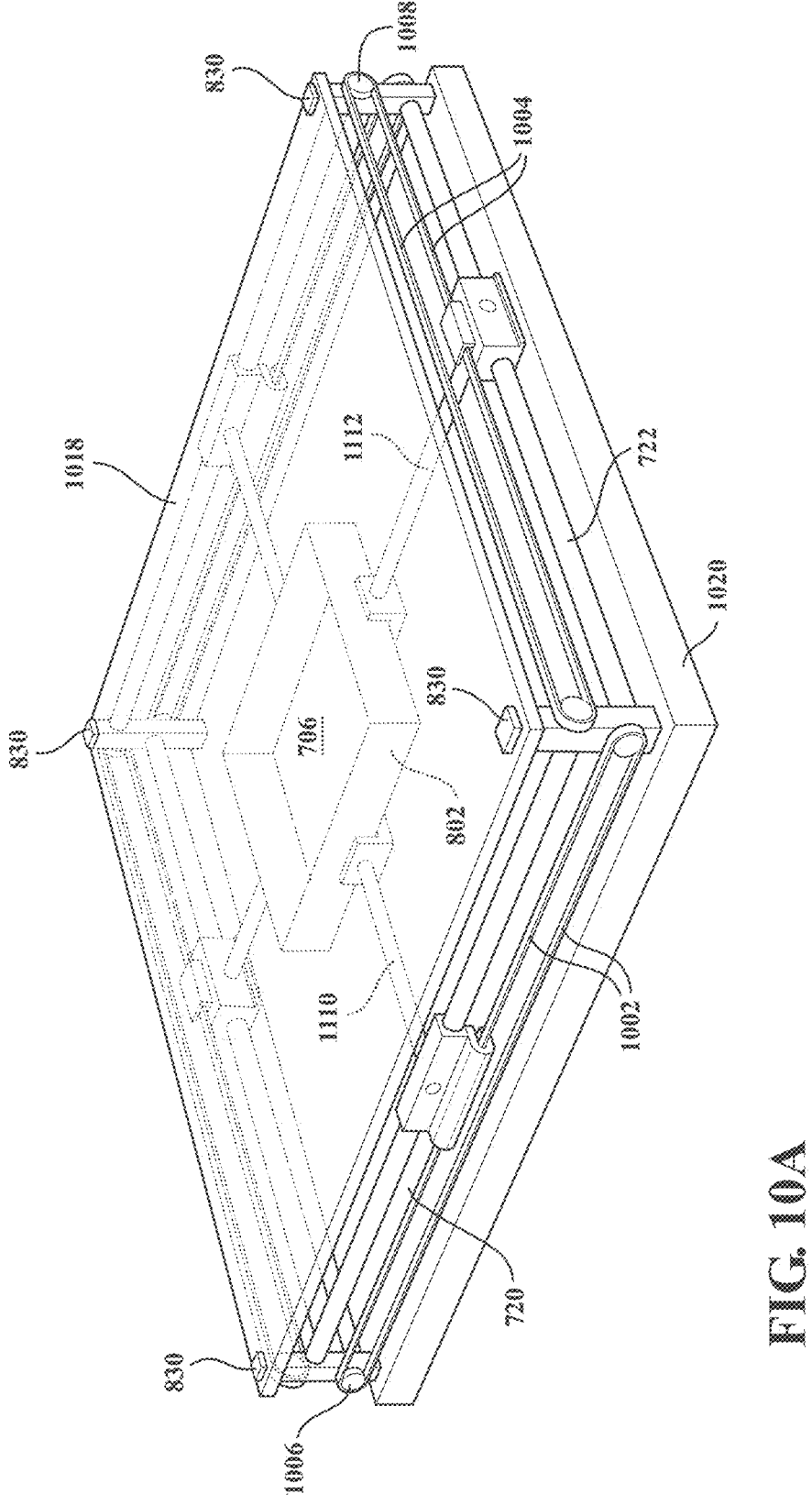
FIG. 10A is an oblique diagram showing a band-operated image capture stage.

The X-ray sensor 706 is preferably mounted to a movable tray 802 that travels under controlled movement within the cavity 800. The tray and sensor can move in the x-y direction and tilt along both axes as described below. FIG. 9 is a diagram of a capture stage seen from above. The sensor 706 in tray 802 is mounted to translate on a series of motorized rails 720, 722, allowing the sensor to position itself anywhere along the x and y axis within the shell. At least one of the x and y tracks may be a threaded rod, for example, each being driven by a motor for precise lateral movement of the tray 802 in the x and y dimensions. As a further alternative, the x-y movement of the tray may be controlled with bands 1002, 1004 in FIG. 10A. Such bands are precisely controlled by rods 1006, 1008, causing tray supports 1110, 1112 to translate tray 808. Note that while four tray supports 902, 904 are depicted in FIG. 9, single supports 1110, 1112 may alternatively be used as shown in FIG. 10A.

The emitters 830 are used to measure the distance from a point 810 on the handheld unit 710 to three (or more) fixed points 830 on the stage. These distances are depicted as $D_1$, $D_2$ and $D_3$ in FIG. 8A. Based upon these distances, the system employs a tracking method to precisely locate a center point 801 on the sensor 706 and angle ($\theta_5$) of the emission from the source to the platform. An exemplary implementation of this tracking system would include a combination of infrared sensors within the platform and the handheld unit, as well as a gyroscope in the stage and handheld unit to detect the angle $\theta_5$.

The positioning of the detector uses a number of sensors in concert. When the user picks up the handheld unit, the system enters a ready state. The infrared beacons on the corners of the table illuminate. The positioning tracking camera on the handheld unit immediately starts analyzing the infrared spectrum captured within a 140-degree field of view. The camera is searching for patterns of infrared light. Each corner 830 has a specific pattern that determines which corner of the stage the infrared camera in the handheld unit is looking at.

Figure 8B:
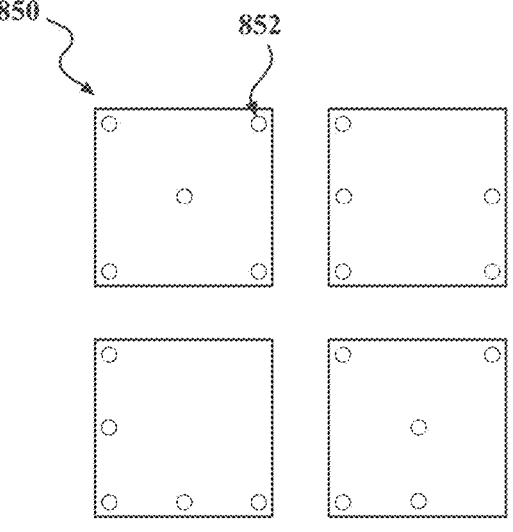
FIG. 8B illustrates infrared (IR) positioning tiles.

Making reference to FIG. 8B, an IR positioning emitter tile 850 sits at each corner of the operative or clinical stage. The diagram is an example of four unique tiles. When using the mounted positioning beacons, the pattern will be different. These tiles contain a number of infrared emitters 852, usually five individual emitters, arranged in a specific pattern. Each tile contains a different pattern of the five IR emitters. As the operator moves the X-ray emitter around the stage, the IR positioning camera captures and analyzes the IR emissions from the tiles. Because each tile has a unique pattern, the camera is able to determine its exact position in relation to the table. Additionally, because each tile has a unique pattern of multiple lights, the system can determine the exact position from the tile in XYZ space.

Optionally, or in addition to this unique IR layout, the IR emitters can flash in a syncopated manner. By modulating the frequency of the flashes, it is possible to add an additional uniqueness signature to each tile, allowing patterns to repeat in a scenario with a large number of tiles. Because of this unique arrangement, only a single corner of the unit, or single positioning beacon, needs to be visible to the emitter to allow the system to fully function. That is, due to the layout of the pattern, the camera can triangulate its position in space relative to each corner. By using the triangulation data, as well as the orientation data from the IMU unit on the emitter, the system can determine the center point of the emission. The stage will then move the center point to that area of the stage and tilt the detector to be as perpendicular to the emission as possible. While the sensor is moving into position, the collimator on the emitter adjusts the output of the beam to ensure that it is illuminating the detector panel only.

The position information from the combination of the sensors 830 is routed through the control unit (i.e., 704 in FIG. 7), which interpolates the raw sensor data into an aim point on the platform. The platform then moves the sensor tray 802 to the specified point. The platform then tilts the sensor into the correct orientation (05) to remove as much skew as possible. Stated differently, assuming the X-ray source in emitter 710 emits radiation with respect to an axis 803, the goal is to place the axis 803 as close as possible to the center point 801 of the sensor, with the plane of the sensor being as perpendicular as possible to the axis 201 to minimize skew.

In all stage embodiments, the upper cover of the platform or shell is covered with a radiolucent material (i.e., 1018 in FIG. 10A). However, the lower base of the platform (i.e., 1020 in FIG. 10A) is preferably coated with an X-ray absorbing material such as lead. This coating prevents the excess X-rays from penetrating through the field and being absorbed by the operator of the emitter. This X-ray absorbing undercoating also prevents excess X-ray emission from bouncing off the floor and scattering throughout the facility. The sides of the platform may be constructed from a radio-opaque material as well.

Figure 10B:
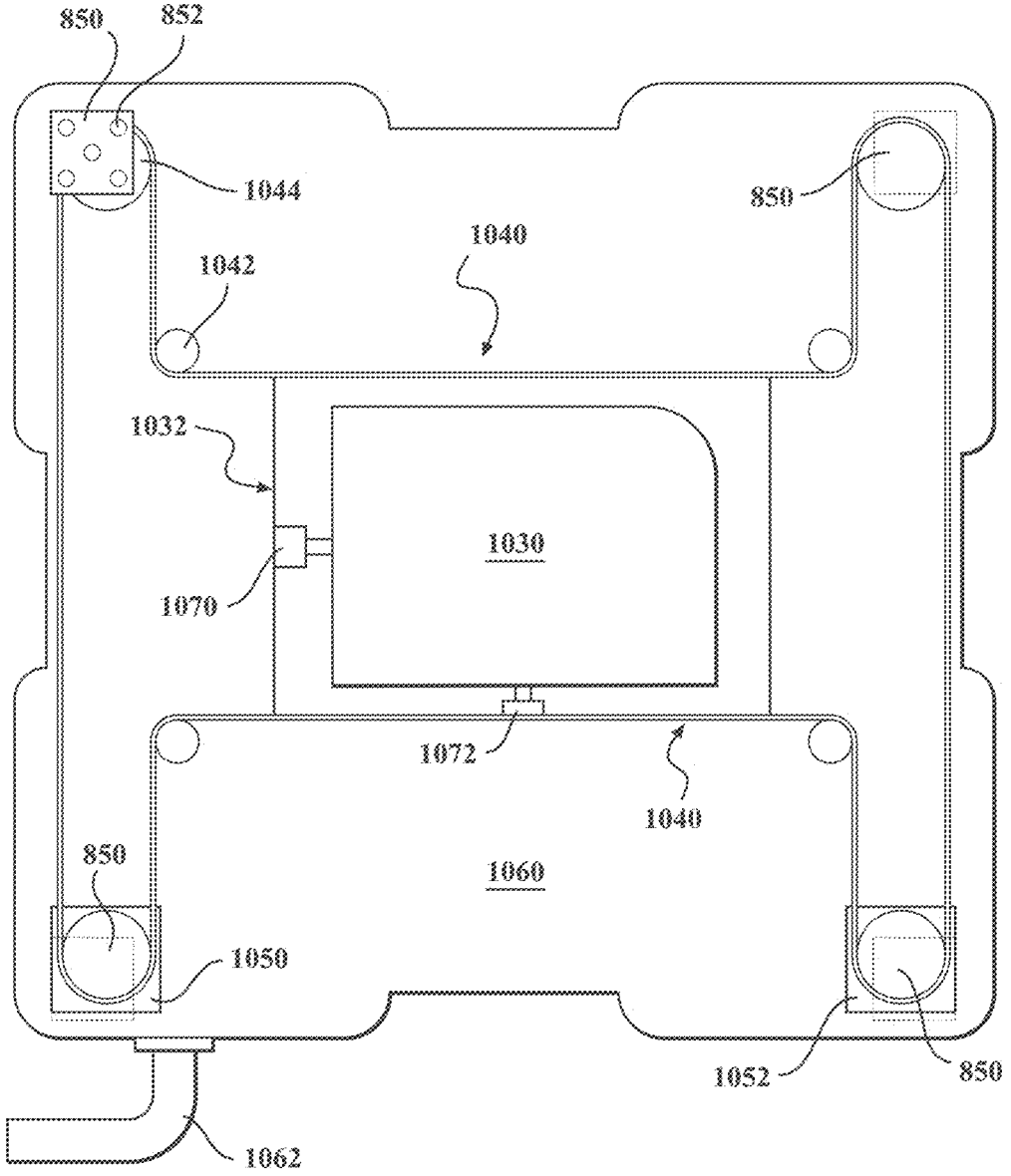
FIG. 10B is a schematic diagram of a band-operated stage with an identification of important components.

FIG. 10B is a schematic diagram of a band-operated stage with an identification of important components. The X-ray detector is shown at 1030, and the detector carrier is depicted at 1032. This particular embodiment is driven by an H-shaped belt 1040. Items 1042 and 1044 are small and large offset bearings, respectively. The belt is driven by motors 1050, 1052. The stage housing is shown at 1060, and power is brought in via cable 1062. The detector tilt motors are indicated at 1070, 1072. IR positioning tiles and IR emitters described with reference to FIG. 8B, are shown at 850 and 852, respectively. The typical IR emitters described herein are active beacons since they actively emit a signal or energy that is received by the emitter to aid in determining a position of the emitter. Alternatively, or in combination, additional variations of the methods, systems, and devices described herein can include passive markings or objects to aid in determining orientation of the emitter. The systems, devices and method can include camera or emitter that simply records a specific pattern (e.g., a QR symbol or some unique object in the surgical area such as a clock, table, fixture, etc.). The system will then rely on a computer to use these patterns in place of, or in combination with, IR beacons to determine a position of the emitter. In this latter case, the emitter position is calculated by the computer or other processing unit.

Figure 11A:
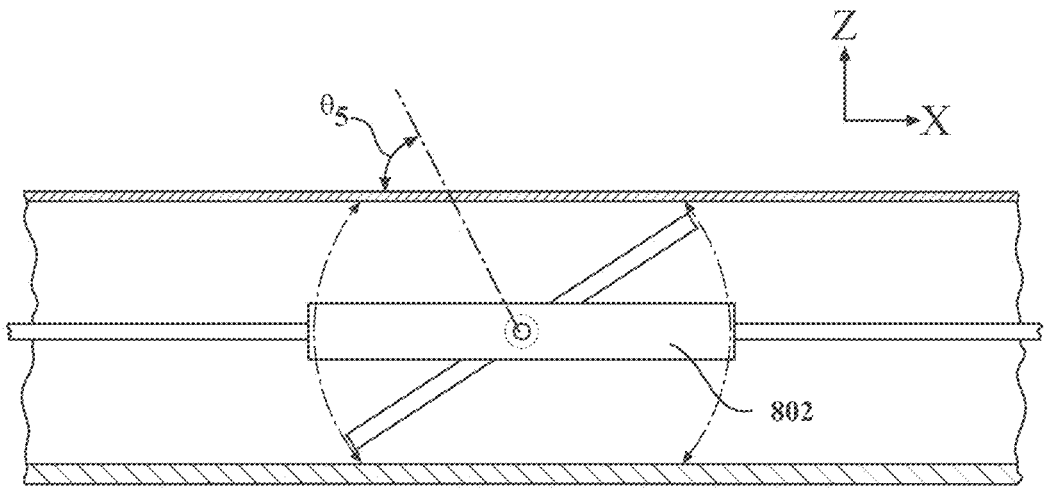
FIG. 11A is a side view showing a sensor tilt operation.
Figure 11B:
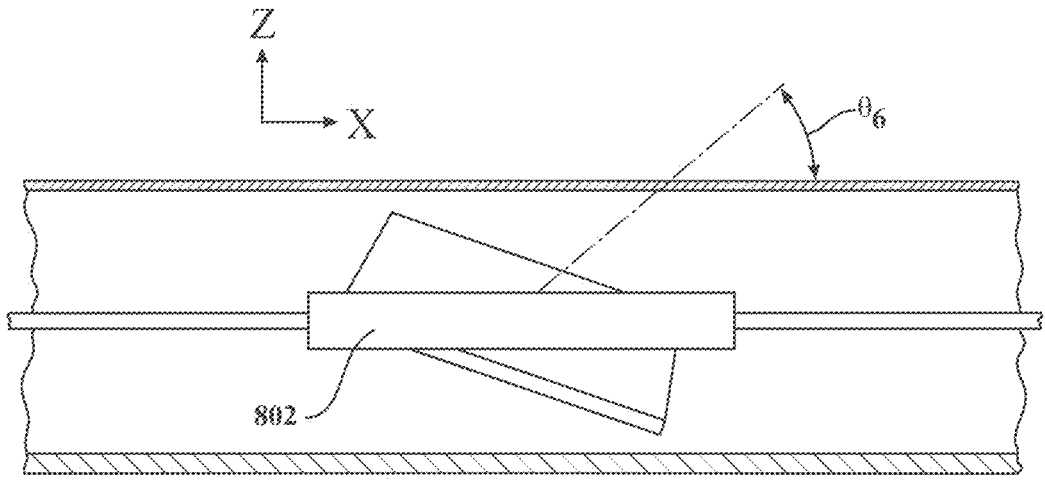
FIG. 11B is a side view showing a sensor panning operation.

FIGS. 11A, 11B are diagrams that show a pan and tilt mechanism. In FIG. 11A, the sensor tray 802 is positioned within the cavity, and the sensor 706 is tilted around the y-axis. In FIG. 11B, the sensor tray 802 is tilted along both the x-axis and the y-axis. This panning and tilting allow the sensor to be precisely positioned to capture an X-ray image while minimizing the distortion created by the offset angle of the emission device. That is, the capture stage and X-ray emitter are coordinated to minimize skew and maximize capture of both X-ray and fluoroscopic images. By moving the sensor within the stage, the user does not need to reposition the subject to get a clear, usable X-ray or fluoroscopic image.

In the case of a handheld emitter, wherein the emission device is physically decoupled from the stage, it is important to position the sensor relative to the emitter for quality and safety reasons. Different techniques may be used to accomplish this goal. As shown in FIGS. 8 and 10, a plurality of position tracking implements 830 may be mounted to the ends or corners of the tray. While these implements may be used in all four corners, only one is necessary for accurate triangulation. These implements may be based upon ultrasonic tone generation or infrared emission. In these embodiments, acoustic or infrared signals generated in the platform are detected by the emitter device, causing the sensor to translate and tilt to maximize capture. A further embodiment may utilize magnetic position and orientation sensors and detectors of the type used in surgical navigation to orient the tray and X-ray sensor.

Figure 12A:
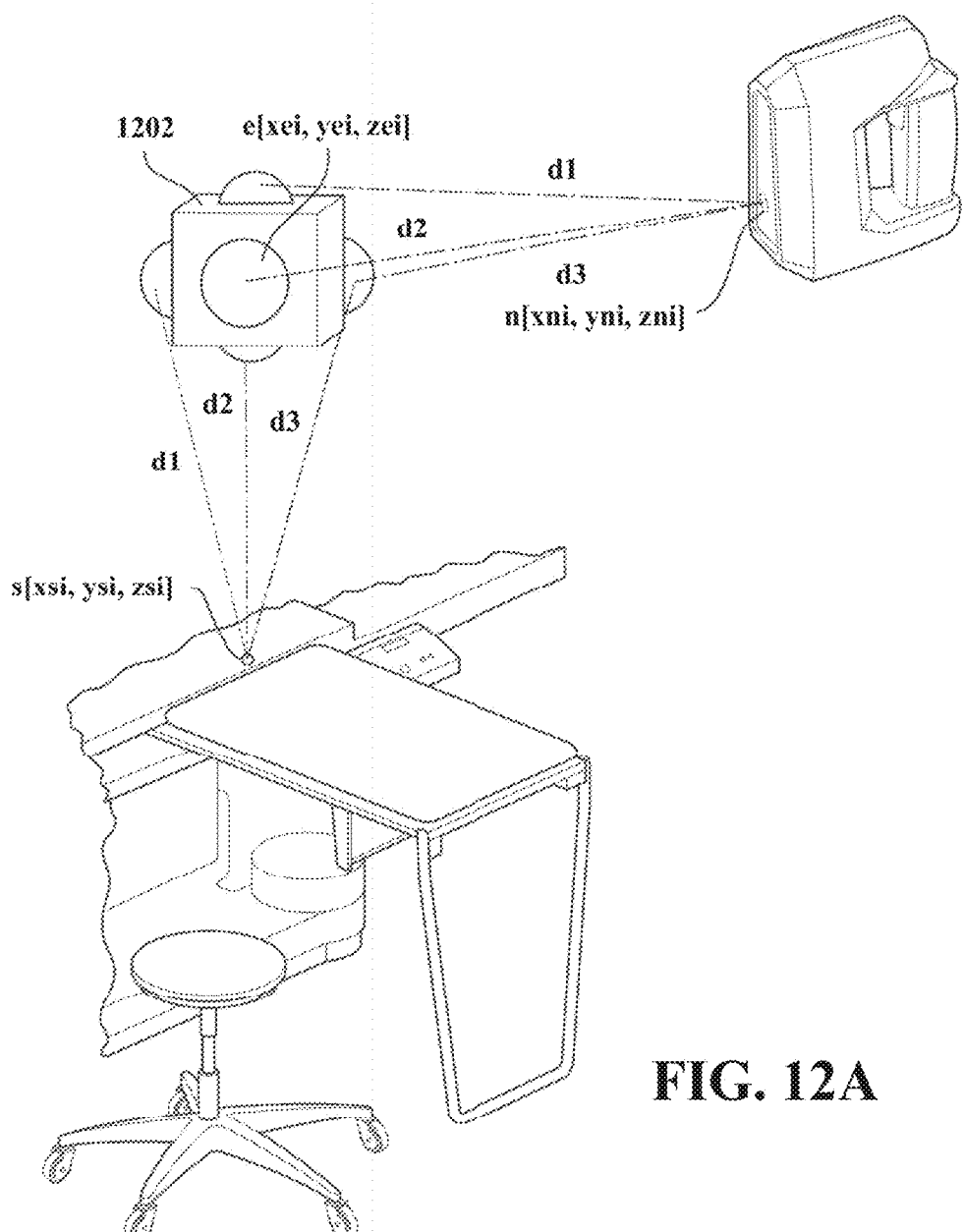
FIG. 12A illustrates an arrangement whereby an emitter need not be provided on an image stage platform.
Figure 13:
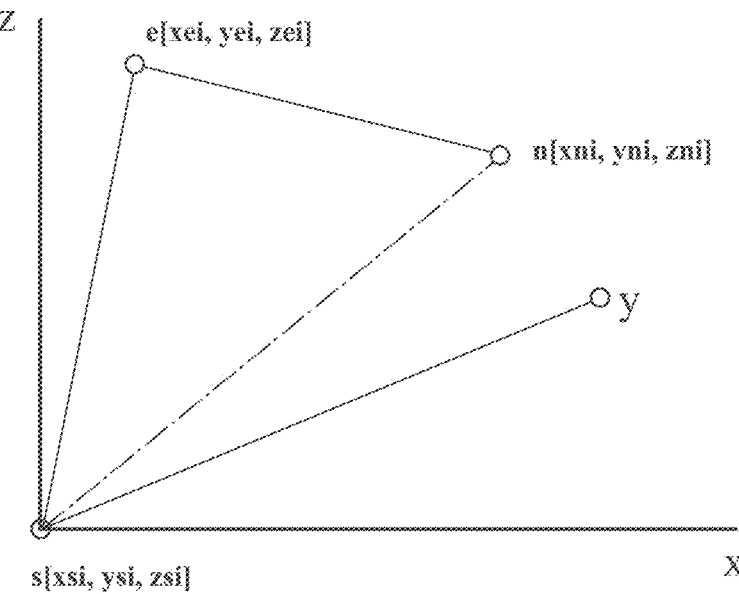
FIG. 13 is a view of an infrared emission device emitting infrared from 5 points, allowing for relative position calculation in 3-dimensional space.

The x, y, pan, and tilt positioning of the tray and sensor may be accomplished without position emitters in the platform portion of the system. FIGS. 12A and 13 illustrate an alternative system and method of position calculation that removes the dependency of having position emitters embedded in the table. Instead, the position of the X-ray emitter in relation to the capture stage and X-ray detection sensor can be calculated based on external position emitters. As noted above, the emitter can be purely handheld to allow a practitioner to move the emitter in free space. Alternatively, the emitter can be moveable with (or coupleable to) a support structure that maintains the emitter in position relative to the object without requiring the physician to continuously hold the emitter.

The process to determine the location of the X-ray emission device in accordance with this embodiment is as follows:

The external positional emission device(s) are installed onto a fixed location and contain a series of infrared emitters. This emission device releases infrared patterns from 5 sides of a cubic object 1202, resulting in infrared energy being sent out from slightly different origins.

The stage detects the infrared pattern and calculates the relative position from the stage to the center of each infrared emitter in 3-dimensional space. This position will be considered $[xsi, ysi, zsi]=[-xei, -yei, -zei]$ with s representing the stage, e representing the infrared emission device, and i representing the index of the infrared emission device (if leveraging multiple infrared emitters).

The X-ray emission device continually detects the infrared signal patterns and determines the relative location of the emission device to the center of each infrared emitter in space. This relative position is relayed to an emission position control unit for each emitter. This position may be considered $[xhi, yhi, zhi]=[-xei, -yei, -zei]$, with h representing the X-ray emission device, e representing the infrared emission device, and i representing the index of the infrared emission device.

The emission position control unit will receive the relative positions of the X-ray emission device ($[xhi, yhi, zhi]$). Using these relative positions, the emission position control unit calculates the position of the X-ray emission device relative to the stage (FIG. 13), resulting in $[xhi-xsi, yhi-ysi,$ $zhi-zsi]$. This operation is performed for each infrared emission device (i), which can then be used to deduce the margin of error.

After the stage applies the position along with the other pieces of data as mentioned in the original filing, the stage moves and rotates the X-ray sensor plate into the correct position to capture the X-ray image.

Figure 12B:
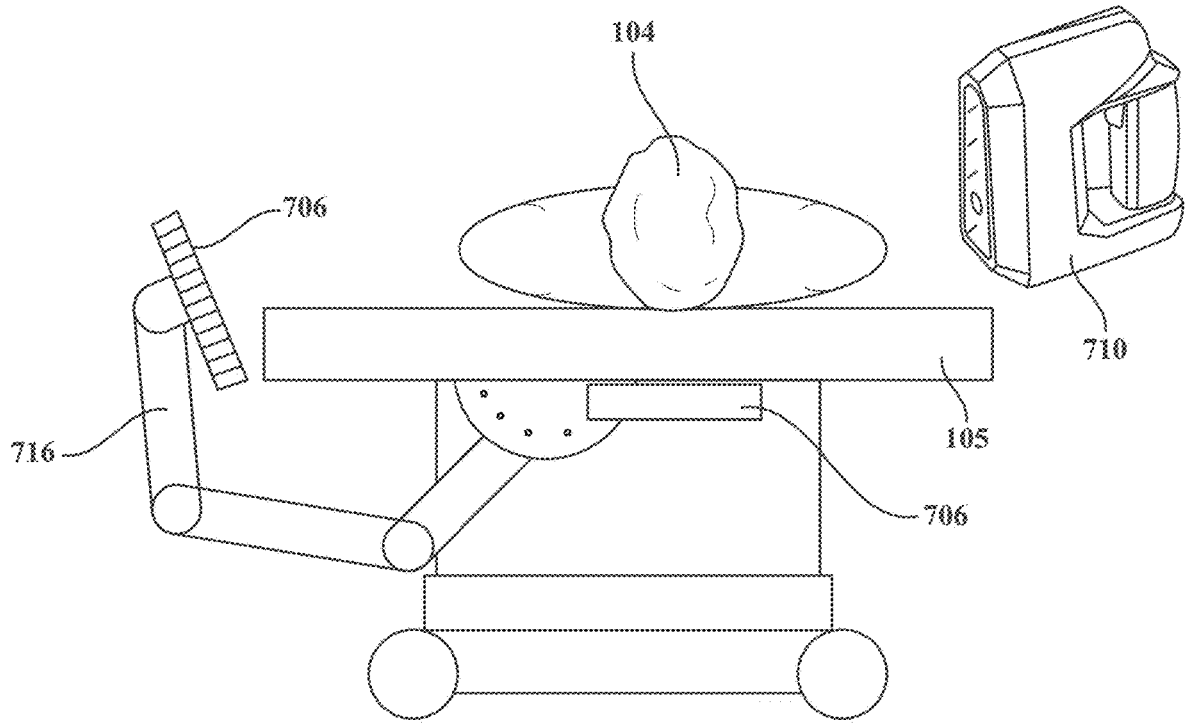
FIG. 12B illustrates additional arrangements of the imaging system where a sensor can be configured to capture lateral views by moving above a plane of the table.

FIG. 12B illustrates a variation where an emitter 710 can apply energy to a sensor/detector 706 that is configured to move as discussed herein, but can also move to enable a lateral image. In the illustrated variation, the sensor/detector 706 moves outside of the center X axis of the table 105 to capture lateral views of the patient 104. However, variations of the sensor 706 can include configurations where the table is non-planar and is configured to receive the sensor 706 above a plane in which the patient is positioned. FIG. 12B also illustrates an additional concept where multiple detectors 706 are used as described herein. In such a variation, the sensors 706 would be moved as described herein, but the sensor having the best operational alignment would be used to generate a signal.

Safety Lockout Procedures

Figure 14:
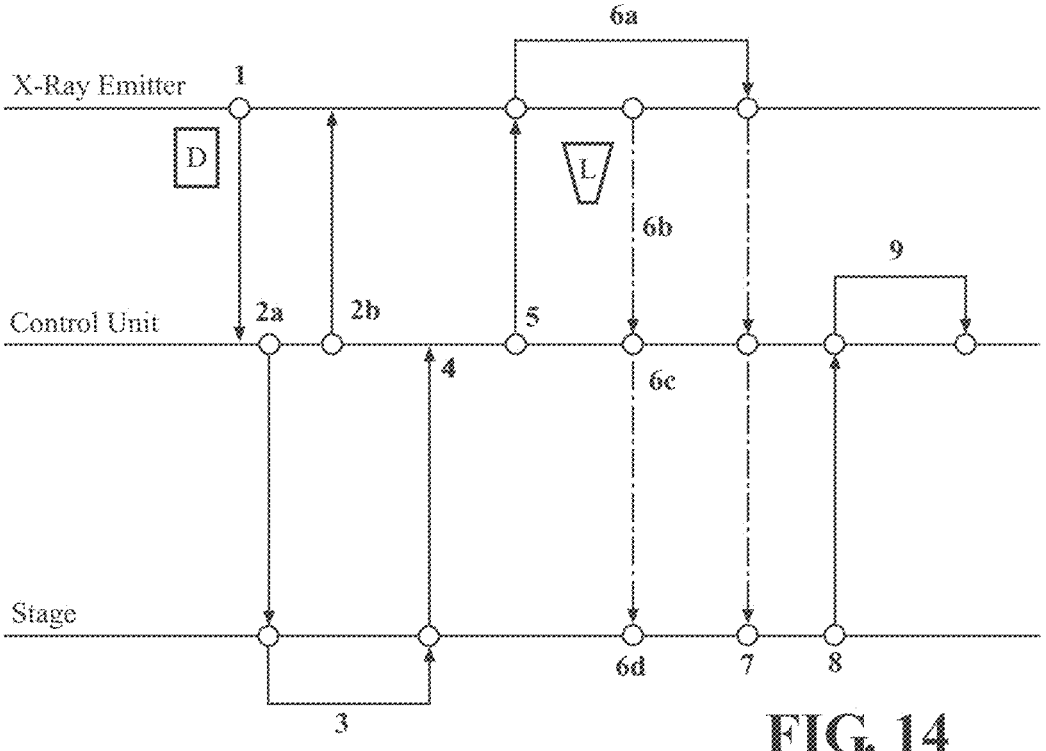
FIG. 14 illustrates a safety lockout of the capture stage based upon the disposition of the emitter.

Just as it is important to limit emissions from the emitter to specific target distances, for a variety of reasons, both practical and certification, it is important to only fire the X-ray generator when the emitter is properly aimed at the capture stage. By preventing the X-ray generator from emitting photons while not pointed at the stage, the safety of the system is improved, and the performance of an emitter is increased. FIG. 14 illustrates the process by which the device manages the safety lockout of the emitter and captures an X-ray image, with the numbers corresponding to the numbers in FIG. 14:

1. User initiates the capture process by signaling through the emission device 110, typically by depressing a trigger. The emitter sends a data packet (D) to the controller containing the request for capture, the distance measurements (d1, d2, . . . ), and the angle of the emitter.

2a. The controller validates that the emitter is in a safe orientation.

2b. If the controller discovers that the emitter is not in a safe, valid orientation, the controller sends an error message to the emitter. This prevents the emitter from firing and signals to the user that there is a problem.

3. The stage positions the sensor in accordance with the position of the emitter. The stage will tilt the sensor so that it is in the correct orientation to capture a clear image. The orientation will be as close to the complementary angle of the emission as possible.

4. The stage then sends a confirmation message to the controller after the position has been established.

5. The controller forwards the start message to the emitter. The emitter will then execute any additional safety or preparation tasks. If the emitter believes the environment is safe to fire, the emitter will then fire the X-ray.

6a. The emitter fires a pulse of X-ray photons at the stage for the requested amount of time.

6b. During the emission of the X-ray photon stream, the emitter constantly streams any updates to the position and angle to the central controller.

6c. The controller records these positional updates and relays them to the stage.

6d. The stage will rapidly and constantly update the position and angle of the sensor to optically stabilize the X-ray image.

7. The sensor captures the emission of X-ray photons from the emitter and builds an image.

8. Upon completion of the X-ray emission, the sensor relays the data to the control unit.

9. The control unit then cleans up the image from the sensor using a variety of known optical enhancement techniques. If applicable, the control unit will leverage the stored movement data from the emitter to further enhance the output.

The above process allows the emitter to ensure that the emission will be directed at the sensor and the stage, as opposed to any other arbitrary target. By moving the sensor into place below the emission target, the user can create a resolute, flexible image of the exact desired portion of the subject without having to reposition the subject.

Figure 15:
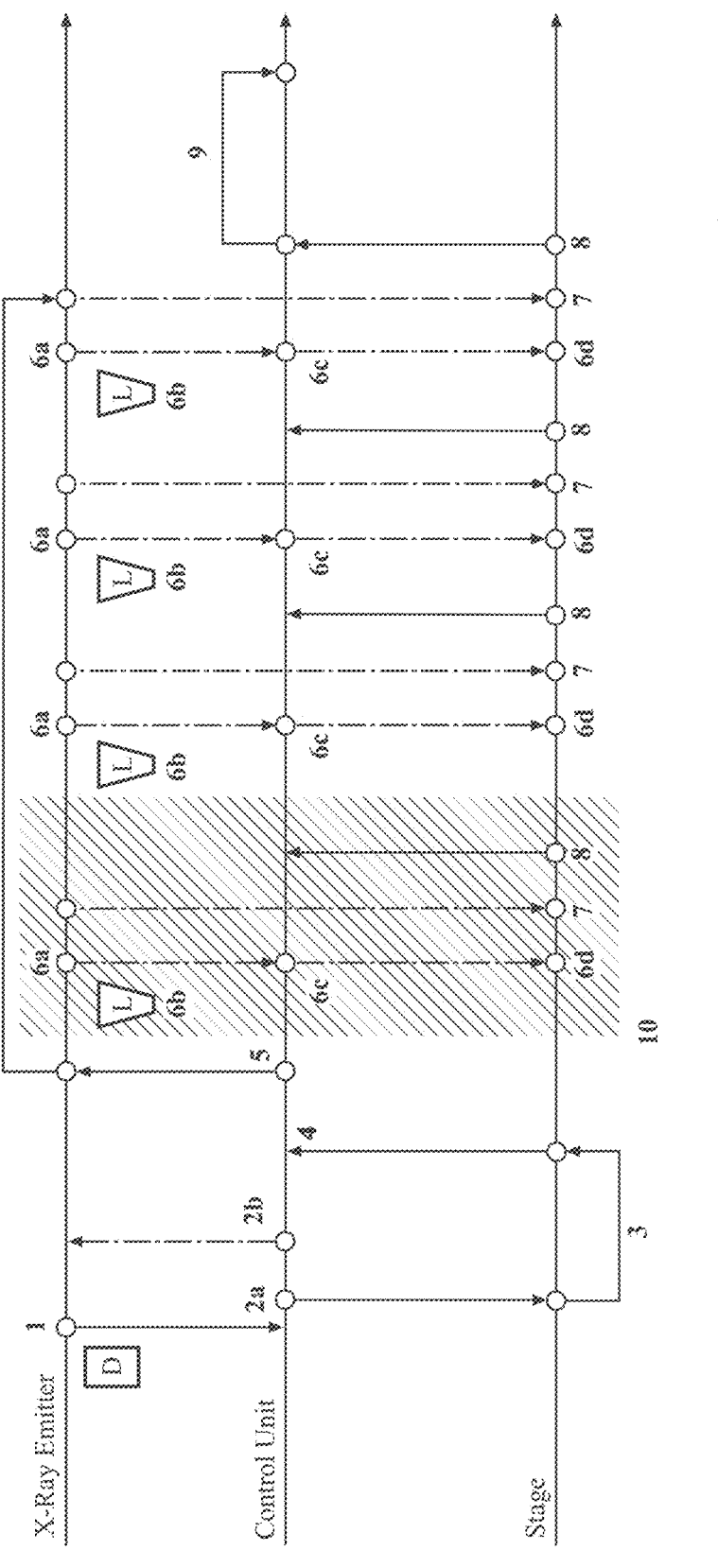
FIG. 15 illustrates the capture of a fluoroscopic image.

FIG. 15 illustrates the process by which the device captures a fluoroscopic image. The process for capturing a fluoroscopic image is very similar to capturing a static X-ray image; however, the fluoroscopic process will repeat several emissions and image captures to create a moving image. The process to ensure the safe emission as well as capture the fluoroscopic image, with the numbers corresponding to the numbers in FIG. 15:

1. User initiates the capture process by signaling through the emission handle, usually by depressing a trigger. The emitter sends a data packet (D) to the controller containing the request for capture, the distance measurements (d1, d2, . . . ), and the angle of the emitter.

2a. The Controller validates that the emitter is in a safe orientation.

2b. If the Controller discovers that the emitter is not in a safe, valid orientation, the controller sends an error message to the emitter. This prevents the emitter from firing and signals the user that there is a problem.

3. The stage positions the sensor in accordance with the position of the emitter. The stage will tilt the sensor so that it is in the correct orientation to capture a clear image. The orientation will be as close to the complementary angle of the emission as possible.

4. The stage then sends a confirmation message to the controller after the positioning.

5. The controller forwards the start message to the emitter. The emitter will then execute any additional safety or preparation tasks.

In the fluoroscopic mode, the emitter will repeat the following steps while the emitter device continues to request additional fluoroscopic frames, as follows:

6a. The emitter fires a pulse of X-ray photons at the stage for the requested amount of time.

6b. During the emission of the X-ray photon stream, the emitter constantly streams any updates to the position and angle to the central controller. If at any time during the fluoroscopic process, the operative stage detects that the emission is not aimed at the stage, the stage will send a termination signal to the emission device and skip directly to step 9.

6c. The controller records these positional updates and relays them to the stage.

6d. The stage rapidly and continuously updates the position and angle of the sensor to optically stabilize the X-ray image.

7. The sensor captures the emission of X-ray photons from the emitter and builds an image.

8. The sensor immediately transfers the image to the control unit. At this time, a brief cleanup process is executed, and the image is displayed on the external viewing device. This fluoroscopic frame is saved to memory.

The constant repetition of this process creates a moving image on the external display. The process will repeat until the user releases the trigger of the emission device.

9. Once the user releases the trigger of the emission device, the control unit "cleans up" the stored frames from the sensor using a variety of known enhancement techniques. If applicable, the control unit will also apply any stored movement data from the emitter to further enhance the output. The control unit will then combine the fluoroscopic frames into a single video for repeated playback.

The above process allows the user to see a live fluoroscopic view of the subject in real-time. By storing the images and reprocessing after the capture is complete, the device can create a high-quality, single fluoroscopic video for display and review at a later time.

Self-Adjusting Collimator

As noted above, the systems of the present disclosure allow for moving an emitting apparatus to a location relative to the object and determine a position of the emitting apparatus relative to at least one position tracking element where the at least one position tracking element measures a distance between the emitting apparatus and the object and preventing emitting energy until the distance is less than a pre-determined distance. Variations of the systems described herein can use a self-adjusting collimator that optimizes a profile or boundary of the emission onto the working surface of a sensor. As with other variations described herein, these systems can relay the position of the emitting apparatus to a motor system that adjusts an imaging sensor into an operative alignment with the emitting apparatus, where relaying the position of the emitting apparatus includes using the emitting apparatus to both provide an orientation data of the emitting apparatus and determine a distance from each of the plurality of tracking elements. However, the use of a self-adjusting collimator allows for automatic maximization of an emission profile on the imaging sensor.

To illustrate the benefit of an adjustable collimator, FIG. 20 illustrates a representation of an X-ray emitter 110 directed towards a table 114 having an imaging sensor (not shown) located therein. The perimeter of the working area 116 of the imaging sensor is shown to illustrate the area that will produce an image upon exposure to an X-ray emission. As shown, a profile of an X-ray emission 120 from X-ray emitter 110 extends beyond the perimeter of the working area 116 of the imaging sensor, causing the X-ray emitter to be out of operative alignment with the sensor. In such a case, the system as described herein will not permit firing or initializing of the X-ray emitter 110. The illustration of FIG. 20 is intended to illustrate a concept of the system being out of operative alignment. As noted herein, the imaging sensor can be coupled to a motor system to permit movement of the sensor into alignment with the emission profile 120. Alternatively, the table (or operating surface) 114 can include a plurality of position tracking elements (not illustrated in FIG. 20) that allow determination of the position and distance of the emitter 110 relative to a non-moving sensor or the sensor's working area 116.

FIG. 21A represents a situation in which an emission profile 120 extends beyond the sensor 116 such that the emitter is not in operative alignment with the sensor 116. For purposes of illustration, the sensor 116 shown in FIGS. 21A and 21B, is stationary, and tracking elements 118 permit the system to determine the relative location, orientation, and distance of the emitter (not shown) relative to the sensor 116. Also, the emission profile 120 is illustrated as a representation of a boundary of the emission provided by the emitter. For purposes of illustration, the profile 120 illustrated is a profile that would occur if an axis of the emitter is perpendicular to the sensor 116.

As noted herein, if the system cannot establish operative alignment given the condition shown by FIG. 21A, the operator will be prompted to adjust the position of the emitter. In some variations, the system can provide feedback, such as an audible or visual indicator of non-alignment. FIG. 21B shows a situation after repositioning of the emitter such that the emission profile 120 falls within the boundary of the sensor 116. However, as shown, this emission profile 120 is not maximized to the dimensions of the sensor 116. Failure to maximize the emission profile 120 relative to the sensor can require the operator to take additional radiological images of the subject to adjust for a smaller profile.

Figure 22A:
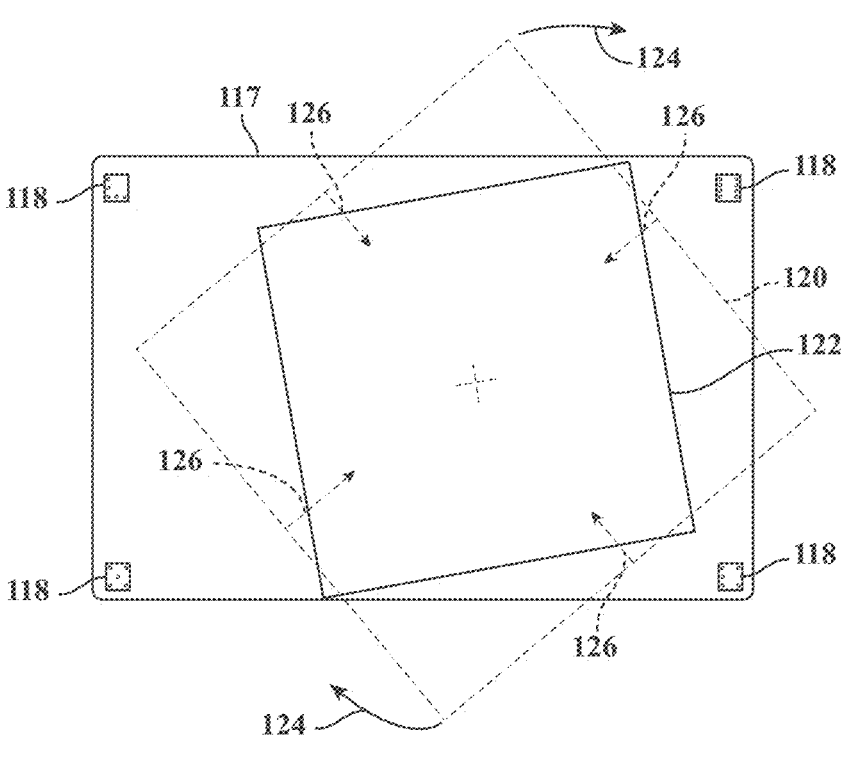
FIGS. 22A and 22B illustrate an example of the effect of an adjustable collimator to produce an adjusted emission profile that is scaled and/or rotated to remain within the perimeter of an imaging sensor.

FIG. 22A illustrates the effect of an adjustable collimator. Again, for purposes of illustration, the emission profiles shown represent illumination by an emitter that is perpendicular to a sensor. FIG. 22A shows an unadjusted emission profile 120 that would ordinarily be considered out of operative alignment with the imaging sensor 116, given that a portion of the emission area bound by the profile 120 falls outside of the sensor 116. However, a variation of the system described herein will rely on the position tracking elements 118 as well as components affixed to the emitter (as described above) to determine positional information, such as an orientation of the emitter, as well as a distance between the emitter and the sensor 116. The system will use the positional information to adjust a collimator on the emitter to rotate and/or scale emission by the emitter to produce an adjusted emission profile 122. As shown, in this variation, the adjusted emission profile 122 is reduced in size (denoted by arrows 126) and also rotated (denoted by arrows 124) to scale the emission profile 120 into an adjusted emission profile 122 that maximizes an exposure onto the imaging sensor. It is noted that the adjusted emission profile can be scaled or rotated as needed. Moreover, variations of the system will produce an adjusted profile during real-time movement of the emitter relative to the sensors 118.

Figure 22B:
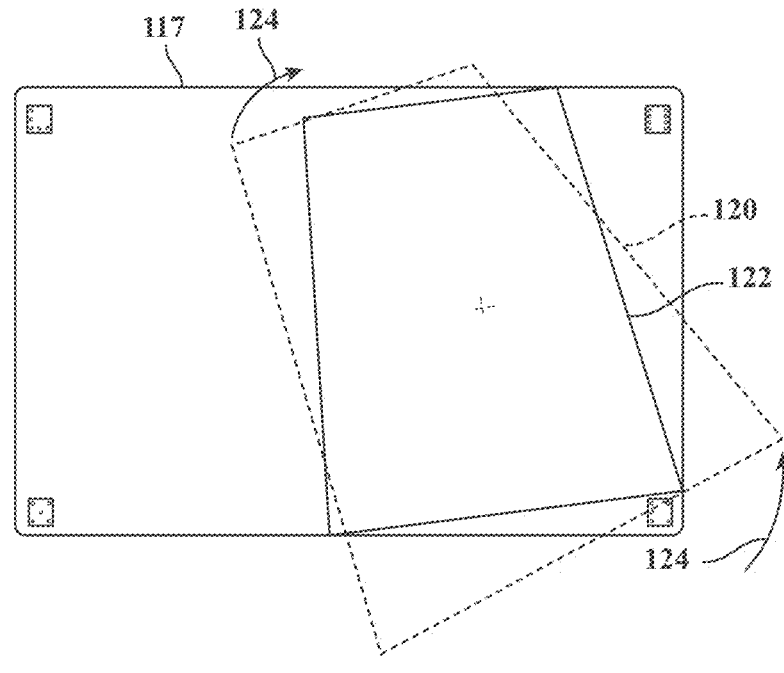

FIG. 22B illustrates an unadjusted emission profile 120 along with the adjusted emission profile 122, where in both cases, the profile resembles an isosceles trapezoidal shape due to an axis of the emission path not being perpendicular or normal to the sensor 116. However, in this variation, the system uses the positional information to produce an adjusted profile 122 that maximizes an exposure area on the image sensor 116.

While the variations disclosed herein rely on tracking elements 118 as well as sensors within the emitting unit (as described herein). Variations of the system that produce an adjusted emission profile can also be used with positional data that is derived from external cameras, sensors, or mechanical supports to determine relative movement between an emitting apparatus and an imaging sensor.

Figure 23:
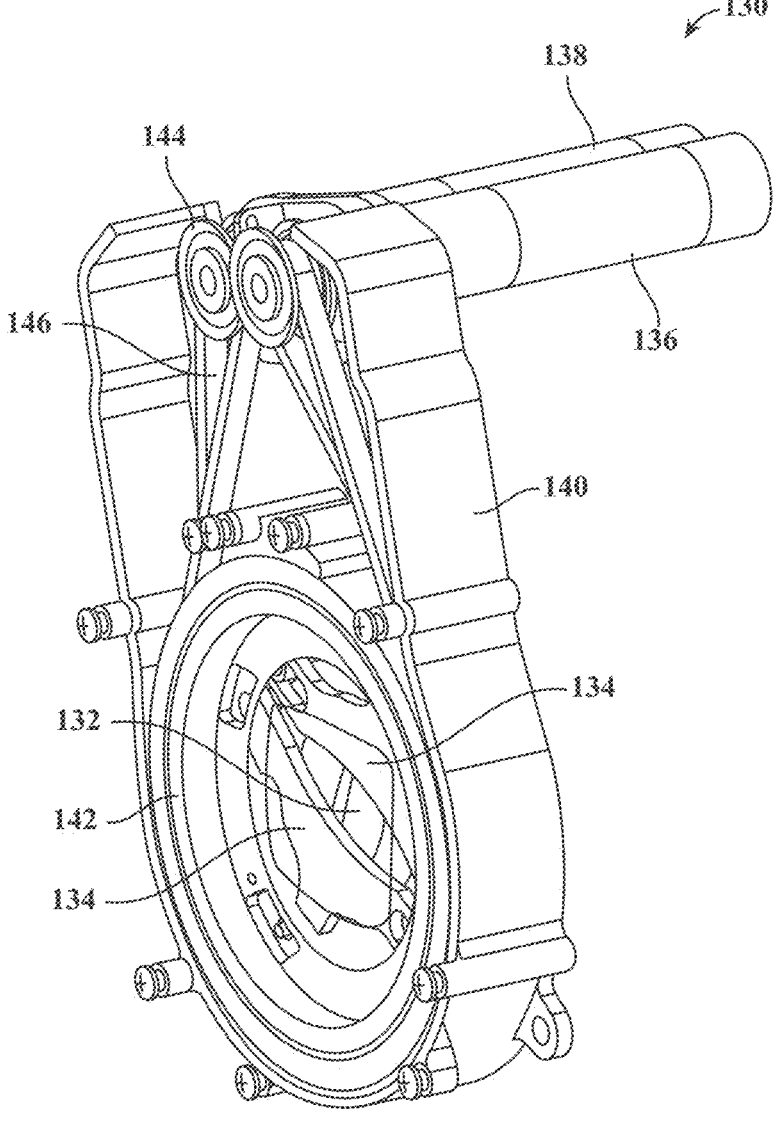
FIG. 23 shows a variation of an adjustable collimator that can be used in or with an emitting apparatus.

FIG. 23 shows a variation of an adjustable collimator 130 that can be used in or with an emitting apparatus (not shown in FIG. 23). As illustrated, the adjustable collimator 130 can rotate and/or scale an aperture or emission window 132 to produce an adjusted emission profile upon an imaging sensor (as discussed in FIGS. 20 to 22B). This variation of the adjustable collimator 130 uses a number of blades or leaves 134 that can move and rotate to adjust an orientation of the aperture 132. The blades 134 prevent passage of the emitted energy such that energy is limited to pass through the aperture or emission window 132.

The movement and rotation of the blades can be driven by any number of motors or drives. In the variation shown, the adjustable collimator 130 includes a motor assembly having a first drive 138 coupled to a proximal slewing bearing 152 and a second drive 136 coupled to a distal slewing bearing. The drives 136 and 138 adjust the rotation of the blades 134 as well as a sizing of the aperture 132. For example, rotation of the motors 136 and 138 in opposite directions causes rotation of the slewing bearings in the opposite direction and produces movement of the blades 134 to cause opening/closing of the aperture 132. In the example shown, if the first drive 138 moves in a clockwise direction and the second drive 136 moves in a counterclockwise direction, then the blades 134 will move towards each other, causing a size of the aperture 132 to decrease. Likewise, if the first drive 138 moves in a counter-clockwise direction and the second drive 136 moves in a clockwise direction, then the blades 134 will move away from each other, causing a size of the aperture 132 to increase. If the drives 138 and 136 move in the same direction, this will cause rotation of the proximal and distal slewing bearings 150 and 152 in the same direction, which will cause rotation of the blades, which causes rotation of the aperture 134.

The adjustable collimator 130 maintains an aperture 132 having a near-square shape since all of the blades 134 move to adjust the size of the aperture. Additional variations of the device can include any number of additional motors or actuators to also control an angular orientation of the blades. In such a case, the aperture 134 is not limited to a square profile and can assume an isosceles trapezoidal shape. Such a feature can assist in maintaining a square emission profile (such as that shown in FIG. 22A) regardless of the orientation of an axis of the emission energy to the imaging sensor.

The variation of an adjustable collimator 230 shown in FIG. 23 also includes a chassis or housing 140 that houses the drive mechanism (e.g., bearings, pulley 144, belts 146, etc.) that translates the movement of the gears 144 driven by motors 136, 138 into rotation and movement of the blades. Furthermore, the adjustable collimator 230 will include any number of positioning tracking systems that enable the system to maintain information regarding a size and rotational orientation of the aperture. For example, a first movable disk (or encoder wheel) 142 is shown as part of an optical encoder system that can use any conventional light source, sensor, mask, and photosensor (e.g., a photodiode).

Figure 27:
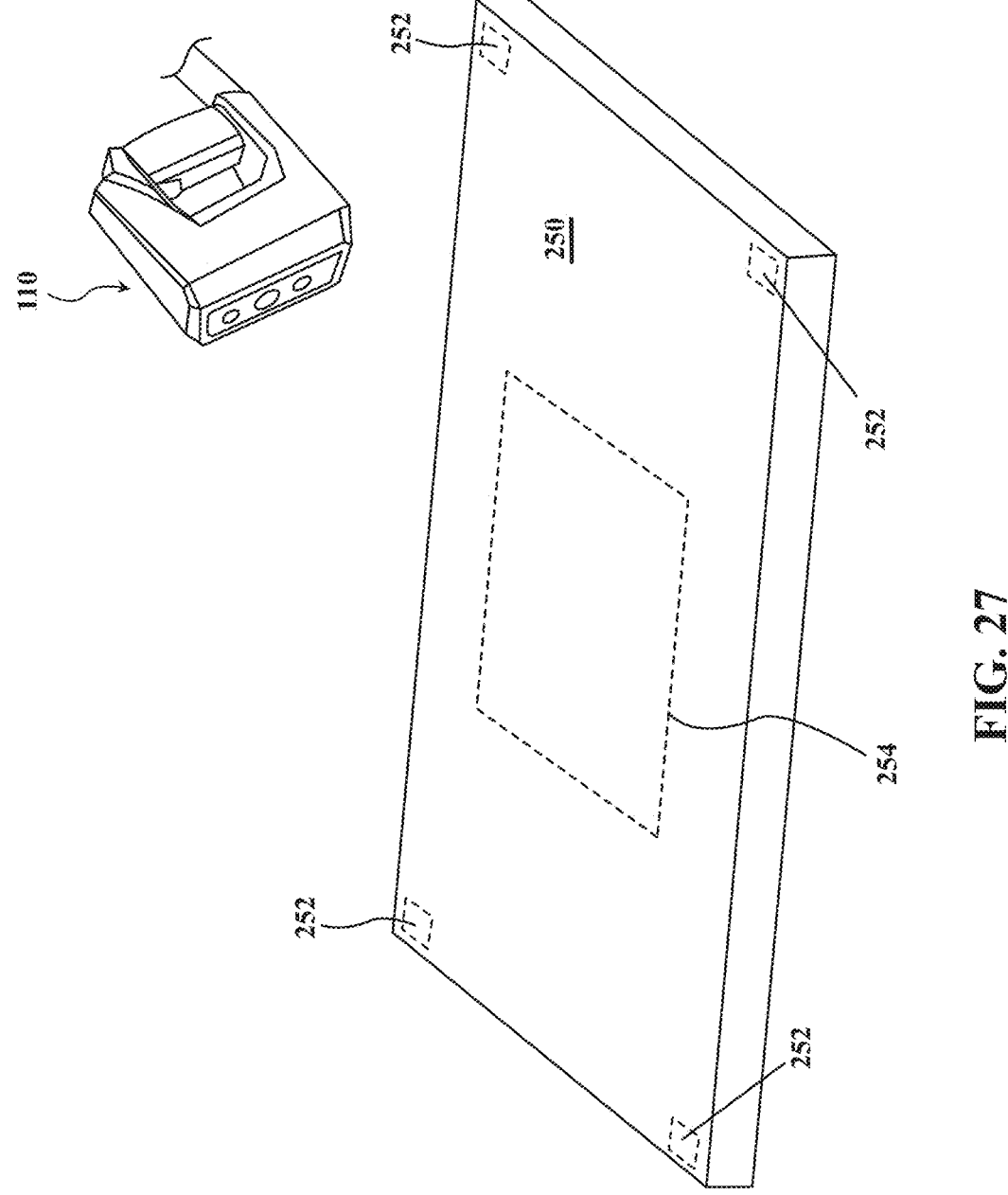
FIG. 27 shows an additional variation of an X-ray system using non-line-of-sight-tracking-elements such as electromagnetic tracking sensors.

FIGS. 27 and 28A-28B illustrate another aspect in which a radiological system having a sensor configuration as described herein can improve the quality of an X-ray or fluoroscopic capture.

The quality of an X-ray or fluoroscopic capture is related to a number of physical attributes of the subject. These elements dictate a set of technique factors (e.g., power, current, time, etc.) that control the emission characteristics of the radiation source/emitter. It is the responsibility of the device operator to set these factors in such a combination that the individual viewing the radiological image can identify the necessary visual elements without exposing the subject to excess radiation.

Setting these technique factors can be complex. In order to relieve the operator of the burden of setting these techniques manually, existing fluoroscopic devices have implemented an automatic process. The typical approach uses a software or a hardware dose detector on the plate that gradually fills as radiation is added to the exposure. This conventional approach has a number of problems.

One major issue with the conventional approach is movement. Because the radiation is exposing the subject for an extended time period, any movement whatsoever, either in the subject, the operator, the machine, vascularity inside the subject, etc., creates motion artifacts that severely degrade the image.

Another issue is that penetration requirements are not known before the exposure; therefore, as the source emits radiation at a given power level (kV), frequently, there is not enough penetration to render an image. This failure to render an image exposes the patient, operator, and staff to radiation without producing any useful radiological image. In such a case, these individuals are exposed to excess radiation that does not serve any clinical purpose.

Innovation in the fluoroscopic device space, including but not limited to the systems described herein, creates a new generation of machines with complex sensor arrays capable of directly measuring a number of the physical elements required for exposure calculation.

By utilizing these sensors across the full spectrum of devices and subjects, as well as robust machine learning techniques, it is possible to compute the necessary techniques before exposure, eliminating motion artifacts and creating an outstanding capture, all while reducing dose.

The following descriptions provide exemplary details of the invention in order to provide an understanding of the invention. Small engineering adjustments could be employed to practice the invention without employing these specifics. While the invention is described for use in X-ray imaging for surgical purposes, it could be used in other medical applications, including but not limited to general medical imaging, veterinary, and bone densitometry. It could be used for non-medical applications such as industrial imaging, metal fatigue inspections, weld-inspection, for security inspections, and the like.

Figure 24:
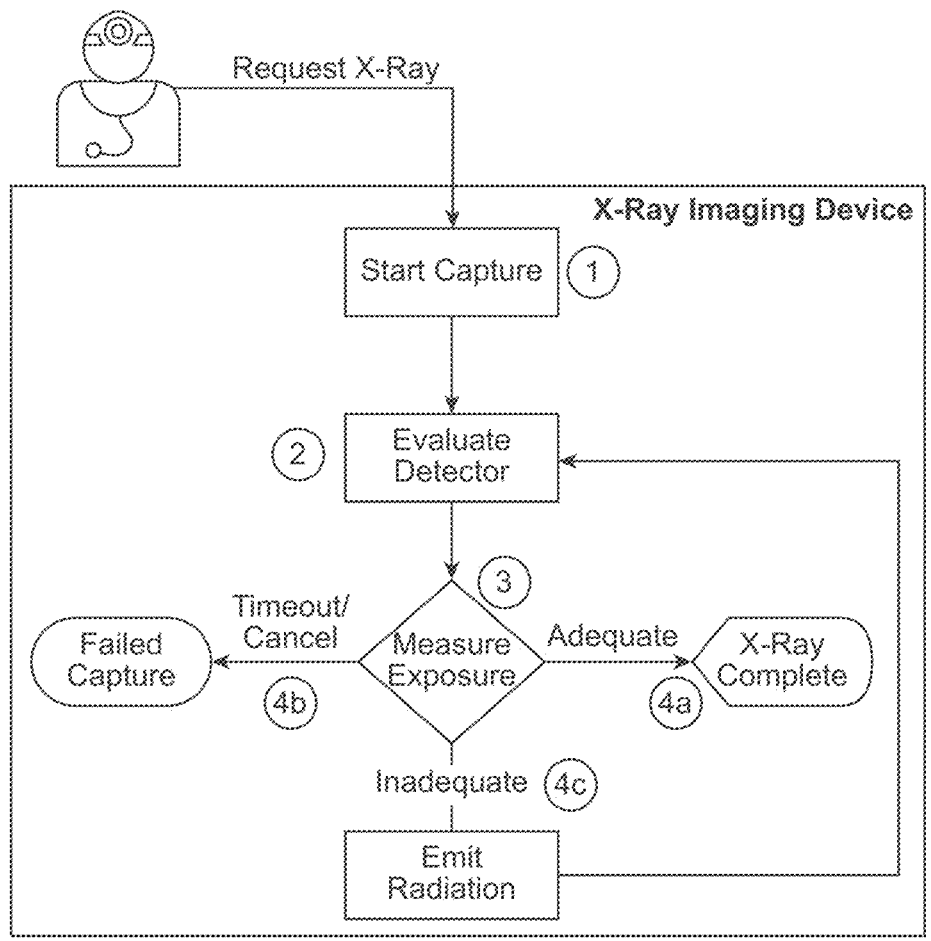
FIG. 24 illustrates an example of a traditional automatic exposure process.

FIG. 24 shows a diagram of an example of a conventional methodology for automatic X-ray exposure process. The doctor or operator begins the exposure (step 1) by requesting the X-ray be taken. The X-ray device will then evaluate the detector (step 2), tracking the amount of radiation received on the imaging sensor plate. An internal measurement of X-ray machine will determine if this energy is a sufficient amount of exposure to generate an image (step 3). If the device determines that an adequate amount of radiation is collected (step 4a), it will deem the exposure complete and display the X-ray. If the user cancels the X-ray or the dose has been accumulating for too much time, the machine will cancel the exposure (step 4b.) Otherwise, (step 4c), the device will continue to emit radiation, returning back to the evaluation step until the image is created, time runs out, or the user cancels the exposure.

The traditional process has a number of drawbacks. The two largest are that: exposure begins without a guarantee that an image will appear, and that the time taken to evaluate the exposure introduces movement artifacts in the final image, creating an unusable X-ray. In either case, the patient, operator, and staff are exposed to unnecessary radiation, which is a major safety hazard.

Figure 25:
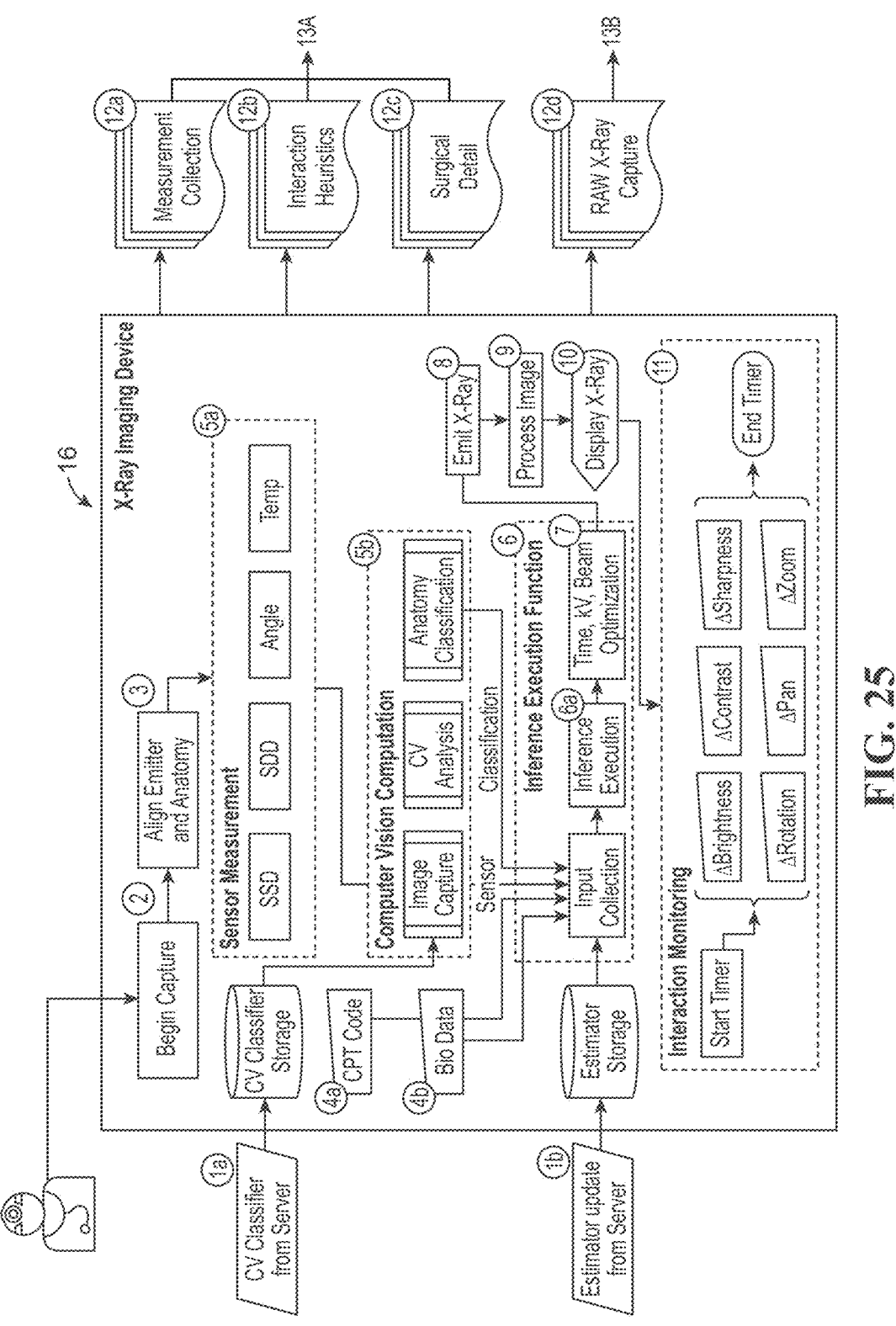
FIG. 25 illustrates an improved system that relies upon one or more databases to provide machine learning for determination of exposure settings for a radiological image.
Figure 26:
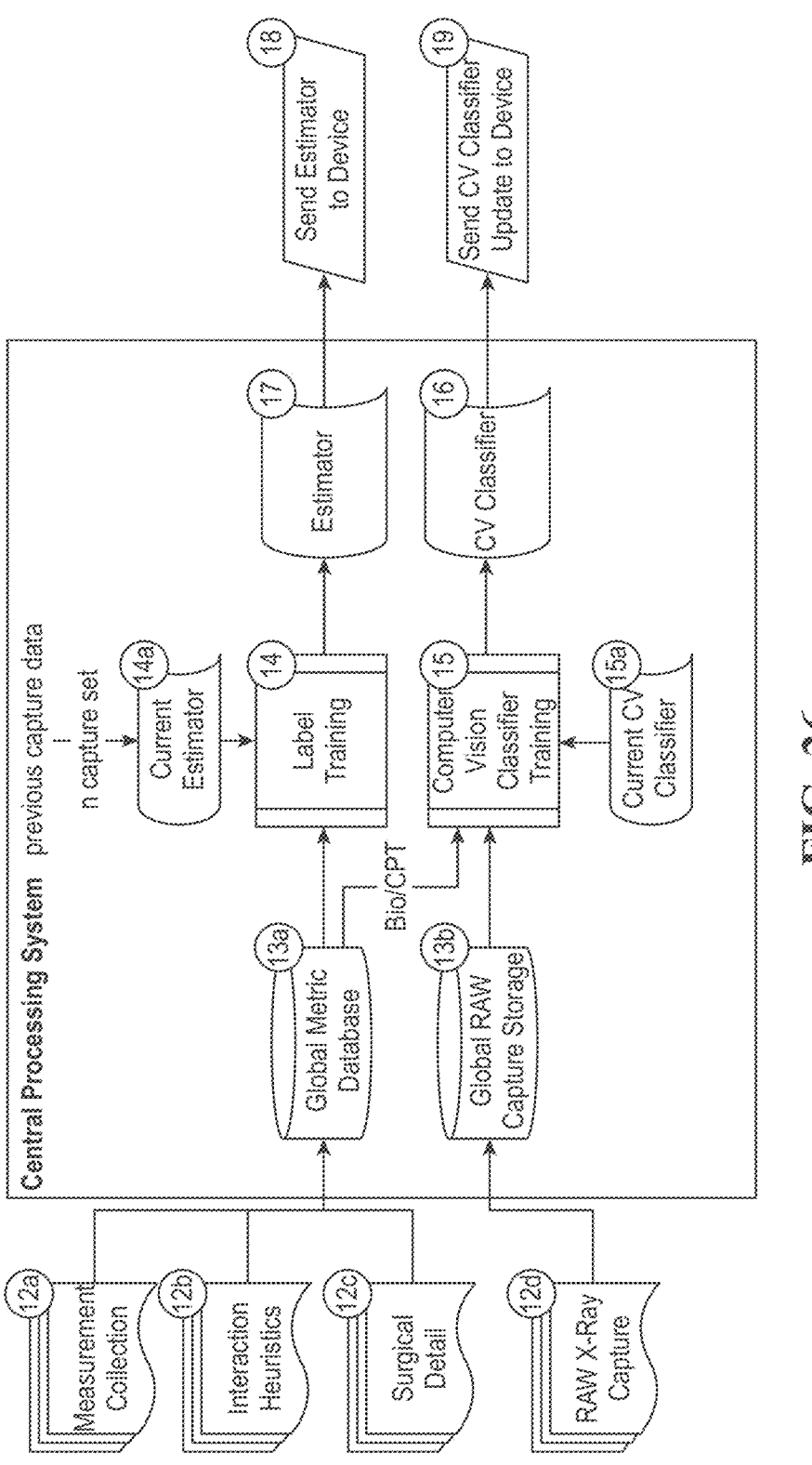
FIG. 26 illustrates a process of improving the automatic exposure process and databases using feedback from the systems described herein.

FIGS. 25 and 26 illustrate an improved approach over the conventional methodology described in FIG. 24. The improved approach can determine the optimal technique factors to create a resolute and effective radiological image without exposing the operator, staff, and patient to unnecessary or excessive radiation. By utilizing a radiological imaging device with a comprehensive sensor array and an enterprise-wide application of machine learning techniques, the system 20 can calculate and refine the techniques before any radiation is emitted. This allows an operator to precisely align the device and understand if the machine is capable of imaging the anatomy.

FIG. 25 illustrates an example of how statistical data can be compiled for use in the imaging process of FIG. 25. In practice, a number of statistical models are transmitted to the system 20 from a central server (shown in FIG. 26). These models, referred to as the Computer Vision Classifier (1a) and the Estimator Update (1b), are stored locally on the machine and ready for use prior to the operator requesting the exposure.

Turning to FIG. 25, the process can begin with the operator initiating the capture (2). The operator then uses the positioning system of the device to align the emitter and anatomy (3), completing the safety checks, then executing the automatic technique detection (as described above). Depending on the exact topography of the X-ray system, CPT Code information (4a) and or Biometric Information (4b) may be entered by an operator or extracted from another system by automatic means.

As the system prepares to emit the energy for either X-ray or fluoroscopic capture, two concurrent measurement collections are happening: on-device sensor collection (5a) and computer vision classification (5b).

The sensor collection uses the array on the device to collect a multitude of input parameters, including, but not limited to, source-to-skin distance (SSD), source to detector distance (SDD), angle of incidence, ambient, X-ray tube and device temperature, etc. These parameters are all fed into the inference execution function (6).

The computer vision classifier utilizes the imaging camera on the device to capture pictures of the subject anatomy. These images are passed into the CV analysis function, using the captured images as well as the CV Classifier data that is stored locally on the device provided by the central server. These processes make a determination about the subject of the capture, and passes that recommendation to the Inference Execution Engine.

Once the inputs are collected from the device's various subsystems, those values, along with the Estimator Update provided by the central server, are run against the device's inference execution engine (6a). The output of that function family is the determined X-ray technique: time, kV, and beam current (7).

The device output is set to the computed values, radiation is emitted for the given settings (8), the image is captured and processed (9), and the image is displayed to the user. (10)

As soon as the X-ray is displayed to the operator, the system immediately begins monitoring the operator interaction in the Interaction Monitoring system (11). This system records every interaction the operator has with the image, which includes changes in brightness, sharpness, contrast, position, zoom, rotation, etc. The amount of time the operator spends examining the X-ray or fluoroscopic capture is also recorded.

In steps 12a-12d, the system will submit capture data to the central processing system. The submitted data includes the four major components of the capture: (12a) Direct Measurement Information, such as SSD, temperature, etc. (12b) interaction heuristics, such as the changes in brightness or the amount of time spent examining a capture. (12c) includes the surgical detail, such as the biometric information, any associated CPT code, as well as the computer vision captures and resulting classification output. (12d)

includes the raw capture data from the detector itself as well as capture associated information, such as machine details, software versions, etc.

This capture information is stored on the central processing system in respective databases 13a and 13b for future processing.

At a scheduled time, the central processing system will train the estimator labels (14) using a sophisticated regression analysis. By examining the statistical relationship between the sensor data, capture data, and surgical data across a large section of universally captured X-rays, as well as the results of the previous estimator generation (14a), the system can fit data to more accurate labels. The output of the training step is a new estimator (17).

Like the label training step (14), the X-ray and fluoroscopic capture data, surgical detail data, and classifier data will be trained using a classifier refinement process (15). This process uses the large capture cross-section from the huge number of input X-rays to create a more accurate classifier (16).

Depending on the topography of the X-ray machines in the field, the central processing system will transmit the new estimator (18) and classifier (19) to the devices as soon as possible. They will then load these updates into the device local storage (1a) and (1b) and apply the new algorithms to further enhance the accuracy and reduce the dose of the automatic exposure.

FIG. 27 shows an additional variation of an X-ray system using non-line-of-sight-tracking-elements, such as electromagnetic tracking sensors 252. Although the example of FIG. 27 shows 4 sensors 252, any number of sensors 252 can be used as required. While the system can operate with a single sensor 252, additional sensors can be used for redundancy. In operation, the electromagnetic sensors 252 generate an electromagnetic field to create a tracking space within a defined region (e.g., the operating tablespace 250) about a perimeter of the X-ray sensor 254. The emitter 110 includes one or more receivers that inductively couple with the magnetic field generated by the sensors 252. Since the sensors 252 allow for non-line-of-sight tracking of the emitter 110, the sensors 252 can be positioned within the working space 250. Alternatively, the sensors 252 can be visible, or their position can be marked on or around the working space 250. The ability of non-line-of-sight tracking allows for full-body imaging applications. Additionally, the non-line-of-sight tracking permits reducing the size of the structure housing the X-ray sensor 254. Any number of electromagnetic tracking field emitters and sensors can be used as an alternative or in addition to the tracking emitters discussed above.

Electromagnetic sensors and their operation are discussed in U.S. Pat. Nos. 4,054,881; 6,762,600; 6,624,626; 6,400, 139; 6,377,041; and 6,369,564, the entirety of each of which is incorporated by reference. Such electromagnetic tracking systems are available from Polhemus (Vermont, USA) and NDI (Ontario, Canada).

Electromagnetic tracking systems (EM systems) can be very sensitive to interference from prevailing metallic objects or inductive motors. Accordingly, variations of an X-ray system using an EM system will additionally include one or more inertial measurement units (IMUs). In use, the X-ray system with EM tracking starts in a calibrated state. This calibration is held over from previous use or comes calibrated directly from the factory. As the X-ray system is in use, tracking of the X-ray emitter relative to the X-ray detector is accomplished by both the EM sensors and any IMUs. Typically, one or more IMUs are placed in the X-ray emitter, and (optionally) an IMU placed in the X-ray detector. EM tracking and the differential positioning data supplied by the IMUs will generally line up. If at any point, both data sets do not align, the system can infer transient interference in the EM system and signal an error state. During this error state, the system can use the IMU data to smooth out any interference and generate a best-most-likely positioning state. Typically, this inference is sufficient to smooth the EM data and maintain system functionality. As the transient interference subsides, the IMUs data and EM sensor data will fall back into alignment.

In an additional variation, an X-ray system with EM tracking can use the X-ray emission to actively and continuously update the calibration. In such a case, collimation/beam angle of the X-ray emission from the emitter permits identification of the true position of the X-ray emitter when the emission was released through computer processing. The system can then use the true position calculated from the emission to determine if any offsets to the EM positioning system are required.

Figure 28:
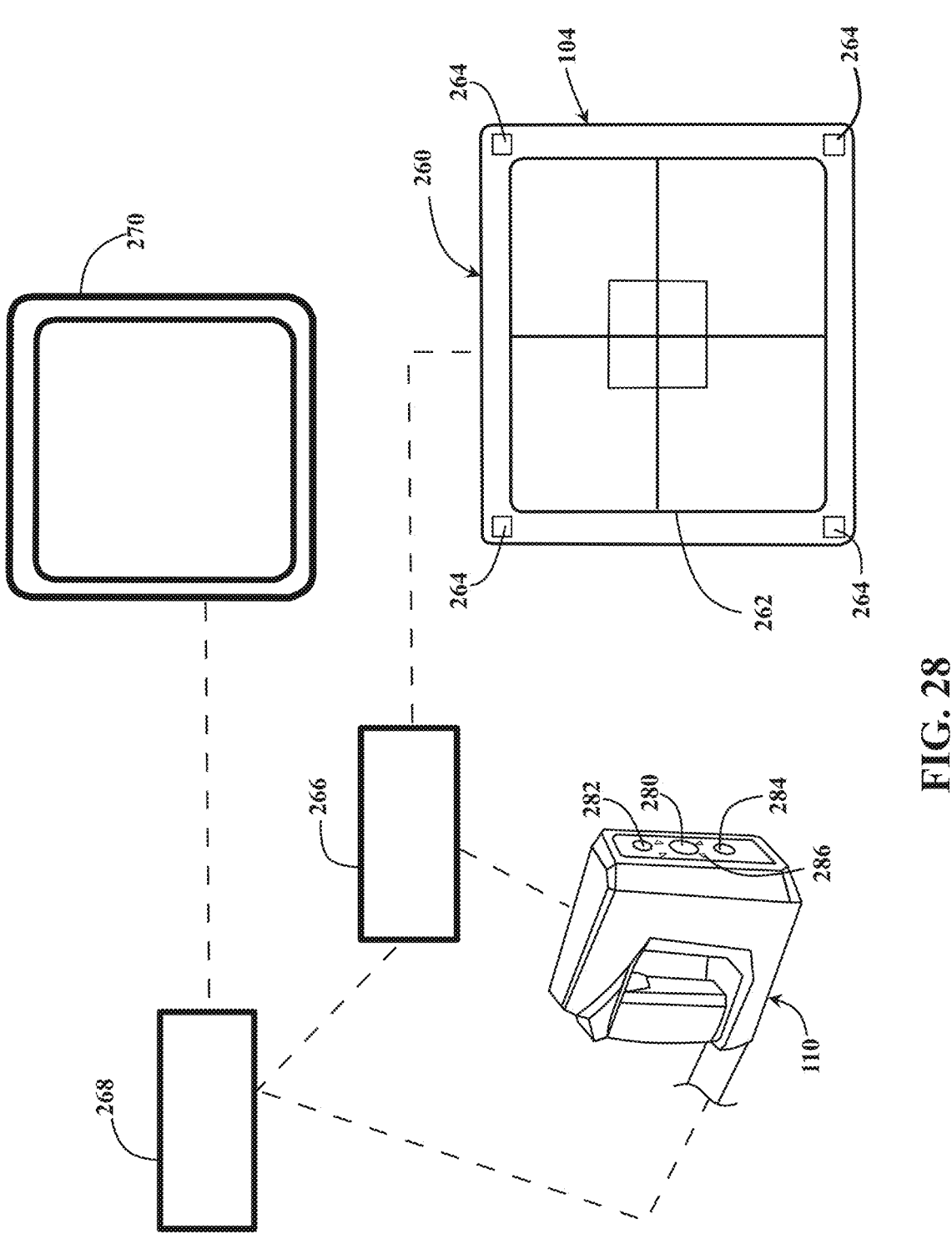
FIG. 28 illustrates another variation of an imaging system as described herein that uses a portable X-ray emitter and monitor to display one or more virtual images to assist in obtaining an X-ray image.

FIG. 28 illustrates another variation of an imaging system as described herein that uses a portable X-ray emitter 110. The X-ray emitter 110 can be free-standing or can be attached to a boom-type structure that allows for up to six degrees of freedom. As discussed above, the X-ray emitter 110 is configured with a positioning system using any number of position tracking elements 264 that are positioned around a perimeter of an imaging sensor 262 that receives an X-ray emission from the emitter 110 to produce an X-ray image. The imaging sensor 262 can be located in a housing 260 that comprises a working area for positioning of the object to be imaged. Alternatively, the sensor 262 can be positioned in a table structure or other structure as discussed above.

The position tracking elements 264 communicate with an X-ray positioning control system 266 that is configured to determine the relative location of the image sensor 262 and emitter 110. The X-ray positioning system 266 can be any of a variety of positioning systems, including but not limited to the positioning system as described herein, and can use line-of-sight emitters, non-line-of-sight sensors, or a combination thereof.

The system shown in FIG. 28 also illustrates the emitter 110 as having one or more cameras 282 adjacent to an emitter window 280. Variations of the system can include an emitter 110 as having dual stereoscopic cameras 282, 284 positioned about the emitter window 280. Alternatively, a single camera 282 or 284 can be used. As shown, the emitter 110 can optionally include lidar sensors 286 for additional positioning, imaging, and depth-sensing functionality, as well as any additional sensors disclosed herein.

The camera(s) 282 and/or 284 transmit signals to a processing unit 268, which produces an image of the field of view from the emitter 110 using the camera signal. The processing unit 268 is also configured to use the positioning data from the positioning system controller 266 to generate a first virtual representation of the imaging sensor 262 and overlays this image onto the image of the field of view from the emitter 110 as discussed below. The image and the first virtual representation of the imaging sensor 262 can be viewed on one or more display units 270. In one variation, the display unit 270 comprises a screen on a portion of the emitter 110. Alternatively, or in combination, the display unit can be a monitor within the examination area. In addition, the processing unit 268 can allow for broadcasting of the virtualized image to allow for remote viewing of the virtualized image. In additional variations, the X-ray positioning system 266 can be combined with the processing unit 268.

Figure 29:
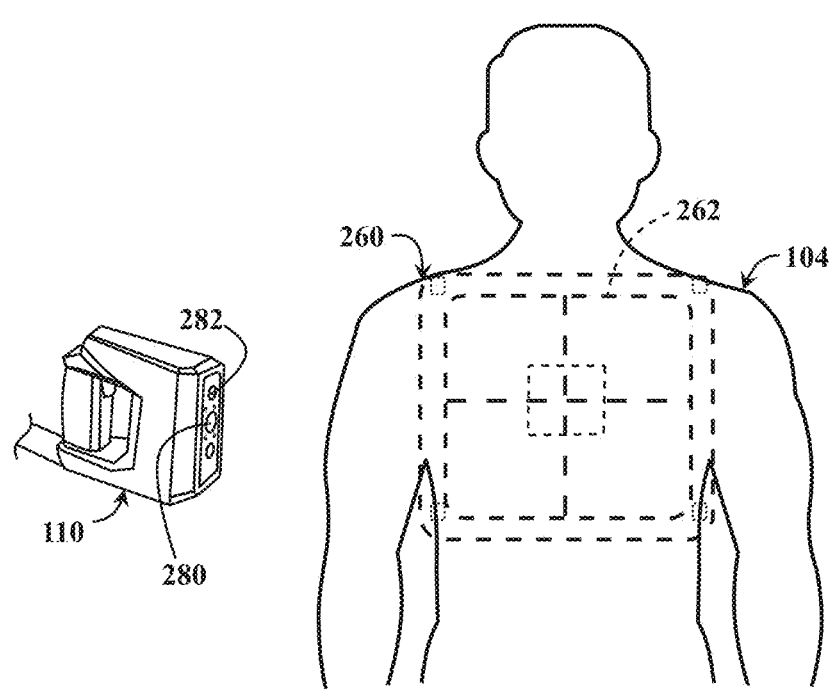
FIGS. 29 and 30 illustrate the initial stages of an attempt to capture an X-ray image of an individual patient that is adjacent to an image sensor of an obscured image sensing housing.
Figure 30:
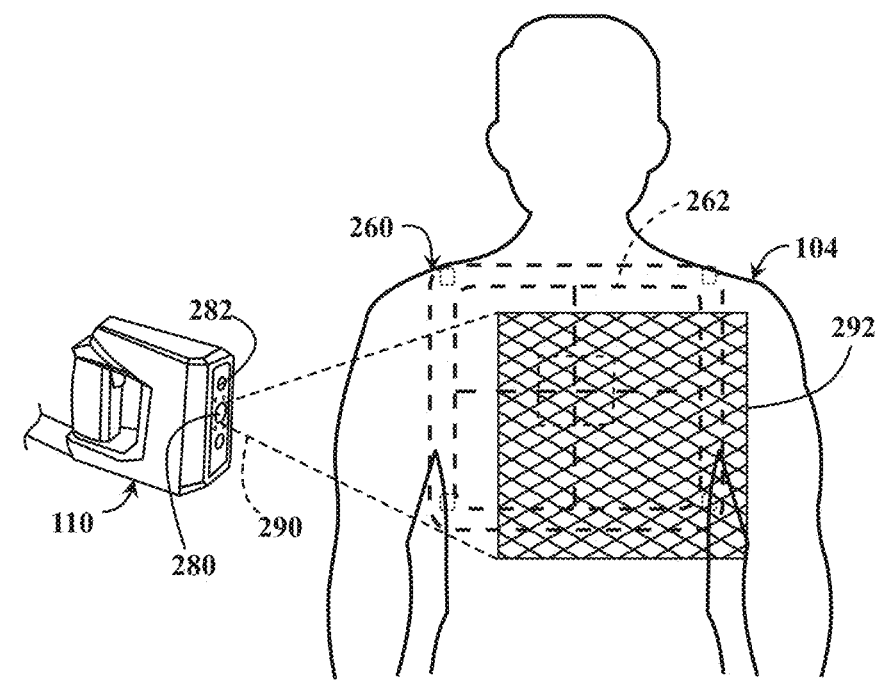

FIGS. 29 and 30 illustrate initial stages of an attempt to capture an X-ray image of an individual patient 104 that is adjacent to an image sensor 262 of an image sensing housing 260 where the individual patient 104 obscures a majority of the housing 260 and/or image sensor profile 262. The illustration shown is for explanatory purposes as the same principles apply if the image obtained was a body portion (e.g., a leg, shoulder, torso, etc.) where the body portion obscures the image sensor 262 such that an operator of the X-ray cannot visually confirm alignment of the body/body portion on the housing 260 with the image sensor outline 262. FIG. 30 illustrates where a projection of an X-ray emission 290 would produce an emission projection area 292 on the individual 104. However, in some variations, the X-ray system allows the operator to determine an outline of the projection area 292 using a light-field generated by the emitter 110. This allows the operator to visualize the area of the X-ray emission without generating X-ray radiation.

As shown in FIG. 30, because the X-ray detector housing 260/sensor 262 is obscured by the patient's torso 104, the operator can inadvertently incorrectly position the X-emitter 110 such that the emission projection area 292/light field is, unknowingly, misaligned with the image sensor 262. This misalignment results in an X-ray image having a compromised field-of-view, the projection area 292. Positioning of the camera 282 adjacent to the emitter window 280 permits the camera to obtain a similar field-of-view as the emitter window 280. In variations of the system, the camera(s) 282 can use image stabilization or actuators to shift a perspective of the camera image so that the camera image is always displayed normal to the image sensor.

Figure 31:
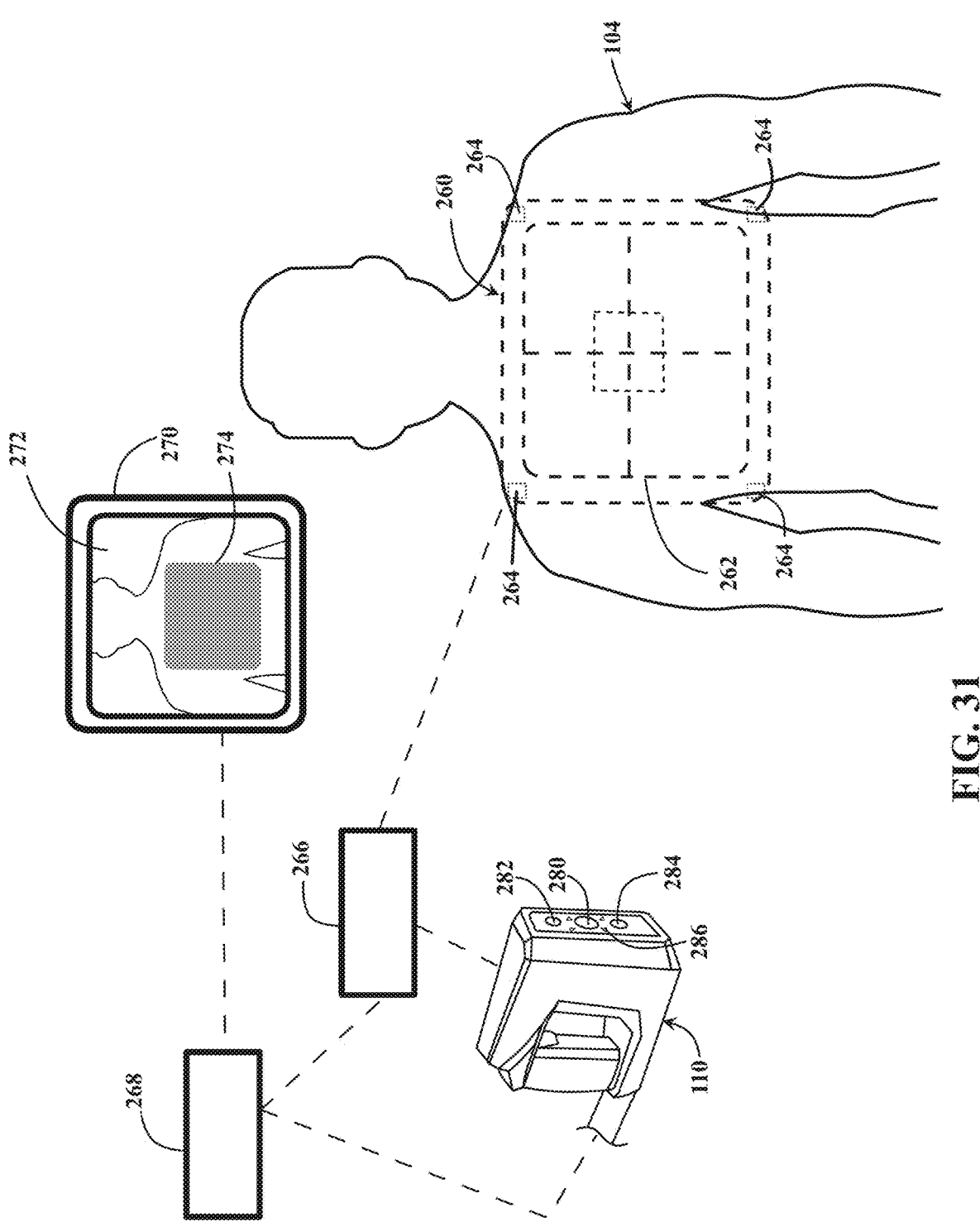
FIG. 31 represents a display of a first virtual representation of the boundary of the imaging sensor on the display.

FIG. 31 represents a display of a first virtual representation 274 of the boundary of the imaging sensor 262 on the display 270. As shown, the image 272 allows an X-ray user to observe the area of the individual 104 that is aligned with the imaging sensor 262. The image 272 can be a still capture image, real-time video, or a video segment when the user actuates a setting prior to emitting X-ray energy from the emitter. As shown, the point-of-view of the camera 282 will match or be sufficiently close to a point-of-view of the emitting window 280 such that the image 272 view corresponds with the ultimate X-ray image. The system shown in FIG. 31 can also optionally show a light field (as shown in FIG. 30) on the patient 104 as well as a virtual representation of the light field/X-ray projection area on the monitor 270 prior to discharging X-ray emission from the emitter.

Figure 32:
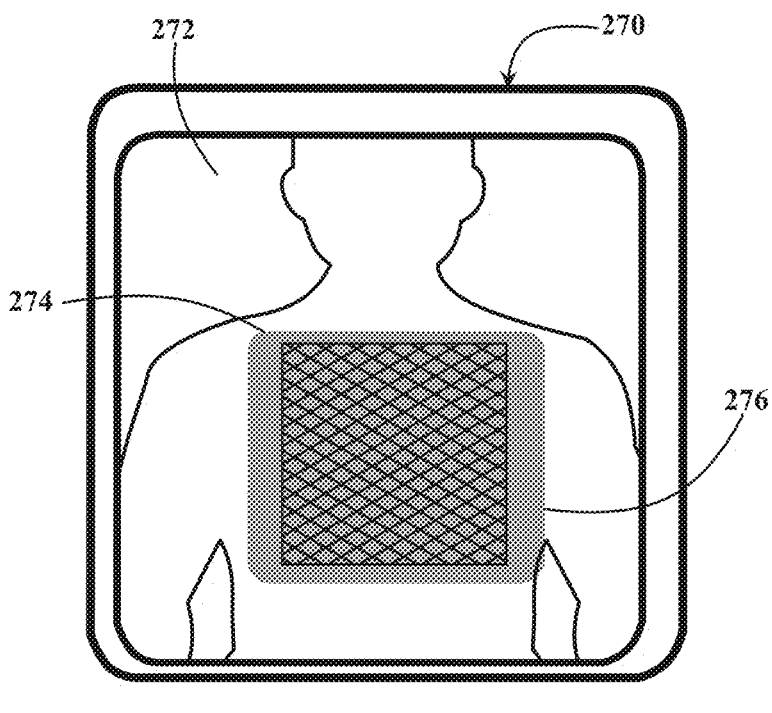
FIGS. 32 and 33 show additional examples of images overlayed with virtual images of the boundary of an imaging sensor.
Figure 33:
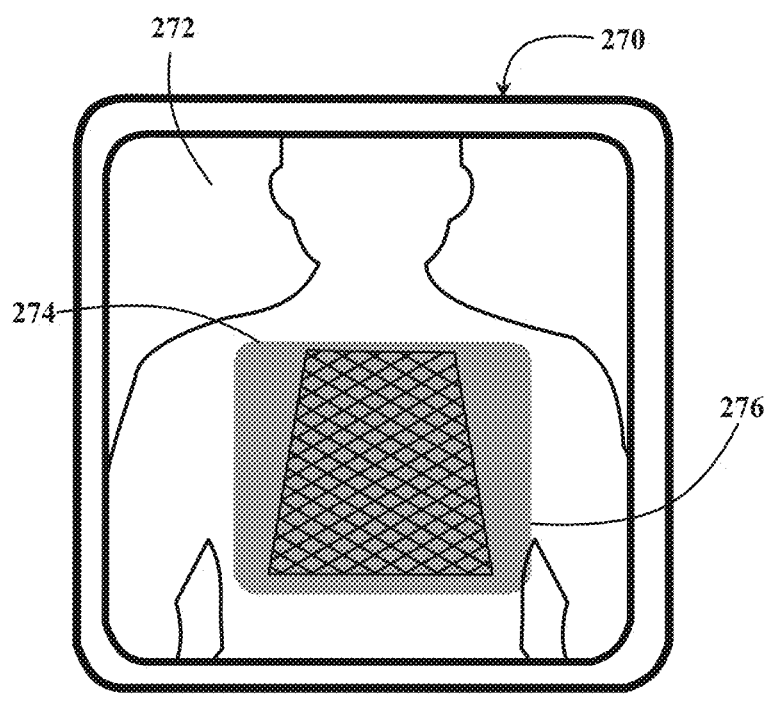

FIGS. 32 and 33 show additional examples of images 272 overlayed with virtual images 274 of the boundary of an imaging sensor. FIGS. 32 and 33 also show second virtual images 276 that represents the area of X-ray radiation emitted from the emitter that will be incident on the individual and image sensor. If the system uses a light-field projection from the emitter, the second virtual image 276 can correspond to the light-field projection on the patient. In this way, the operator can use both virtual images 274 and 276 to ensure that the intended object of the X-ray image is within the overlapping areas. FIG. 32 illustrates a condition where the emitter (not shown in FIG. 32) is in a normal direction to the object and the image sensor. FIG. 33 illustrates a variation of a system where the camera image 272 is shifted in perspective to appear normal to the patient, and image sensor, either through movement of the camera on the emitter or via digital processing of the image. However, FIG. 33 shows skewing of the projected X-ray projection area through skewing of the second virtual image 276 representing the X-ray emission area. This feature allows a user to recognize that the emitter is not positioned in a normal direction relative to the object when viewing the monitor 270.

Figure 34A:
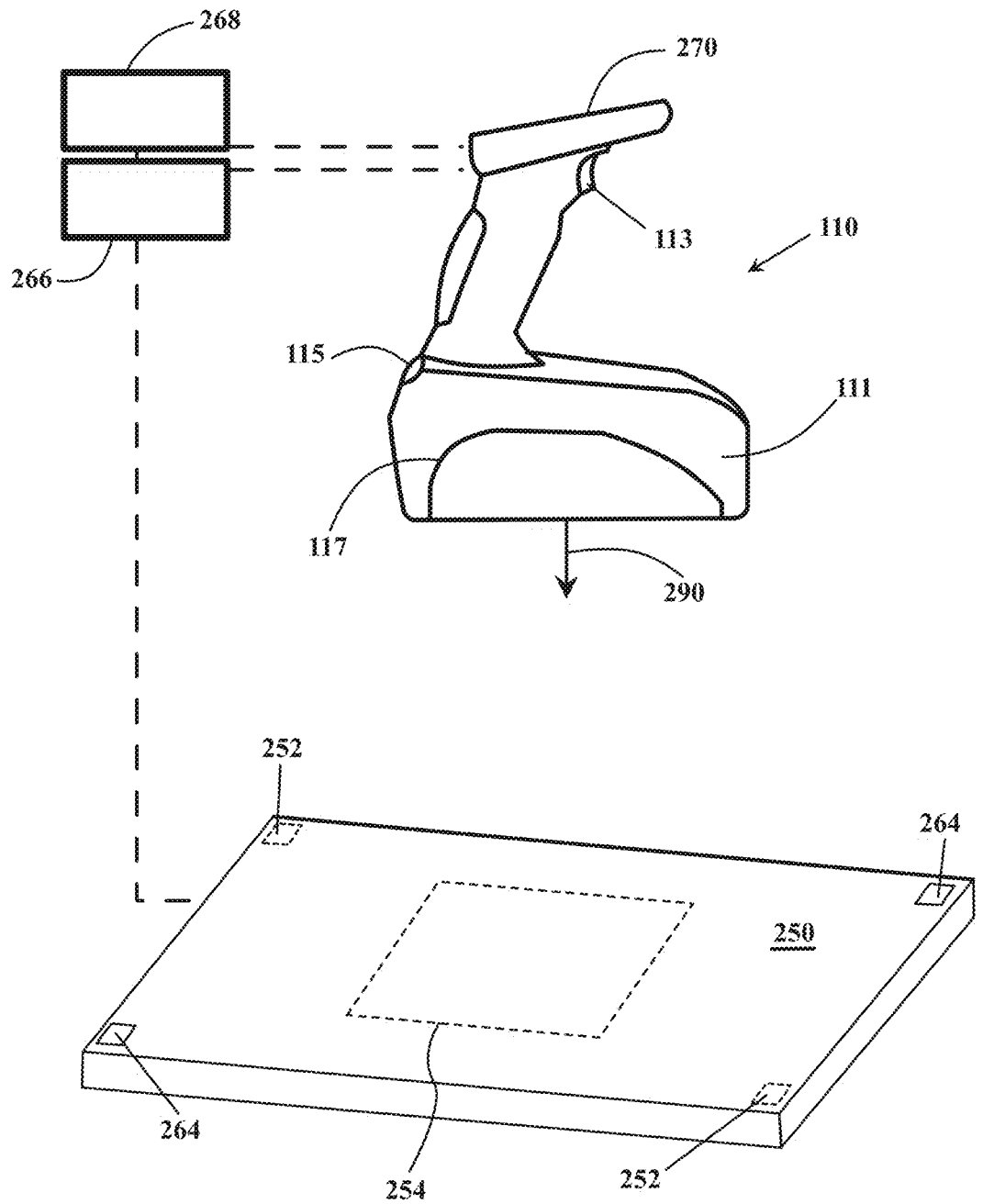
FIGS. 34A to 34C show another variation of an emitter having a screen that allows operation of the emitter and observation of the monitor in two configurations.

FIG. 34A shows another variation of an X-ray system using both non-line-of-sight-tracking elements, such as electromagnetic tracking sensors 252, and line-of-sight elements 264, as described above. Again, any variation of the system disclosed herein can include either non-line-of-sight tracking elements, line-of-sight tracking elements, or a combination of elements. FIG. 34A also illustrates an X-ray emitter 110 having a screen 270 on an end of the unit 110 opposite to a body 111 that carries the hardware and emitting apparatus of the unit. In such an example, the emitter window is located on the bottom face of the body 111 such that a field of view 290 of an emission or camera is directed away from the body 111, as shown by 290. The emitter 110 operates as discussed herein, where any number of sensors 252 and/or 264 can be used as required. In operation, the sensors 252 and/or 264 allow the system 266 to determine the relative location of the emitter 110 relative to the image sensor 254. As discussed above, the emitter 110 includes one or more cameras (not shown in 34A) that transmit signals to a processing unit 268, which produces an image of the field of view from the emitter 110 using the camera signal that can be displayed on the emitter 110 via a monitor 270 or on a separate monitor. In the variation of the emitter 110 shown in FIG. 34A, the emitter includes a first trigger 113 and a second trigger 115 that allow a user to grip the emitter in different configurations depending on the X-ray image required. Moreover, the emitter 110 can include any number of features (e.g., a side contour, graphic, etc.) to provide a physical visual indicator to show where the X-ray emission exits the emitter 110.

Figures 34B, 34C:
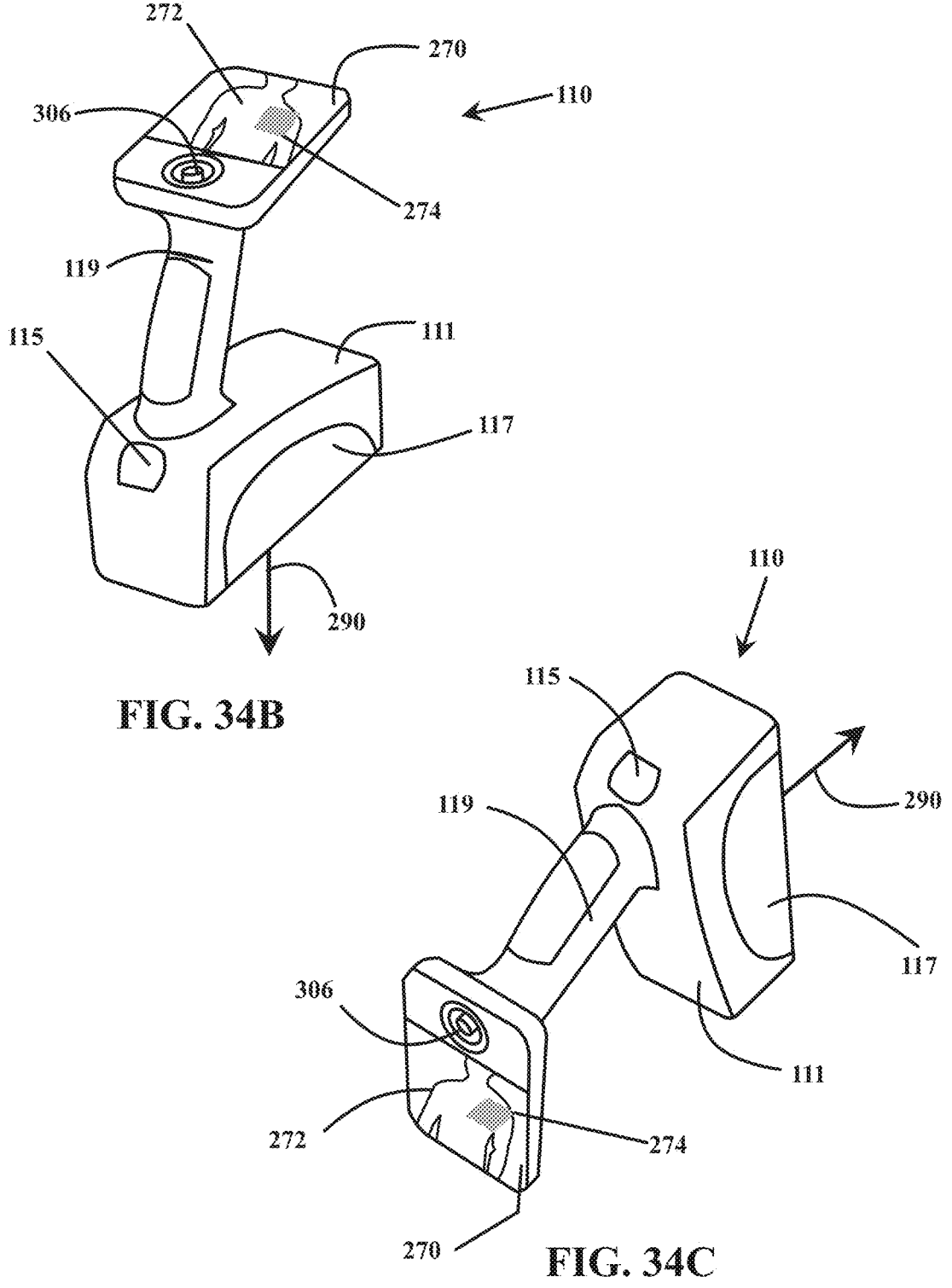

FIGS. 34B and 34C illustrate the emitter 110 shown in FIG. 34A, where a grip portion 119 of the emitter 110 is located between the body 111 and the monitor 270. This configuration permits operation of the emitter 110 in two different configurations. FIG. 34B shows a configuration where the emitter 110 is held over the object/patient such that the field of view 290 of the emission and camera exits in a bottom direction. In such a case, the operator can view the image 272 as well as the virtual image 274 of the image sensor on the monitor 270 while using a control switch 306. The first activation trigger (shown in FIG. 34A) can be accessed by the same hand grasping the grip portion 119. In FIG. 34C, the operator points the bottom of the body 110 in a direction to the object being imaged, as shown by field-of-view 290. In this variation, the operator can view the monitor 270 and adjust the control knob 306 while accessing the second trigger 115 with a thumb. It is noted that the monitor shown in FIGS. 34A to 34C can provide the same information as shown in FIG. 33A or 33B.

Another aspect of the system and methods includes simultaneous capture of a digital photograph (through the camera) and a corresponding X-ray image of an area of interest. Mating of the digital image to its corresponding X-ray image is useful for documentation purposes and enables future AI workloads and classifier algorithms to better identify the orientation and anatomy of the X-ray image. Moreover, without mating of a digital image with a corresponding X-ray image, an operator, observing a previously taken X-ray image, is forced to use a best guess as to the orientation and alignment of the X-ray source to the X-ray detector for that previous image. Unfortunately, this frequently causes a need for a reshoot. It is estimated that over 22% of reshoots are due to simple positioning errors. The ability to merge an X-ray with a digital image of the object/body part can improve outcomes of any subsequent X-ray images. In another aspect of the systems and methods, the imaging system can include a depth-sensing camera. For example, the emitter can include a LIDAR array (e.g., 256 pixels) determines depth. This depth (thickness) and shape of the anatomy can be used to refine the size of the anatomical illustration.

Figure 35:
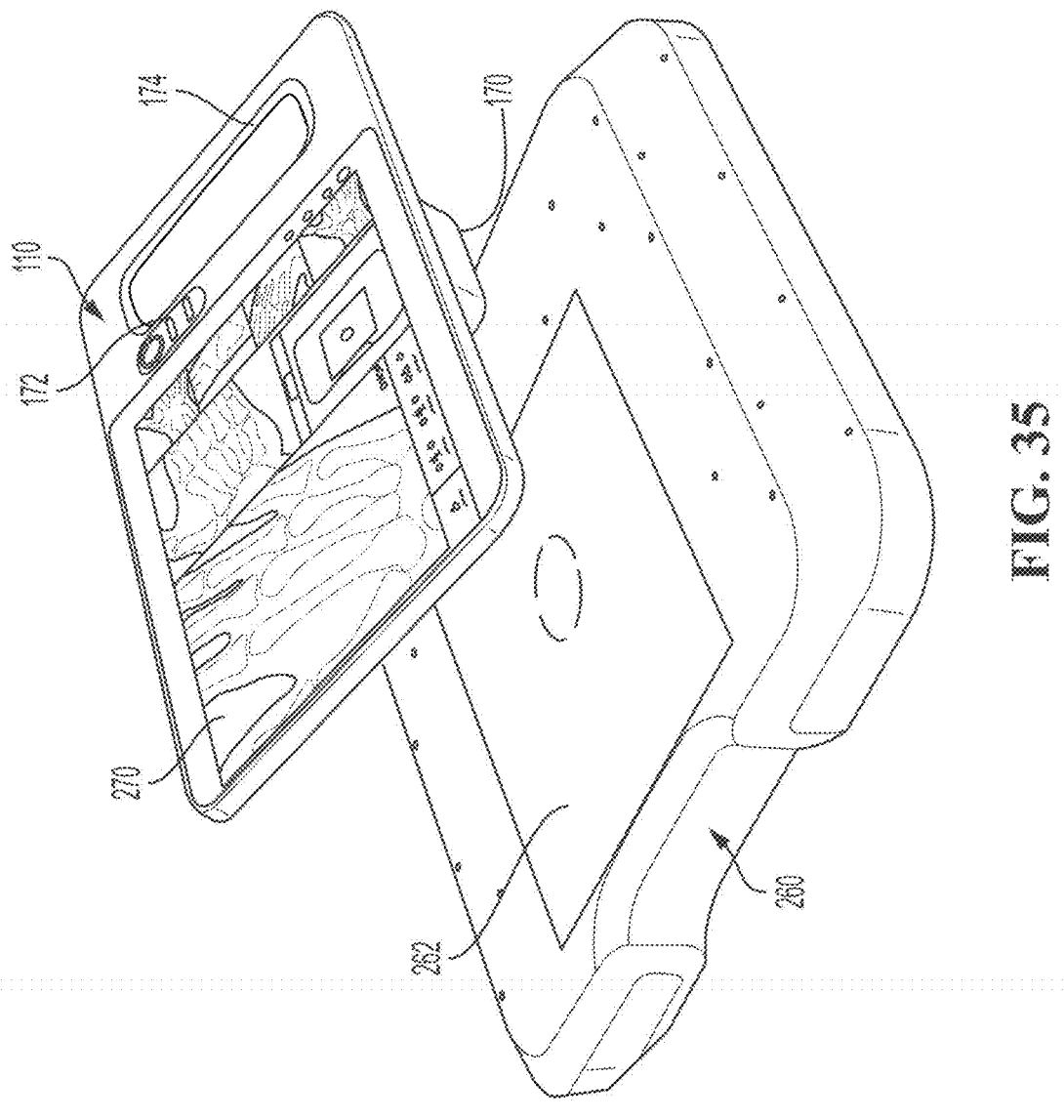
FIG. 35 illustrates a tablet-type emitter for improving the ability of an operator to take an X-ray image.

FIG. 35 illustrates another aspect of the systems and methods for improving the ability of an operator to take an X-ray image. As discussed above, systems and devices of the present disclosure can use a positioning system to show a dynamic view of the X-ray detector 262 through a display 270. In the variation shown in FIG. 35, an emitter 110 includes a large display 270 that allows for the operator to observe a real-time, dynamic view of the working surface 260/imaging sensor 262. As illustrated, the display 270 can be segmented to provide multiple views of different information rather than a single window. For example, and as shown, the display 270 can show previous X-ray images or additional information as discussed below. The emitter 110 shown in FIG. 35 comprises a tablet-like form where the rear side 170 includes components, including but not limited to an emitter window, one or more cameras, a lidar or similar component, etc. The emitter-tablet 110 can also include any number of ergonomic features, such as a finger/hand opening 174 that allows ease of positioning of the emitter 110 and ergonomic access to controls 172. In an additional variation, the information provided on any display associated with the emitter 110 can also be provided on an external display or monitor that is separate from the emitter 110 unit.

Figure 36A:
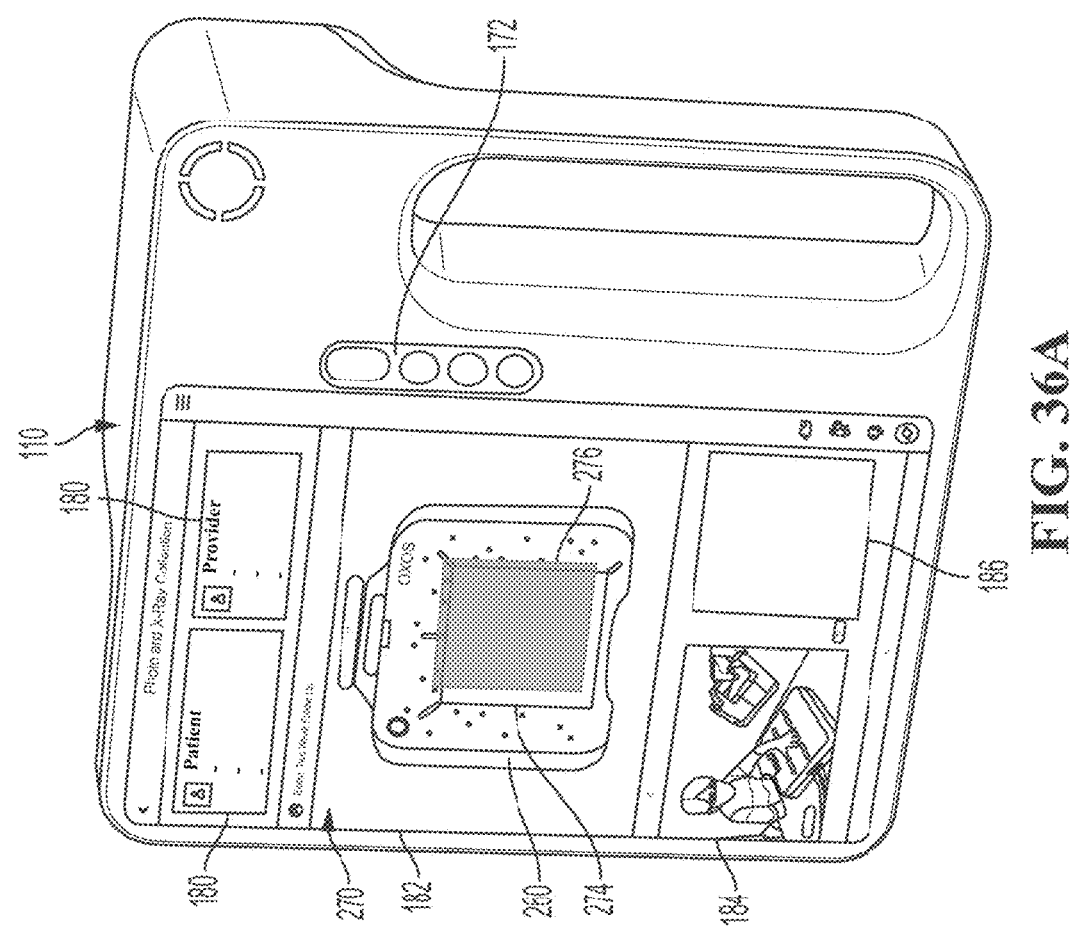
FIGS. 36A TO 36C illustrate an example of a system as described in FIG. 35 with various information displayed in a display of the tablet-emitter.

FIG. 36A illustrates an example of a system as described in FIG. 35 with various information displayed in a display 270 of the tablet-emitter 110. It is noted that while the system described herein can include the use of a positioning system (described above), the features and information provided in any visual display 270 can be applied to any X-ray system, including but not limited to a traditional C-arm imaging system. Again, the rear side 170 of the table-emitter 110 includes one or more apertures for an emitter, camera lens, lidar, or other components shown on the emitter of FIG. 32. Moreover, the camera system/lens can be configured to take an image or video from a perspective that matches or is close to the perspective of any X-ray image taken by tablet-emitter 110.

FIG. 36A illustrates the display 270, including a number of subset displays 180, 182, 184, and 186. These displays can provide information in information displays 180 regarding the patient, physician, or other data that is associated with the patient and/or X-ray image. The display 270 can also include informational displays 184 to guide the operator when taking the X-ray image. The display 270 can also include a working display 182 that allows real-time visualization of the working surface/enclosure 260 that houses an imaging sensor (not shown) as well as a first virtual image 274 representing the imaging sensor as well a second virtual image 276 representing the area of X-ray radiation to be emitted from the emitter 110 that will be incident on the image sensor and/or individual. The display 270 shown also includes an X-ray display 186, which can be used to display the X-ray obtained during the examination. In this illustration, the X-ray display 186 is blank.

The subset displays shown in FIG. 36A are exemplary only, and the disclosure includes any combination of subset displays as well as a single display. Typically, the operator can change displays using controls 172 on the unit.

Figure 36B:
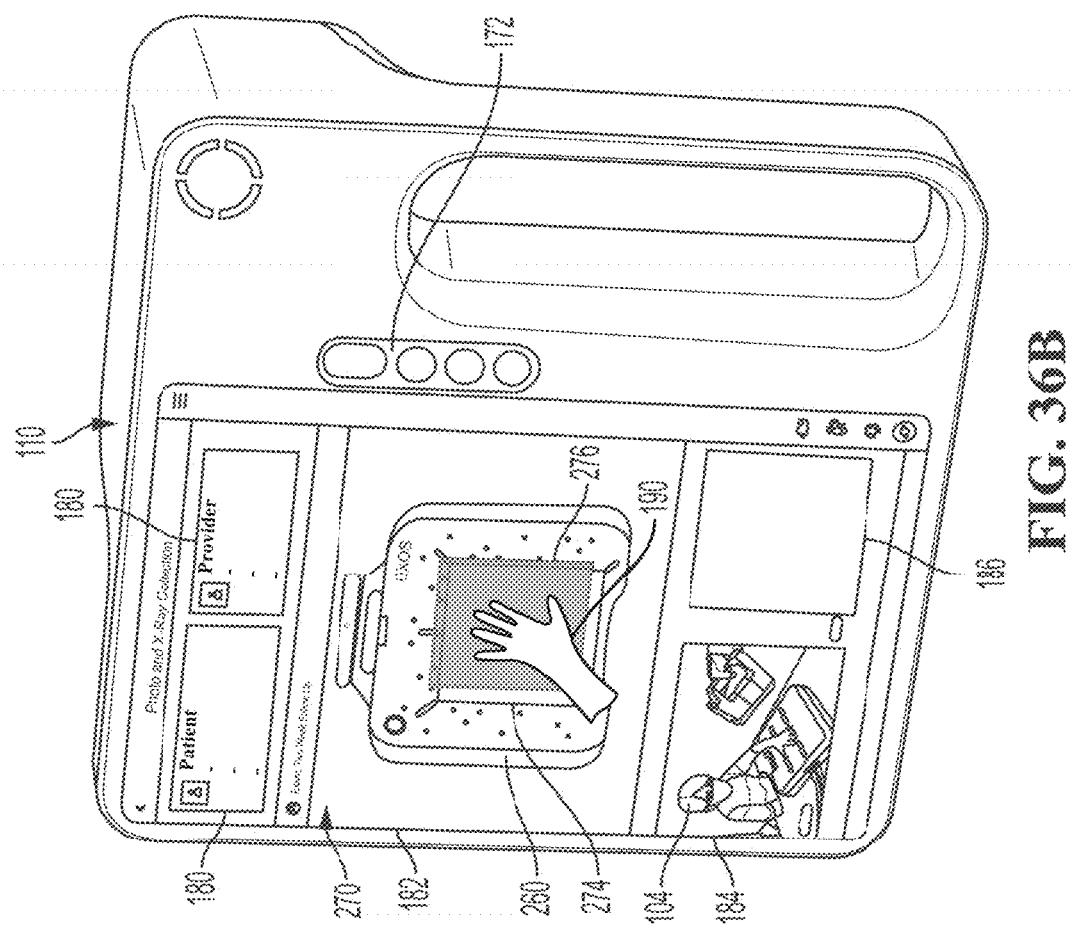

While FIG. 36A illustrates a condition prior to taking an X-ray, FIG. 36B illustrates a state where the operator receives information regarding the type of X-ray image required. As discussed below, the informational display 184 can display information to the operator, such as a setup image that shows the ideal positioning of the individual 104/body part. The setup image can also optionally show suggested positioning of the operator, emitter, and/or any accessories. While the image shown in FIG. 36B also shows a suggested orientation of an emitter, and alternate images are within the scope of this disclosure. For example, the informational display can also show an exemplary orthogonal photo of a picture of the desired anatomy, which gives the operator a preview of how the subject/anatomy being examined should appear in the viewfinder/working display 182.

FIG. 36B also can include a virtual or vector anatomical representation 190 of the desired position of a body part that is intended for imaging by the system. This virtual anatomical representation 190 can comprise a vector rendering of the orthogonal image, setup image, or can comprise a separate virtual image. Regardless, the virtual representation 190 is intended to assist the operator in positioning the patient prior to X-ray capture.

Figure 36C:
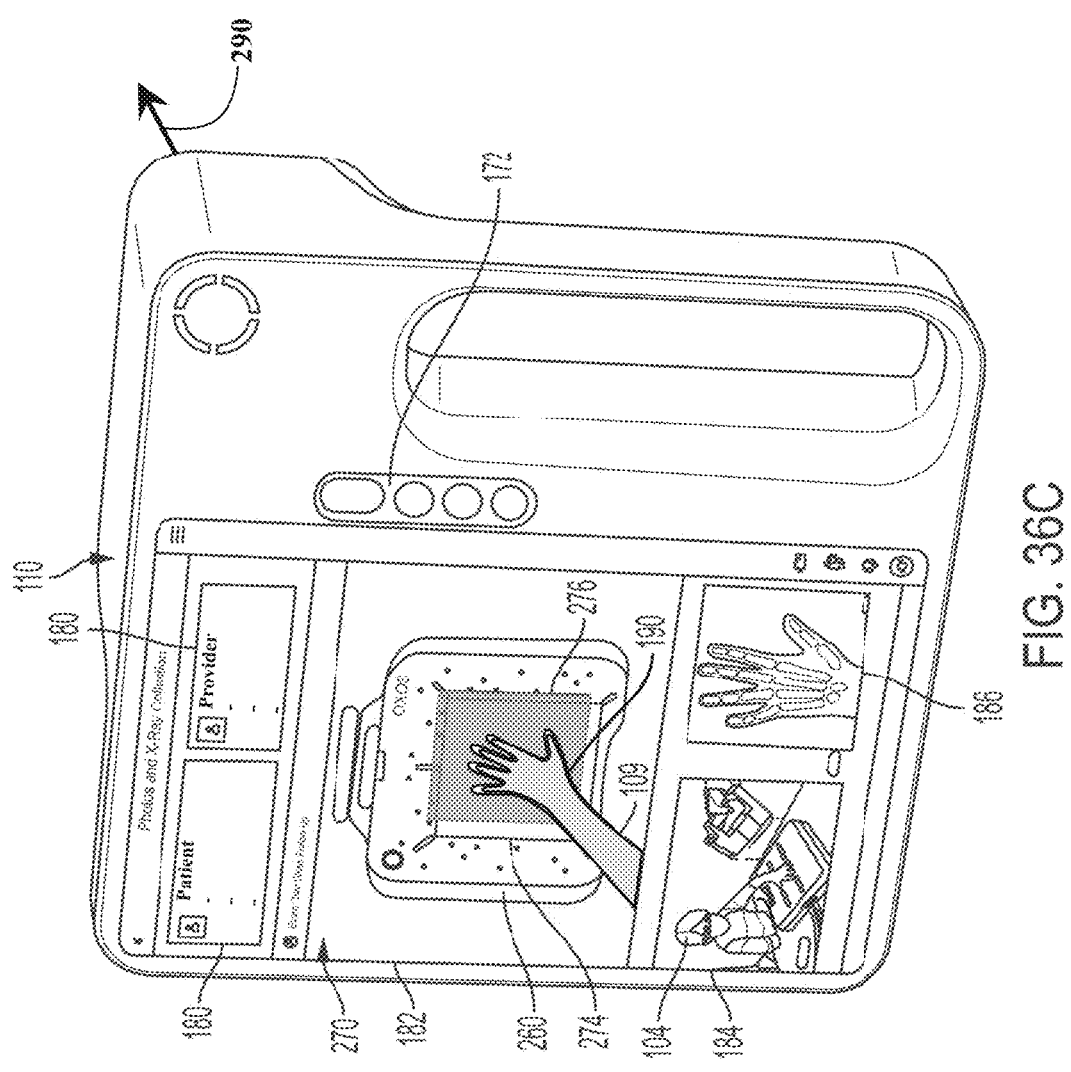

FIG. 36C illustrates positioning of a patient's body part 109 using the virtual representation 190 such that the operator can proceed with X-ray image capture to produce an X-ray image 186. As noted herein, providing the operator with such information allows for individuals with minimal training to capture X-ray images that are typically required when performing an evaluation of an individual. Moreover, variations of the system can compare the captured X-ray image 186 to any appropriate reference image from the library discussed above. The system can include the use of artificial intelligence to compare the captured X-ray image 186 to a reference X-ray image and provide a score to guide the operator as to the desirability of the captured X-ray image. In some variations, the system can prompt the operator to re-capture an additional X-ray image using different positioning and/or X-ray emission settings.

It is noted that any of the virtual representations (e.g., 190, 274, 276, etc.) can be triggered on or off depending on the operator's preference. Moreover, the system further includes the option of providing a visual representation of only the overlapping regions of 190, 274, 276, so that the operator ensures alignment of the body part and emitter with the image sensor.

The systems and methods described herein that provide visual images, as well as virtual images, provide real-time, dynamic views to give operators a picture of the anatomy imaged before generating the X-ray. In addition, the systems can guide the operator to specific X-ray views by overlaying a diagram of the subject anatomy directly on the image display and view, corrected for the active area of the image sensor. Such a system can increase clinical use of the systems in those cases where the operator is not a physician or an experienced X-ray technician.

For example, the reference images can help a user capture the best views or those views commonly required for assessment of a body part. Accordingly, the system can be networked with a database or library of data that guides an operator in taking one or more proper X-ray images.

For example, this database can include a library of images as well as other instructional materials to aid the operator. For example, the library can include a view name, any number of reference X-ray images, any number of reference photos, and any number of patient alignment photos. One goal of such information is to give the operator a visual guide of the anatomy imaged before generating the X-ray.

FIG. 37A illustrates one example of a description of a data element or record 312 that is part of a database intended for interaction with X-ray imaging systems. As noted herein, the database and visual display can be used with systems that track positioning of the emitter relative to the image sensor. Alternatively, the database and images can be used with traditional X-ray equipment, including but not limited to C-Arms, or other radiographic equipment.

FIG. 37A shows an exemplary record 312 of separate data fields. For example, such data fields can include: a view name 314, anatomy 316, one or more reference x-rays 318 (such as an image from an academic or other reference sources), settings for the system in communication with the database (so that the operator does not need to adjust settings for different captures), reference X-ray images taken by the system or similar systems 322, orthogonal images 324, setup images 328, and accessory information 328. The listing of data fields is intended for illustrative purposes only. Any combination of data fields or additional data fields is within the scope of this disclosure.

Figure 37B:
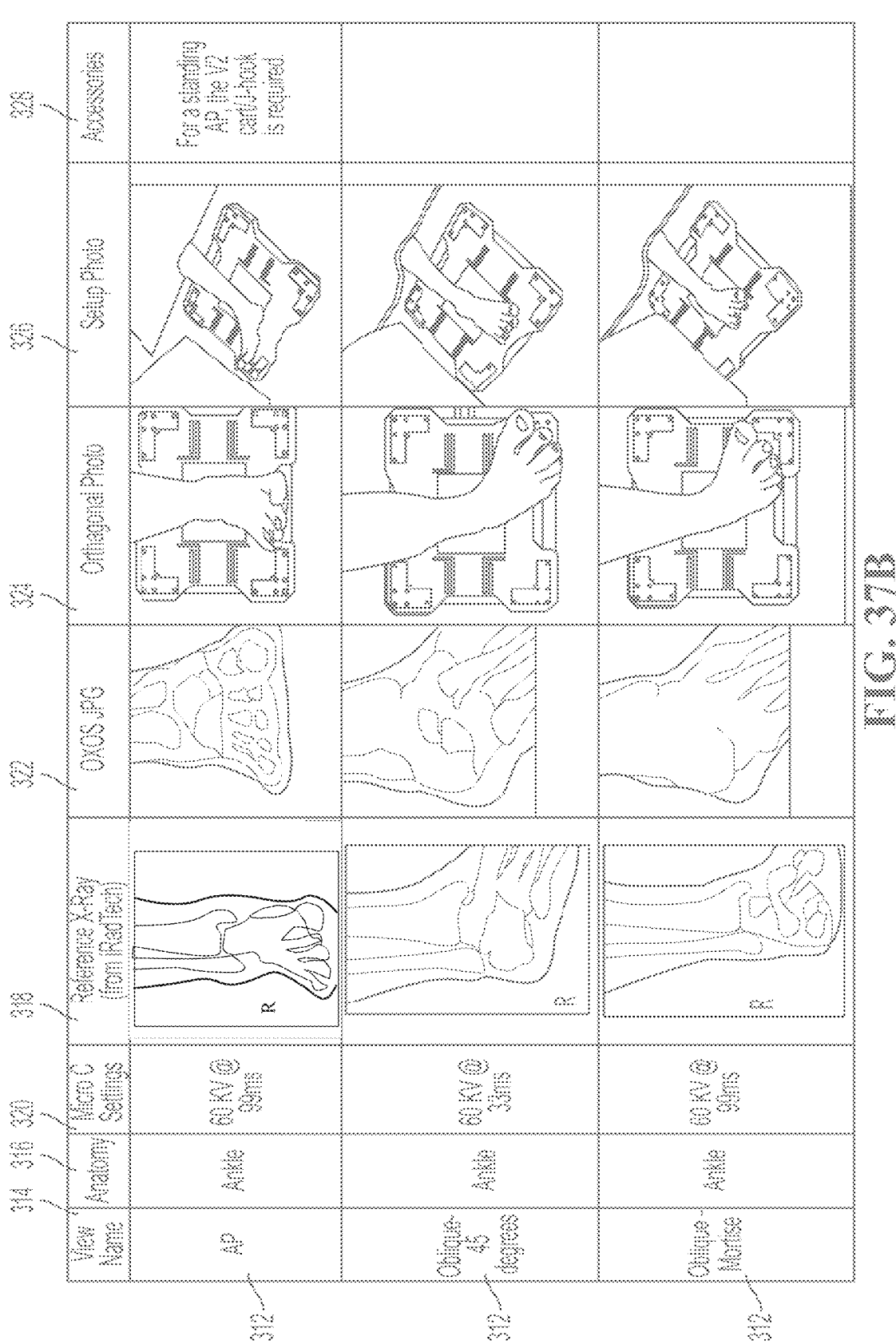

FIGS. 37B and 37C illustrate an example of three records 312, each having various data fields comprising descriptive text (314, 316, 328, 330), X-ray system settings (320), X-ray reference images (318, 322), and visual images (324, 326). In one example, where a caregiver requires X-ray images for a follow-up examination of a patient, the system can receive records 312 from an appropriate database. Records 312 are then displayed as noted above to guide the operator to obtain the images desired for the follow-up examination. As noted above, the individual records 312 can be standard X-ray views, or a caregiver can select desired records to select the desired X-ray images. In an additional variation, an operator is initially examining an individual (e.g., in a field setting such as ordinary patient intake, an accident site, or triage situation), the operator can indicate the anatomy requiring an exam, and the system can then pull or receive relevant records to guide the operator into taking the required X-ray images.

The information discussed above in FIGS. 37A to 37C is an example of radiographic imaging information that can assist an operator in obtaining a proper radiographic image and/or operate the X-ray emitter 110 and/or X-ray system.

Figure 38:
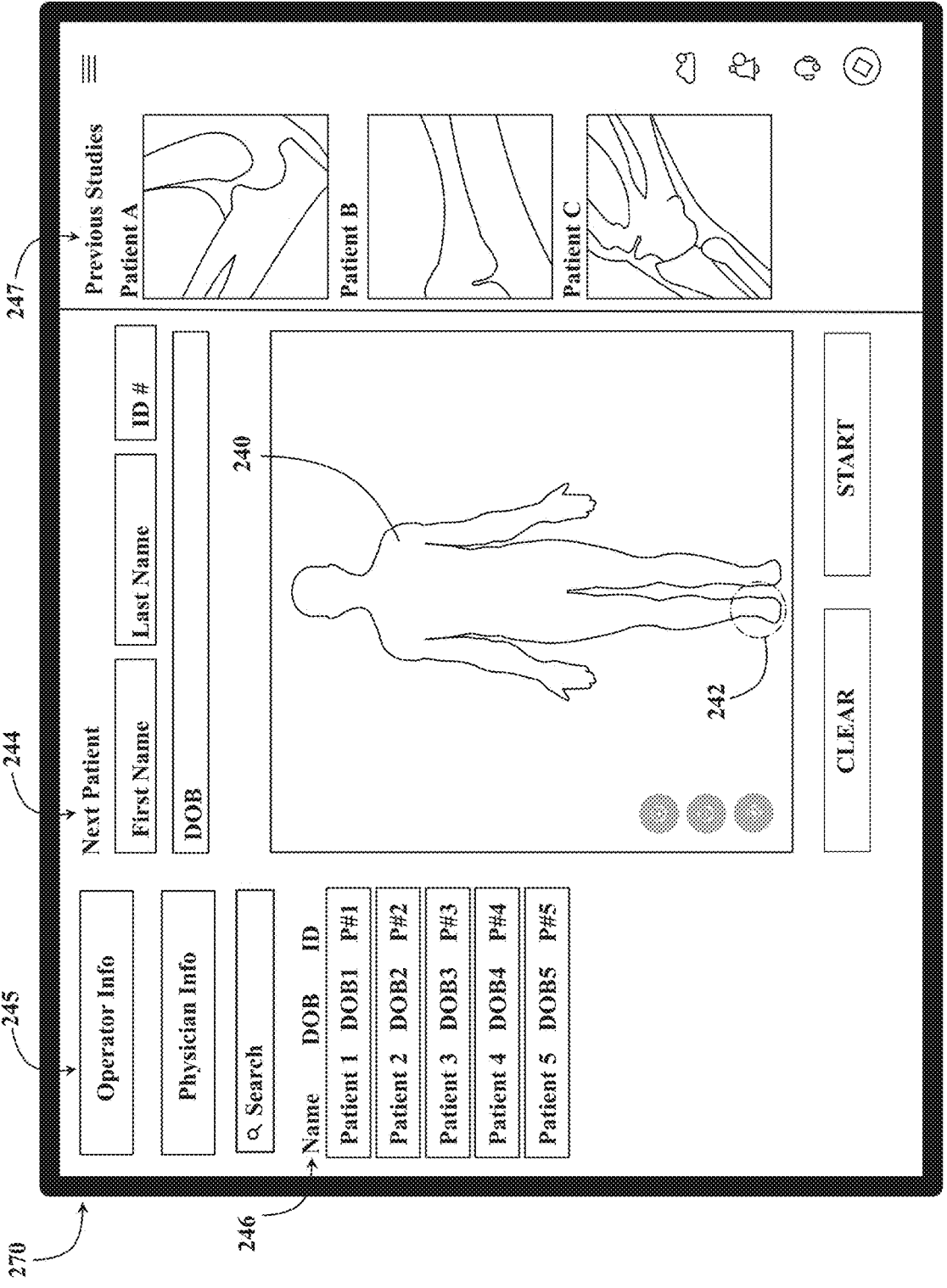
FIG. 38 illustrates an additional variation of a display configured to assist an operator to obtain a radiographic image at an initial screening of an individual

FIG. 38 comprises an additional variation of a display 270 configured to assist an operator to obtain a radiographic image at an initial screening of an individual. In this example, the operator is provided with an anatomic representation 240 that allows the operator to select any number of anatomic regions to receive information that will assist in obtaining the desired X-ray. The operator can then select one or more anatomic regions that require X-ray imaging. As an example, in the variation shown in FIG. 38, the operator selects the ankle area 242 on the anatomic representation 240. Accordingly, the operator can then be prompted with various informational images from a database or library, as discussed above, such as those shown in FIG. 37B, which shows various standard positions of the ankle required to obtain X-ray images. Accordingly, the operator can position the individual's ankle using the informational displays as well as any virtual overlays as discussed above to obtain an X-ray image for later assessment by a medical caregiver.

An alternate variation of the display 270 can include an anatomic representation 240 that comprises textual information to allow the operator to identify an anatomic area. In addition, the anatomic representation 240 can comprise a subset of an anatomic region instead of the entire body.

The display 270 of FIG. 38 can also include various additional data, including but not limited to patient data 244, operator/physician info 245, a database of patients 246 that are scheduled for examination, as well as a historical section 247 of previous X-ray captures by the operator.

The systems and methods described herein that provide visual images, as well as virtual images, provide real-time, dynamic views to give operators a picture of the anatomy imaged before generating the X-ray. In addition, the systems can guide the operator to specific X-ray views by overlaying a diagram of the subject anatomy directly on the image display and view, corrected for the active area of the image sensor. Such a system can increase clinical use of the systems in those cases where the operator is not a physician or an experienced X-ray technician.

In yet a further variation of the system, the system can include one or more processors that use artificial intelligence to match the captured X-ray image with the reference image 318 and/or template image 322 to determine if the captured X-ray matches a reference image of the requested X-ray. If the artificial intelligence provides a sufficient match (e.g., via a similarity score), the operator can move on to capture subsequent images. If the match is insufficient, the system can alert the operator to re-take the image.

While the above descriptions provide exemplary details of the invention in order to provide an understanding of the invention, routine engineering adjustments may be employed to practice the invention without departing from the spirit or scope of the invention. Further, while the invention is described for use in X-ray imaging for surgical purposes, it could be used in other medical applications such as general medical imaging, veterinary, and bone densitometry. The system and method may also be used for non-medical applications such as industrial imaging, metal fatigue inspections, weld-inspection, for security inspections, and the like.

We claim:

1. A method of obtaining a radiological image of an individual or a body part by an operator, the method comprising:

positioning an emitting apparatus at a distance from a working surface, where the working surface includes an imaging sensor, the emitting apparatus including a camera system and an aperture opening configured to pass an emission energy therethrough;

orienting the emitting apparatus such that the aperture opening and the camera system face towards the working surface;

transmitting a signal from the camera system to a display to produce an image of the working surface on the display;

providing at least one informational image on the display for viewing by the operator, where the at least one informational image comprises a suggested positioning of the individual or the body part; and emitting the emission energy to the imaging sensor to produce the radiological image of the individual or the body part and displaying the radiological image on the display.

2. The method of claim 1, further comprising providing a virtual anatomical representation of the body part on the image, where the virtual anatomical representation is over-laid on the working surface on the image.

3. The method of claim 1, wherein the imaging sensor comprises a detecting perimeter, the method further comprising displaying a virtual detecting perimeter on the display, where the virtual detecting perimeter is overlaid on the working surface and corresponds to the detecting perimeter.

4. The method of claim 1, further comprising displaying a virtual emission perimeter on the display, where the virtual emission perimeter is overlaid on the working surface and corresponds to an emission perimeter of the emission energy from the aperture opening.

5. The method of claim 1, wherein providing the at least one informational image further comprises providing an instructional message a text instruction or a video instruction on the display.

6. The method of claim 1, further comprising displaying the radiological image on the display wherein the image comprises at least one non-video image.

7. The method of claim 1, further comprising providing an informational data on the display, where the informational data comprises data associated with the individual.

8. The method of claim 6, wherein the display comprises a plurality of subset displays, wherein the image of the working surface is displayed on a first subset display and wherein the radiological image is displayed on a second subset display.

9. The method of claim 1, wherein providing the at least one informational image comprises selecting one or more images from a first database containing a plurality of radiographic imaging information.

10. The method of claim 1, further comprising, prior to positioning the emitting apparatus, displaying an anatomic representation on the display, the anatomic representation having one or more anatomic areas, where the display is configured to permit the operator to select one or more of anatomic areas to pre-select the at least one informational image provided on the display for viewing by the operator.

11. The method of claim 1, further comprising performing a comparison of the radiological image to a reference radiological image and providing feedback to the operator based on the comparison.

12. A system for obtaining a radiological image of a body part on a working surface having an X-ray image sensor, the system comprising:

an emitting apparatus including a camera system and an aperture opening configured to pass an emission energy therethrough, where the emitting apparatus comprises a display configured to show an image of the working surface generated by the camera system;

the emitting apparatus configured to communicate with a database containing a plurality of radiographic imaging information data to display at least one informational image for viewing by an operator of the emitting apparatus, where the at least one informational image comprises a suggested positioning of the body part; and where the display configured to show a virtual anatomical representation of the body part on the image of the working surface, and where the display is configured to provide the radiological image after the emission energy is emitted on the body part and the X-ray image sensor.

13. The system of claim 12, wherein the display is configured to provide the radiological image after the emission energy is emitted on the body part and the X-ray image sensor wherein providing at least one informational image further comprises providing an instructional message on the display.

14. The system method of claim 13, wherein the instructional message at least one informational image comprises a text instruction or a video instruction.

15. The system of claim 12, wherein the at least one informational image comprises a video image.

16. The system of claim 12, wherein the at least one informational image comprises a suggested positioning of the body part wherein the image comprises at least one non-video image.

17. The system of claim 12, further comprising providing an informational data on the display, where the informational data comprises a data associated with the body part individual.

18. The system of claim 12, wherein the display comprises a plurality of subset displays, wherein the image of the working surface is displayed on a first subset display and wherein the radiological image is displayed on a second subset display.

19. The system of claim 18, wherein the at least one informational image is displayed on a third subset display.

20. The system of claim 12, wherein the emitting apparatus is in communication with a first database containing a plurality of radiographic imaging information and where the at least one informational image comprises one or more images from the first database containing a plurality of radiographic imaging information.

* * * * *